US009248122B2

(12) United States Patent
Kühnert et al.

(10) Patent No.: US 9,248,122 B2
(45) Date of Patent: Feb. 2, 2016

(54) HETEROQUINOLINE-3-CARBOXAMIDES AS KCNQ2/3 MODULATORS

(71) Applicant: GRÜNENTHAL GMBH, Aachen (DE)

(72) Inventors: Sven Kühnert, Düren (DE); Simon Lucas, Wolfsgraben (AT); Gregor Bahrenberg, Monschau-Konzen (DE); Wolfgang Schröder, Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/091,395

(22) Filed: Nov. 27, 2013

(65) Prior Publication Data

US 2014/0148478 A1 May 29, 2014

Related U.S. Application Data

(60) Provisional application No. 61/730,542, filed on Nov. 28, 2012.

(30) Foreign Application Priority Data

Nov. 28, 2012 (EP) ..................................... 12007990

(51) Int. Cl.
A61K 31/4375 (2006.01)
C07D 471/04 (2006.01)
C07D 495/04 (2006.01)
A61K 31/4365 (2006.01)
A61K 45/06 (2006.01)

(52) U.S. Cl.
CPC ......... A61K 31/4375 (2013.01); A61K 31/4365 (2013.01); A61K 45/06 (2013.01); C07D 471/04 (2013.01); C07D 495/04 (2013.01)

(58) Field of Classification Search
CPC .............. A61K 31/4375; A61K 45/06; A61K 31/4365; C07D 471/04; C07D 495/04
USPC .................... 514/301, 300; 546/123, 114, 122
See application file for complete search history.

(56) References Cited

U.S. PATENT DOCUMENTS

| 7,625,900 | B2 | 12/2009 | Merla et al. |
| 7,879,858 | B2 | 2/2011 | Merla et al. |
| 8,017,772 | B2 | 9/2011 | Merla et al. |
| 8,084,470 | B2 | 12/2011 | Merla et al. |
| 8,133,907 | B2 | 3/2012 | Blaszczak et al. |
| 8,178,684 | B2 | 5/2012 | Kuehnert et al. |
| 8,399,673 | B2 | 3/2013 | Kuehnert et al. |
| 8,445,512 | B2 | 5/2013 | Kuehnert et al. |
| 8,470,852 | B2 | 6/2013 | Kuehnert et al. |
| 8,552,200 | B2 | 10/2013 | Kuehnert et al. |
| 8,586,755 | B2 | 11/2013 | Kuehnert et al. |
| 2002/0128277 | A1 | 9/2002 | Dworetzky et al. |
| 2002/0183335 | A1 | 12/2002 | Hewawasam et al. |
| 2005/0250818 | A1 | 11/2005 | Koike et al. |
| 2008/0167315 | A1 | 7/2008 | Merla et al. |
| 2008/0214616 | A1 | 9/2008 | Blaszczak et al. |
| 2009/0076086 | A1 | 3/2009 | Merla et al. |
| 2009/0258880 | A1 | 10/2009 | Merla et al. |
| 2010/0004252 | A1 | 1/2010 | Merla et al. |
| 2010/0022589 | A1 | 1/2010 | McCoull et al. |
| 2010/0105722 | A1 | 4/2010 | Kuehnert et al. |
| 2010/0234372 | A1 | 9/2010 | Kuehnert et al. |
| 2010/0234429 | A1 | 9/2010 | Kuehnert et al. |
| 2012/0053204 | A1 | 3/2012 | Kühnert et al. |
| 2012/0053205 | A1 | 3/2012 | Kuehnert et al. |
| 2012/0101079 | A1 | 4/2012 | Kuehnert et al. |
| 2012/0184550 | A1 | 7/2012 | Kuehnert et al. |
| 2012/0220627 | A1 | 8/2012 | Kuehnert et al. |
| 2012/0252841 | A1 | 10/2012 | Kuehnert et al. |
| 2012/0258947 | A1 | 10/2012 | Kühnert et al. |

FOREIGN PATENT DOCUMENTS

| EP | 1 219 609 | 7/2002 |
| WO | 94 15608 | 7/1994 |
| WO | 02 066036 | 8/2002 |
| WO | 2005 105733 | 11/2005 |
| WO | 2005/105733 A1 | 11/2005 |
| WO | 2006 058905 | 6/2006 |
| WO | 2007 015767 | 2/2007 |
| WO | 2007/015767 A1 | 2/2007 |
| WO | 2007 138110 | 12/2007 |
| WO | 2008 012532 | 1/2008 |
| WO | 2008 046582 A1 | 4/2008 |
| WO | 2009 036938 | 3/2009 |

(Continued)

OTHER PUBLICATIONS

Dorange et. al. "Recent Progress in the Discovery of Kv7 Modulators" Annual Reports in Medicinal Chemistry, 2011 vol. 46 pp. 53-65.*
Brown, D. A. "Some Pharmacological Properties of Neural KCNQ Channels." Neurophysiology 2002, 34(2-3), 91-94.*
Cheung Yiu-Yin "Discovery of a Series of 2-Phenyl-N-(2-(pyrrolidin-l-yl)phenyl)acetamides as Novel Molecular Switches that Modulate Modes of Kv7.2 . . ." Journal of Medicinal Chemistry, 2012 55(15), 6975-6979.*
Yu, Haibo; "Discovery, Synthesis, and Structure-Activity Relationship of a Series of N-Aryl-bicyclo[2.2.1]heptane-2-carboxamides: Characterization of ML213 as a Novel KCNQ2 and KCNQ4 Potassium Channel Opener." ACS Chemical Neuroscience, 2011 2(10) 572-577.*
Amato, George "N-Pyridyl and Pyrimidine Benzamides as KCNQ2/Q3 Potassium Channel Openers for the Treatment of Epilepsy." ACS Medicinal Chemistry Letters, 2011 2(6), 481-484.*

(Continued)

Primary Examiner — Janet L Andres
Assistant Examiner — Daniel Carcanague
(74) Attorney, Agent, or Firm — Norris McLaughlin & Marcus, P.A.

(57) ABSTRACT

The invention relates to substituted heteroquinoline-3-carboxamides, to pharmaceutical compositions containing these compounds and also to these compounds for use in the treatment and/or prophylaxis of pain and further diseases and/or disorders.

20 Claims, No Drawings

(56) References Cited

FOREIGN PATENT DOCUMENTS

| WO | 2010 046108 A1 | 4/2010 |
| --- | --- | --- |
| WO | 2010 102809 | 9/2010 |
| WO | 2010 102811 A1 | 9/2010 |
| WO | WO 2010/097410 * | 9/2010 |
| WO | 2012 025236 A1 | 3/2012 |
| WO | 2012 025237 A1 | 3/2012 |
| WO | 2012 025238 A1 | 3/2012 |
| WO | 2012 052167 A1 | 4/2012 |

OTHER PUBLICATIONS

Fritch, Paul C.; "Novel KCNQ2/Q3 Agonists as Potential Therapeutics for Epilepsy and Neuropathic Pain." Journal of Medicinal Chemistry, 2010 53(2), 887-896.*
Hu, Hai-ning "Discovery of a retigabine derivative that inhibits KCNQ2 potassium channels" Acta Pharmacologica Sinica 2013 34(10), 1359-1366.*
Dorwald; "Side Reactions in Organic Synthesis: A Guide to Successful Synthesis Design" 2005 Wiley-VCH Verlag GmbH & Co. KGaA, Wienheim, chapter 1, pp. 1-16.*
P. Hewawasam et al. Bioorg. Med. Chem. Lett. 14 (2004) 1615-1618.*
D'Amour and Smith (J. Pharm. Exp. Ther. 72, 74 79 (1941).
D. Dubuisson et al., Pain 1977, 4, 161-174.
Zhou, Shao-Zhen et al,"Synthesis on new S,S-chelated Pd(I) complexes and their promoter effect on the hydrolytic cleavage of dipeptide", Chem. Abstr. Service, 1999.
European Search Report issued in corresponding application EP 12007990 dated Jan. 30, 2013.
European Search Report issued in corresponding application EP 12007991 dated Jun. 26, 2013.
European Search Report issued in corresponding application EP 12007992 dated Jul. 8, 2013.
Passmore et al; "KCNQ/M currents in sensory neurons: significance for pain therapy"; The Journal of Neuroscience, Aug. 6, 2003, 23(18), pp. 7227-7236.
Blackburn-Munro et al; "The anticonvulsant retigabine attenuates nociceptive behaviours in rat models of persistent and neuropathic pain": European Journal of Pharmacology 460 (2003) pp. 109-116.
Dost et al; "The anti-hyperalgesic activity of retigabine is mediated by KCNQ potassium channel activation" ; Naunyn-Schmiedeberg's Arch Pharmacol (2004) 369; pp. 382-390.
Gribkoff; "The therapeutic potential of neuronal KCNQ channel modulators"; Expert Opinion, Ther. Target, 2003; 7 (6); pp. 737-748.
Korsgaard et al; "Anxiolytic effects of maxipost (BMS-204352) and retigabine via activation of neuronal Kv7 channels"; The Journal of Pharmacology and Experimental Therapeutics; Vo. 314, No. 1, pp. 282-292, (2005).
Wickenden et al; "KCNQ potassium channels: drug targets for the treatment of epilepsy and pain"; Expret Opinion, Monthly focus: Central & Peripheral Nervous Systems; Ashley Publications Ltd. 2004; pp. 457-469.
Gribkoff; Central & Peripheral Nervous Systems; "The therapeutic potential of neuronal Kv7 (KCNQ) channel modulators: an update"; Expert Opinion Ther. Targets 2008; 12(5); pp. 565-581.
Miceli et al; "Molecular pharmacology and therapeutic potential of neuronal Kv7-modulating drugs"; Current Opinion in Pharmacology 2008, 8, pp. 65-74.
Streng et al; "Urodynamic effects of K+ channel (KCNQ) opener retigabine in freely moving, conscious rats": The Journal of Urology, vol. 172, Nov. 2004, pp. 2054-2058.
Hansen et al; "The neuronal KCNQ channel opener retigabine inhibits locomotor activity and reduces forebrain excitatory responses to the psychostimulants cocaine, methylphenidate and phecyclidine"; European Journal of Pharmacology 570 (2007); pp. 77-88.
Dencker et al; "Effect of the new antiepileptic drug retrigabine in a rodent model of mania": Epilepsy & Behavior 12 (2008) pp. 49-53.
Richter et al; "Antidystonic effects of Kv7 (KCNQ) channel openers in the dt sz mutant, an animal model of primary paroxysmal dystonia": British Journal of Pharmacology (2006) 149, pp. 747-753.
Bennett et al; "A peripheral mononeuropathy in rat that produces disorders of pain sensation like those seen in man"; Pain, 33 (1988) pp. 87-107.

Kim et al; "An experimental model for peripheral neuropathy produced by segmental spinal nerve ligation in the rat" Pain, 50 (1992) pp. 355-363.
DeSarro et al; "Influence of retigabine on the anticonvulsant activity of some antiepileptic drugs against audiogenic seizures in DBA/2 mice"; Naunyn-Schmiedeberg's Arch Pharmacol (2001) 363 :330-336.
Nielsen et al; "Pharmacological characterisation of acid-induced muscle allodynia in rats"; European Journal of Pharmacology 487 (2004) pp. 93-103.
Ravin Louis J., "Preformulation", "Remington's Pharmaceutical Sciences", ed. A.R. Gennaro, 17th ed., Mack Publishing Company, Easton, Pa. (1985), Chapter 76, p. 1409-1423.
DiSanto, Anthony R., "Bioavialiblity and Bioequivalency Testing", "Remington's Pharmaceutical Sciences", ed. A.R. Gennaro, 17th ed., Mack Publishing Company, Easton, Pa. (1985), Chapter 77, p. 1424-1431.
Knevel, Adelbert M., "Separation", "Remington's Pharmaceutical Sciences", ed. A.R. Gennaro, 17th ed., Mack Publishing Company, Easton, Pa. (1985), Chapter 78, p. 1432-1442.
Phillips, G Briggs et al., "Sterilization", "Remington's Pharmaceutical Sciences", ed. A.R. Gennaro, 17th ed., Mack Publishing Company, Easton, Pa. (1985), Chapter 79, p. 1443-1454.
Siegel, Frederick P., "Tonicity, Osmoticity, Osmolality, and Osmolarity", "Remington's Pharmaceutical Sciences", ed. A.R. Gennaro, 17th ed., Mack Publishing Company, Easton, Pa. (1985), Chapter 80, p. 1455-1472.
Giles, Robert L. et al., "Plastic Packaging Materials", "Remington's Pharmaceutical Sciences", ed. A.R. Gennaro, 17th ed., Mack Publishing Company, Easton, Pa. (1985), Chapter 81, p. 1473-1477.
Lintner, Carl J., "Stability of Pharmaceutical Products", "Remington's Pharmaceutical Sciences", ed. A.R. Gennaro, 17th ed., Mack Publishing Company, Easton, Pa. (1985), Chapter 82, p. 1478-1486.
Erskine, Clyde R., "Quality Assurance and Control", "Remington's Pharmaceutical Sciences", ed. A.R. Gennaro, 17th ed., Mack Publishing Company, Easton, Pa. (1985), Chapter 83, p. 1487-1491.
Nairn, J G., "Sloutions, Emulsions, Suspensions and Extractives", "Remington's Pharmaceutical Sciences", ed. A.R. Gennaro, 17th ed., Mack Publishing Company, Easton, Pa. (1985), Chapter 84, p. 1492-1517.
Avis, Kenneth E., "Parenteral Preparations", "Remington's Pharmaceutical Sciences", ed. A.R. Gennaro, 17th ed., Mack Publishing Company, Easton, Pa. (1985), Chapter 85, p. 1518-1541.
Turco, Salvatore J. et al., "Intravenous Admixtures", "Remington's Pharmaceutical Sciences", ed. A.R. Gennaro, 17th ed., Mack Publishing Company, Easton, Pa. (1985), Chapter 86, p. 1542-1552.
Mullins, John, D., "Ophthalmic Preparations", "Remington's Pharmaceutical Sciences", ed. A.R. Gennaro, 17th ed., Mack Publishing Company, Easton, Pa. (1985), Chapter 87, p. 1553-1566.
Block, Lawrence H., "Medicated Applications", "Remington's Pharmaceutical Sciences", ed. A.R. Gennaro, 17th ed., Mack Publishing Company, Easton, Pa. (1985), Chapter 88, p. 1567-1584.
Ripple, Edward G., "Powders", "Remington's Pharmaceutical Sciences", ed. A.R. Gennaro, 17th ed., Mack Publishing Company, Easton, Pa. (1985), Chapter 89, p. 1585-1602.
King, Robert E. et al., "Oral Solid Dosage Forms", "Remington's Pharmaceutical Sciences", ed. A.R. Gennaro, 17th ed., Mack Publishing Company, Easton, Pa. (1985), Chapter 90, p. 1603-1632.
Porter, Stuart C., "Coating of Pharmaceutical Dosage Forms", "Remington's Pharmaceutical Sciences", ed. A.R. Gennaro, 17th ed., Mack Publishing Company, Easton, Pa. (1985), Chapter 91, p. 1633-1643.
Longer, Mark A., "Sustained-Release Drug Delivery Systems", "Remington's Pharmaceutical Sciences", ed. A.R. Gennaro, 17th ed., Mack Publishing Company, Easton, Pa. (1985), Chapter 92, p. 1644-1661.
Sciarra, John J., "Aerosols", "Remington's Pharmaceutical Sciences", ed. A.R. Gennaro, 17th ed., Mack Publishing Company, Easton, Pa. (1985), Chapter 93, p. 1662-1677.
Chiang C., "Formulation development of an oral dosage form for an hiv protease inhibitor, AG1284", International journal of pharmaceutics 117 (1995) 197-207.
Wermuth C.G., "Molecular variations based on isosteric replacements", the Practice of Medicinal Chemistry (1996).

* cited by examiner

HETEROQUINOLINE-3-CARBOXAMIDES AS KCNQ2/3 MODULATORS

This application claims priority of U.S. Provisional Patent Application No. 61/730,542, filed on Nov. 28, 2012, and European Patent Application No. 12007990.0, filed on Nov. 28, 2012, the entire contents of which patent applications are incorporated herein by reference.

The invention relates to substituted heteroquinoline-3-carboxamides, to pharmaceutical compositions containing these compounds and also to these compounds for use in the treatment and/or prophylaxis of pain and further diseases and/or disorders.

The treatment of pain, in particular of neuropathic pain, is of great importance in medicine. There is a worldwide need for effective pain therapies. The urgent need for action for a target-orientated treatment of chronic and non-chronic states of pain appropriate for the patient, by which is to be understood the successful and satisfactory treatment of pain for the patient, is also documented in the large number of scientific works which have recently been published in the field of applied analgesics and of fundamental research into nociception.

A pathophysiological feature of chronic pain is the over-excitability of neurons. Neuronal excitability is influenced decisively by the activity of $K^+$ channels, since these determine decisively the resting membrane potential of the cell and therefore the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36).

It has accordingly been possible to detect an analgesic activity in preclinical neuropathy and inflammatory pain models for the KCNQ2/3 agonist retigabine (Blackburn-Munro and Jensen, Eur J. Pharmacol. 2003; 460(2-3); 109-16; post et al., Naunyn Schmiedebergs Arch Pharmacol 2004; 369(4): 382-390).

The KCNQ2/3 $K^+$ channel thus represents a suitable starting point for the treatment of pain; in particular of pain selected from the group consisting of chronic pain, acute pain, neuropathic pain, inflammatory pain, visceral pain and muscular pain (Nielsen et al., Eur J. Pharmacol. 2004; 487(I-3): 93-103), in particular of neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(I-3): 77-88), mania/bipolar disorders (Dencker et al., Epilepsy Behav 2008, 12(1): 49-53) and dystonia-associated dyskinesias (Richter et al., Br J Pharmacol 2006, 149(6): 747-53).

Substituted compounds that have an affinity for the KCNQ2/3 $K^+$ channel are e.g. known from the prior art (WO 2008/046582, WO 2010/046108). In particular, certain quinoline-3-carboxamides have been described for KCNQ modulation (WO 2010/102811, WO 2012/025236, WO 2012/025237, WO 2012/025238).

There is a demand for further compounds having comparable or better properties, not only with regard to affinity to KCNQ2/3 $K^+$ channels per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example. A weak or non-existent interaction with transporter molecules, which are involved in the ingestion and the excretion of pharmaceutical compositions, is also to be regarded as an indication of improved bioavailability and at most low interactions of pharmaceutical compositions. Furthermore, the interactions with the enzymes involved in the decomposition and the excretion of pharmaceutical compositions should also be as low as possible, as such test results also suggest that at most low interactions, or no interactions at all, of pharmaceutical compositions are to be expected.

In addition, it may be advantageous if the compounds show a high selectivity towards other receptors of the KCNQ family (specificity), e.g. towards KCNQ1, KCNQ3/5 or KCNQ4. A high selectivity may have a positive effect on the side effects profile: for example it is known that compounds which (also) have an affinity to KCNQ1 are likely to have a potential for cardial side effects. Therefore, a high selectivity towards KCNQ1 may be desirable. However, it may also be advantageous for the compounds to show a high selectivity towards other receptors. For instance, it may be advantageous for the compounds to show a low affinity for the hERG ion channel or the L-type calcium ion channel (phenylalkylamine-, benzothiazepin-, dihydropyridine-binding site) since these receptors are known to possibly have a potential for cardial side effects. Further, an improved selectivity towards binding to other endogenic proteins (i.e. receptors or enzymes) may result in a better side effects profile and, consequently to an improved tolerance.

It was therefore an object of the invention to provide new compounds having advantages over the compounds of the prior art. These compounds should be suitable in particular as pharmacological active ingredients in pharmaceutical compositions, preferably in pharmaceutical compositions for the treatment and/or prophylaxis of disorders and/or diseases which are mediated, at least in part, by KCNQ2/3 $K^+$ channels.

That object is achieved by the subject-matter described hereinbelow.

It has been found, surprisingly, that substituted compounds of the general formula (I) given below are suitable for the treatment of pain. It has also been found, surprisingly, that substituted compounds of the general formula (I) given below also have an excellent affinity for the KCNQ2/3 $K^+$ channel and are therefore suitable for the prophylaxis and/or treatment of disorders and/or diseases that are mediated at least in part by KCNQ2/3 $K^+$ channels. The substituted compounds thereby act as modulators, i.e. agonists or antagonists, of the KCNQ2/3 $K^+$ channel.

In a first aspect, the present invention therefore relates to a compound of general formula (I),

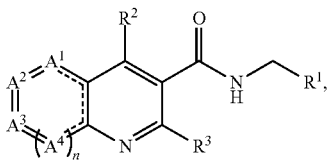

(I)

wherein
$A^1$, $A^2$ and $A^3$ independently of each other represent $CR^4$, N, O, S or $N(CH_3)$,
$A^4$ represents $CR^4$ or N, and
n denotes 0 or 1,
with the proviso, that
at least one of $A^1$, $A^2$, $A^3$ and $A^4$ does not represent $CR^4$,
and with the proviso, that
if n denotes 0, then precisely one of $A^1$, $A^2$ and $A^3$ represents O, S or $N(CH_3)$, or
if n denotes 1, then $A^1$, $A^2$ and $A^3$ independently of each other represent $CR^4$ or N,
$R^1$ represents
  $C_{1-10}$-aliphatic residue, unsubstituted or mono- or polysubstituted;
  $C_{3-10}$-cycloaliphatic residue or 3 to 10 membered heterocycloaliphatic residue, in each case unsubstituted or mono- or polysubstituted and in each case optionally linked via a $C_{1-8}$-aliphatic group, which in turn may be unsubstituted or mono- or polysubstituted;
  aryl or heteroaryl, in each case unsubstituted or mono- or polysubstituted and in each case optionally linked via a $C_{1-8}$-aliphatic group, which in turn may be unsubstituted or mono- or poly-substituted;
$R^2$ represents F; Cl; Br; I; CN; $CF_3$; C(=O)H; $NO_2$; $OCF_3$; $SCF_3$; $C_{1-4}$-aliphatic residue, C(=O)—$C_{1-4}$-aliphatic residue, C(=O)—O—$C_{1-4}$-aliphatic residue, C(=O)—NH—$C_{1-4}$-aliphatic residue, C(=O)—N($C_{1-4}$-aliphatic residue)$_2$, O—$C_{1-4}$-aliphatic residue, O—C(=O)—$C_{1-4}$-aliphatic residue, S—$C_{1-4}$-aliphatic residue, S(=O)$_2$—$C_{1-4}$-aliphatic residue, S(=O)$_2$—O—$C_{1-4}$-aliphatic residue,
  wherein the $C_{1-4}$-aliphatic residue may be in each case be unsubstituted or mono- or polysubstituted;
  $C_{3-6}$-cycloaliphatic residue or 3 to 7 membered heterocycloaliphatic residue, in each case unsubstituted or mono- or polysubstituted and in each case optionally linked via a $C_{1-4}$-aliphatic group, which in turn may be unsubstituted or mono- or polysubstituted;
$R^3$ represents
  $C_{2-10}$-aliphatic residue, unsubstituted or mono- or polysubstituted; or
  $C_{3-10}$-cycloaliphatic residue or 3 to 10 membered heterocycloaliphatic residue, in each case unsubstituted or mono- or polysubstituted and in each case optionally linked via a $C_{1-8}$-aliphatic group, which in turn may be unsubstituted or mono- or polysubstituted,
  or
  denotes S—$R^5$, O—$R^6$ or $N(R^7R^8)$,
  wherein
  $R^5$ and $R^6$ in each case represent
    $C_{1-10}$-aliphatic residue, unsubstituted or mono- or polysubstituted;
    $C_{3-10}$-cycloaliphatic residue or 3 to 10 membered heterocycloaliphatic residue, in each case unsubstituted or mono- or polysubstituted and in each case optionally linked via a $C_{1-8}$-aliphatic group, which in turn may be unsubstituted or mono- or polysubstituted;
    with the proviso, that if $R^5$ or $R^6$ denote a 3 to 10 membered heterocycloaliphatic residue, than the 3 to 10 membered heterocycloaliphatic residue is linked via a carbon atom,
  $R^7$ represents
    $C_{1-10}$-aliphatic residue, unsubstituted or mono- or polysubstituted;
    $C_{3-10}$-cycloaliphatic residue or 3 to 10 membered heterocycloaliphatic residue, in each case unsubstituted or mono- or polysubstituted and in each case optionally linked via a $C_{1-8}$-aliphatic group, which in turn may be unsubstituted or mono- or polysubstituted;
    with the proviso that if $R^7$ denotes 3 to 10 membered heterocycloaliphatic residue, the 3 to 10 membered heterocycloaliphatic residue is linked via a carbon atom; and
  $R^8$ denotes $C_{1-10}$-aliphatic residue, unsubstituted or mono- or polysubstituted;
  or
  $R^7$ and $R^8$ form together with the nitrogen atom connecting them a 3 to 10 membered heterocycloaliphatic residue, unsubstituted or mono- or polysubstituted;
  and each $R^4$ independently represents H, F; Cl; Br; I; CN; $CF_3$; $CHF_2$; $CH_2F$; $OCF_3$; $OCHF_2$; $OCH_2F$; $SCF_3$; O—$C_{1-4}$-aliphatic residue, $C_{1-4}$-aliphatic residue or S(=O)$_2$—$C_{1-4}$-aliphatic residue;
in which an "aliphatic group" and "aliphatic residue" may in each case be branched or unbranched, saturated or unsaturated,
in which a "cycloaliphatic residue" and a "heterocycloaliphatic residue" may in each case be saturated or unsaturated,
in which "mono- or polysubstituted" with respect to an "aliphatic group", an "aliphatic residue", a "cycloaliphatic residue" and a "heterocycloaliphatic residue" relates, with respect to the corresponding residues or groups, to the substitution of one or more hydrogen atoms each independently of one another by at least one substituent selected from the group consisting of F, Cl, Br, I, $NO_2$, $NH_2$, NH($C_{1-4}$-aliphatic residue), N($C_{1-4}$-aliphatic residue)$_2$, NH—C(=O)—$C_{1-4}$ aliphatic residue, N($C_{1-4}$ aliphatic residue)-C(=O)—$C_{1-4}$ aliphatic residue, NH—S(=O)$_2$—$C_{1-4}$ aliphatic residue, N($C_{1-4}$ aliphatic residue)-S(=O)$_2$—$C_{1-4}$ aliphatic residue, =O, OH, $OCF_3$, O—$C_{1-4}$-aliphatic residue, O—C(=O)—$C_{1-4}$-aliphatic residue, SH, $SCF_3$, aliphatic residue, S(=O)$_2$OH, S(=O)$_2$—$C_{1-4}$-aliphatic residue, S(=O)$_2$—O—$C_{1-4}$-aliphatic residue, S(=O)$_2$—NH($C_{1-4}$-aliphatic residue), S(=O)$_2$—N($C_{1-4}$-aliphatic residue)$_2$, CN, $CF_3$, CHO, COOH, $C_{1-4}$-aliphatic residue, C(=O)—$C_{1-4}$-aliphatic residue, C(=O)—O—$C_{1-4}$-aliphatic residue, $C_{3-6}$-cycloaliphatic residue, 3 to 7 membered heterocycloaliphatic residue, C(=O)$NH_2$, a C(=O)—NH($C_{1-4}$-aliphatic residue) and C(=O)—N($C_{1-4}$-aliphatic residue)$_2$;
in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, $NO_2$, $NH_2$,

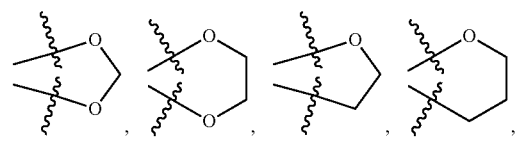

NH(C$_{1-4}$-aliphatic residue), N(C$_{1-4}$-aliphatic residue)$_2$, NH—C(=O)—C$_{1-4}$-aliphatic residue, N(C$_{1-4}$aliphatic residue)-C(=O)—C$_{1-4}$aliphatic residue, NH—S(=O)$_2$—C$_{1-4}$ aliphatic residue, N(C$_{1-4}$aliphatic residue)-S(=O)$_2$—C$_{1-4}$ aliphatic residue, OH, OCF$_3$, O—C$_{1-4}$-aliphatic residue, O—C(=O)—C$_{1-4}$-aliphatic residue, SH, SCF$_3$, S—C$_{1-4}$-aliphatic residue, S(=O)$_2$OH, S(=O)$_2$—C$_{1-4}$-aliphatic residue, S(=O)$_2$—O—C$_{1-4}$-aliphatic residue, S(=O)$_2$—NH (C$_{1-4}$-aliphatic residue), S(=O)$_2$—N(C$_{1-4}$-aliphatic residue)$_2$, CN, CF$_3$, C(=O)H, C(=O)OH, C$_{1-4}$-aliphatic residue, C(=O)—C$_{1-4}$-aliphatic residue, C(=O)—O—C$_{1-4}$-aliphatic residue, C$_{3-6}$-cycloaliphatic residue, 3 to 7 membered heterocycloaliphatic residue, benzyl, aryl, heteroaryl, C(=O)NH$_2$, C(=O)—NH(C$_{1-4}$-aliphatic residue) and C(=O)—N(C$_{1-4}$-aliphatic residue)$_2$;
in the form of an individual single stereoisomer or a mixture of the stereoisomers in any mixing ratio, and/or in the form of a free compound, a solvate and/or a physiologically acceptable salt.

Within the scope of this invention, the terms "aliphatic residue" or "aliphatic group" include acyclic saturated or unsaturated aliphatic hydrocarbon radicals, which can be branched or unbranched as well as unsubstituted or mono- or poly-substituted, having from 1 to 10 or from 1 to 8 or from 1 to 6 or from 1 to 4 or from 1 to 2 or from 2 to 6 carbon atoms, that is to say C$_{1-10}$-alkanyls, C$_{2-10}$-alkenyls and C$_{2-10}$-alkynyls or C$_{1-8}$-alkanyls, C$_{2-8}$-alkenyls and C$_{2-8}$-alkynyls or C$_{1-6}$-alkanyls, C$_{2-6}$-alkenyls and C$_{2-6}$-alkynyls or C$_{1-4}$-alkanyls, C$_{2-4}$-alkenyls and C$_{2-4}$-alkynyls or C$_{1-2}$-alkanyls, C$_2$-alkenyls and C$_2$-alkynyls or C$_{2-6}$-alkanyls, C$_{2-6}$-alkenyls and C$_{2-6}$-alkynyls. Alkenyls contain at least one C—C double bond and alkynyls contain at least one C—C triple bond. Alkyl is preferably selected from the group comprising methyl, ethyl, n-propyl, 2-propyl, n-butyl, isobutyl, sec-butyl, tert-butyl, n-pentyl, isopentyl, neopentyl, n-hexyl, n-heptyl, n-octyl, n-nonyl, n-decyl, ethenyl(vinyl), ethynyl, propenyl, propynyl, butenyl, butynyl, pentenyl, pentynyl, hexenyl and hexynyl, heptenyl, heptynyl, octenyl, octynyl, nonenyl, nonynyl, decenyl and decynyl.

For the purposes of this invention, the terms "cycloaliphatic residue" or "C$_{3-10}$-cycloaliphatic residue" and "C$_{3-6}$-cycloaliphatic residue" denote cyclic aliphatic hydrocarbons having 3, 4, 5, 6, 7, 8, 9 or 10 carbon atoms or having 3, 4, 5 or 6 carbon atoms, wherein the hydrocarbons can be saturated or unsaturated (but not aromatic), unsubstituted or mono- or poly-substituted. The bonding of the cycloaliphatic residue to the general structure of higher order can take place via any desired and possible ring member of the cycloalkyl radical. The cycloaliphatic residue can also be fused with further saturated, (partially) unsaturated, (hetero) cycloaliphatic, aromatic or heteroaromatic ring systems, that is to say with cycloaliphatic residue, heterocycloaliphatic residue, aryl or heteroaryl, which can themselves be unsubstituted or mono- or poly-substituted. The cycloaliphatic residue radicals can further be bridged one or more times, as, for example, in the case of adamantyl, bicyclo[2.2.1]heptyl or bicyclo[2.2.2]octyl. Cycloalkyl is preferably selected from the group comprising cyclopropyl, cyclobutyl, cyclopentyl, cyclopentenyl, cyclohexyl, cyclohexenyl, cycloheptyl, cycloheptenyl, cyclooctyl, cyclooctenyl cyclononyl, cyclodecyl, adamantyl as well as

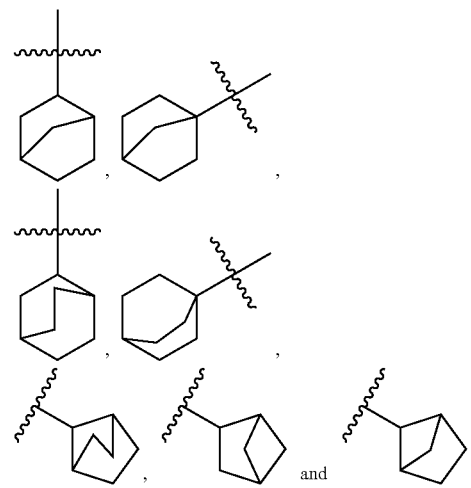

Preferred C$_{3-6}$-cycloaliphatic residues are selected from the group consisting of cyclopropyl, cyclobutyl, cyclopentyl, cyclohexyl, cyclopentenyl and cyclohexenyl.

The term "3 to 10 membered heterocycloaliphatic residue" or "3 to 7 membered heterocycloaliphatic residue" or "heterocycloaliphatic residue" includes aliphatic saturated or unsaturated (but not aromatic) heterocycloaliphatic residues having preferentially from three to ten, that is to say 3, 4, 5, 6, 7, 8, 9 or 10, ring members or from three to seven, that is to say 3, 4, 5, 6 or 7, ring members in which at least one carbon atom, optionally also two or three carbon atoms, has been replaced by a heteroatom or heteroatom group in each case selected independently of one another from the group consisting of O, S, S(=O), S(=O)$_2$, N, NH and N(C$_{1-8}$-alkyl), preferably N(CH$_3$), wherein the ring members can be unsubstituted or mono- or poly-substituted. The bonding of the heterocycloaliphatic residue to the general structure of higher order can take place via any desired and possible ring member of the heterocycloaliphatic residue. The heterocycloaliphatic residues can also be fused with further saturated, (partially) unsaturated (hetero)cycloaliphatic or aromatic or heteroaromatic ring systems, that is to say with cycloaliphatic residue, heterocycloaliphatic residue, aryl or heteroaryl, which can themselves be unsubstituted or mono- or poly-substituted. Heterocycloaliphatic residues are preferably selected from the group comprising azetidinyl, aziridinyl, azepanyl, azocanyl, diazepanyl, dithiolanyl, dihydroquinolinyl, dihydropyrrolyl, dioxanyl, dioxolanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl.

Within the scope of this invention, the term "aryl" denotes aromatic hydrocarbons having up to 14 ring members, inter alia phenyls and naphthyls. Each aryl radical can be unsubstituted or mono- or poly-substituted, it being possible for the aryl substituents to be identical or different and to be in any desired and possible position of the aryl. The aryl can be bonded to the general structure of higher order via any desired and possible ring member of the aryl radical. The aryl radicals can also be fused with further saturated, (partially) unsaturated, (hetero)cycloaliphatic, aromatic or heteroaromatic ring systems, that is to say with cycloaliphatic residue, heterocycloaliphatic residue, aryl or heteroaryl, which can themselves be unsubstituted or mono- or poly-substituted. Examples of fused aryl radicals are benzodioxolanyl and benzodioxanyl. Aryl is preferably selected from the group containing phenyl, 1-naphthyl and 2-naphthyl, each of which can be unsubstituted or mono- or poly-substituted. A particularly preferred aryl is phenyl, unsubstituted or mono- or poly-substituted.

The term "heteroaryl" denotes a 5- or 6-membered cyclic aromatic radical which contains at least 1 heteroatom, optionally also 2, 3, 4 or 5 heteroatoms, wherein the heteroatoms are in each case selected independently of one another from the group S, N and O and the heteroaryl radical can be unsubstituted or mono- or poly-substituted; in the case of substitution on the heteroaryl, the substituents can be identical or different and can be in any desired and possible position of the heteroaryl. Bonding to the general structure of higher order can take place via any desired and possible ring member of the heteroaryl radical. The heteroaryl can also be part of a bi- or poly-cyclic system having up to 14 ring members, wherein the ring system can be formed with further saturated, (partially) unsaturated, (hetero)-cycloaliphatic residue or aromatic or heteroaromatic rings, that is to say with cycloaliphatic residue, heterocycloaliphatic residue, aryl or heteroaryl, which can themselves be unsubstituted or mono- or poly-substituted. It is preferred for the heteroaryl radical to be selected from the group comprising benzo-furanyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl(furanyl), imidazolyl, imidazothiazolyl, indazolyl, indolizinyl, indolyl, isoquinolinyl, isoxazolyl, isothiazolyl, indolyl, naphthyridinyl, oxazolyl, oxadiazolyl, phenazinyl, phenothiazinyl, phthalazinyl, pyrazolyl, pyridyl(2-pyridyl, 3-pyridyl, 4-pyridyl), pyrrolyl, pyridazinyl, pyrimidinyl, pyrazinyl, purinyl, phenazinyl, thienyl(thiophenyl), triazolyl, tetrazolyl, thiazolyl, thiadiazolyl and triazinyl. Furyl, pyridyl and thienyl are particularly preferred.

Within the scope of the invention, the expressions "linked via $C_{1-4}$-aliphatic group" or "linked via a $C_{1-8}$-aliphatic group" in relation to aryl, heteroaryl, heterocycloaliphatic residue or cycloaliphatic residue is understood that $C_{1-8}$-aliphatic group or $C_{1-4}$-aliphatic group and aryl or heteroaryl or heterocycloaliphatic residue or cycloaliphatic residue have the meanings defined above and the aryl or heteroaryl or heterocycloaliphatic residue or cycloaliphatic residue is bonded to the general structure of higher order via a $C_{1-4}$-aliphatic group or via a $C_{1-8}$-aliphatic group. The aliphatic group can in all cases be saturated or unsaturated, branched or unbranched, unsubstituted or mono- or poly-substituted. The $C_{1-4}$-aliphatic group is preferably selected from $C_{1-4}$-alkyl groups, preferably from the group comprising of —CH$_2$—, —CH$_2$CH$_2$—, —CH(CH$_3$)—, —CH$_2$CH$_2$CH$_2$—, —CH(CH$_3$)CH$_2$—, —CH(CH$_2$CH$_3$)—, —CH$_2$(CH$_2$)$_2$CH$_2$—, —CH(CH$_3$)CH$_2$CH$_2$—, —CH$_2$CH(CH$_3$)CH$_2$—, —CH(CH$_3$)CH(CH$_3$)—, —CH(CH$_2$CH$_3$)CH$_2$—, —C(CH$_3$)$_2$CH$_2$—, —CH(CH$_2$CH$_2$CH$_3$)—, —C(CH$_3$)(CH$_2$CH$_3$)—, —CH=CH—, —CH=CHCH$_2$—, —C(CH$_3$)=CH$_2$—, —CH=CHCH$_2$CH$_2$—, —CH$_2$CH=CHCH$_2$—, —CH=CHCH=CH—, —C(CH$_3$)=CHCH$_2$—, —CH=C(CH$_3$)CH$_2$—, —C(CH$_3$)=C(CH$_3$)—, —C(CH$_2$CH$_3$)=CH—, —C≡C—, —C≡CCH$_2$—, —C≡CCH$_2$CH$_2$—, —C≡CCH(CH$_3$)—, —CH$_2$C≡CCH$_2$— and —C≡CC(CH$_3$)$_2$—.

In relation with "aliphatic residue", "aliphatic group", "heterocycloaliphatic residue" and "cycloaliphatic residue", the expression "mono- or poly-substituted" is understood as meaning within the scope of this invention the substitution of one or more hydrogen atoms one or more times, for example two, three or four times, in each case independently of one another, by substituents selected from the group comprising F, Cl, Br, I, NO$_2$, NH$_2$, NH(C$_{1-4}$-aliphatic residue), N(C$_{1-4}$-aliphatic residue)$_2$, NH—C(=O)—C$_{1-4}$ aliphatic residue, N(C$_{1-4}$-aliphatic residue)-C(=O)—C$_{1-4}$ aliphatic residue, NH—S(=O)$_2$—C$_{1-4}$-aliphatic residue, N(C$_{1-4}$-aliphatic residue)-S(=O)$_2$—C$_{1-4}$-aliphatic residue, =O, OH, OCF$_3$, O—C$_{1-4}$-aliphatic residue, O—C(=O)—C$_{1-4}$-aliphatic residue, SH, SCF$_3$, S—C$_{1-4}$-aliphatic residue, S(=O)$_2$OH, S(=O)$_2$—C$_{1-4}$-aliphatic residue, S(=O)$_2$—O—C$_{1-4}$-aliphatic residue, S(=O)$_2$—NH(C$_{1-4}$-aliphatic residue), S(=O)$_2$—N(C$_{1-4}$-aliphatic residue)$_2$, CN, CF$_3$, CHO, COOH, C$_{1-4}$-aliphatic residue, C(=O)—C$_{1-4}$-aliphatic residue, C(=O)—O—C$_{1-4}$-aliphatic residue, C$_{3-6}$-cycloaliphatic residue, 3 to 7 membered heterocycloaliphatic residue, benzyl, aryl, heteroaryl, C(=O)NH$_2$, a C(=O)—NH(C$_{1-4}$-aliphatic residue) and C(=O)—N(C$_{1-4}$-aliphatic residue)$_2$; wherein polysubstituted radicals are to be understood as being radicals that are substituted several times, for example two, three or four times, either on different atoms or on the same atom, for example three times on the same carbon atom, as in the case of CF$_3$ or CH$_2$CF$_3$, or at different places, as in the case of CH(OH)—CH=CH—CHCl$_2$. A substituent can itself optionally be mono- or poly-substituted. Polysubstitution can take place with the same or with different substituents.

Preferred substituents of "aliphatic residue", "aliphatic group", "heterocycloaliphatic residue" or "cycloaliphatic residue" are selected from the group comprising F, Cl, Br, NH$_2$, NH(C$_{1-4}$-aliphatic residue), N(C$_{1-4}$-aliphatic residue)$_2$, NH—C(=O)—C$_{1-4}$aliphatic residue, NH—S(=O)$_2$—C$_{1-4}$-aliphatic residue, =O, OH, OCF$_3$, O—C$_{1-4}$-aliphatic residue, O—C(=O)—C$_{1-4}$-aliphatic residue, S(=O)$_2$—C$_{1-4}$-aliphatic residue, S(=O)$_2$—NH(C$_{1-4}$-aliphatic residue), S(=O)$_2$—N(C$_{1-4}$-aliphatic residue)$_2$, CN, CF$_3$, COOH, C$_{1-4}$-aliphatic residue, C(=O)—C$_{1-4}$-aliphatic residue, C$_{3-6}$-cycloaliphatic residue, 3 to 7 membered heterocycloaliphatic residue, C(=O)NH$_2$, C(=O)—NH(C$_{1-4}$-aliphatic residue) and C(=O)—N(C$_{1-4}$-aliphatic residue)$_2$.

In relation with "aryl" and "heteroaryl", the term "mono- or poly-substituted" is understood within the scope of this invention as meaning the substitution of one or more hydrogen atoms of the ring system one or more times, for example two, three or four times, in each case independently of one another, by substituents selected from the group comprising F, Cl, Br, I, NO$_2$, NH$_2$,

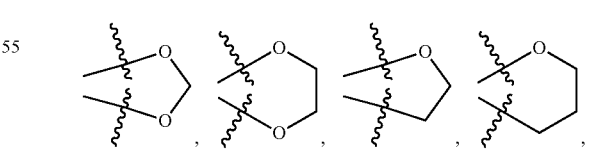

NH(C$_{1-4}$-aliphatic residue), N(C$_{1-4}$-aliphatic residue)$_2$, NH—C(=O)—C$_{1-4}$-aliphatic residue, N(C$_{1-4}$-aliphatic residue)-C(=O)—C$_{1-4}$-aliphatic residue, NH—S(=O)$_2$—C$_{1-4}$-aliphatic residue, N(C$_{1-4}$aliphatic residue)-S(=O)$_2$—C$_{1-4}$-aliphatic residue, OH, OCF$_3$, O—C$_{1-4}$-aliphatic residue, O—C(=O)—C$_{1-4}$-aliphatic residue, SH, SCF$_3$, S—C$_{1-4}$-aliphatic residue, S(=O)$_2$OH, S(=O)$_2$—C$_{1-4}$-aliphatic residue, $S(=O)_2$—O—$C_{1\text{-}4}$-aliphatic residue, $S(=O)_2$—NH ($C_{1\text{-}4}$-aliphatic residue), $S(=O)_2$—N($C_{1\text{-}4}$-aliphatic residue)$_2$, CN, $CF_3$, $C(=O)$H, $C(=O)$OH, $C_{1\text{-}4}$-aliphatic residue, $C(=O)$—$C_{1\text{-}4}$-aliphatic residue, $C(=O)$—O—$C_{1\text{-}4}$-aliphatic residue, $C_{3\text{-}6}$-cycloaliphatic residue, 3 to 7 membered heterocycloaliphatic residue, benzyl, aryl, heteroaryl, $C(=O)NH_2$, $C(=O)$—NH($C_{1\text{-}4}$-aliphatic residue) and $C(=O)$—N($C_{1\text{-}4}$-aliphatic residue)$_2$; on one atom or optionally on different atoms, wherein a substituent can itself optionally be mono- or poly-substituted. Polysubstitution is carried out with the same or with different substituents.

Preferred "aryl" and "heteroaryl" substituents are F; Cl; Br; $CF_3$; CN; $C_{1\text{-}4}$-aliphatic residue; phenyl; naphthyl; pyridyl; thienyl; furyl; $C_{3\text{-}6}$-cycloaliphatic residue; 3 to 7 membered heterocycloaliphatic residue; $C(=O)$—$C_{1\text{-}4}$-aliphatic residue; $CC_2H$; $C(=O)$—O—$C_{1\text{-}4}$-aliphatic residue; $CONH_2$; $C(=O)$—NH($C_{1\text{-}4}$-aliphatic residue); $C(=O)$—N($C_{1\text{-}4}$-aliphatic residue)$_2$; OH; O—$C_{1\text{-}4}$-aliphatic residue; $OCF_3$; O—C$(=O)$—$C_{1\text{-}4}$-aliphatic residue; $NH_2$; NH($C_{1\text{-}4}$-aliphatic residue); N($C_{1\text{-}4}$-aliphatic residue)$_2$; N(H)C$(=O)$—$C_{1\text{-}4}$-aliphatic residue; S—$C_{1\text{-}8}$-alkyl; $SCF_3$; $S(=O)_2$ $C_{1\text{-}4}$-aliphatic residue; $S(=O)_2$—N(H)$C_{1\text{-}4}$-aliphatic residue.

The compounds according to the invention are defined by substituents, for example by $R^A$, $R^B$ and $R^C$ (1st generation substituents), which are themselves optionally substituted (2nd generation substituents). Depending on the definition, these substituents of the substituents can in turn themselves be substituted (3rd generation substituents). If, for example, $R^A$=aryl (1st generation substituent), aryl can itself be substituted, for example by $C_{1\text{-}4}$-aliphatic residue (2nd generation substituent). This yields the functional group aryl-$C_{1\text{-}4}$-aliphatic residue. $C_{1\text{-}4}$-aliphatic residue can then in turn itself be substituted, for example by Cl (3rd generation substituent). Overall, this then yields the functional group aryl-$C_{1\text{-}4}$-aliphatic residue-Cl.

In a preferred embodiment, however, the 3rd generation substituents cannot themselves be substituted, that is to say there are no 4th generation substituents.

In another preferred embodiment, the 2nd generation substituents cannot themselves be substituted, that is to say there are not even any 3rd generation substituents. In other words, in this embodiment, for example in the case of the general formula (I), the functional groups for $R^1$ to $R^{14}$ can in each case optionally be substituted, but the substituents in each case cannot themselves be substituted.

In some cases, the compounds according to the invention are defined by substituents which are or carry an aryl or heteroaryl radical, in each case unsubstituted or mono- or poly-substituted, or which, together with the carbon atom(s) or heteroatom(s) joining them as ring member(s), form a ring, for example an aryl or heteroaryl, in each case unsubstituted or mono- or poly-substituted. Both these aryl or heteroaryl radicals and the aromatic ring systems so formed can optionally be fused with $C_{3\text{-}10}$-cycloaliphatic residue or heterocycloaliphatic residue, in each case saturated or unsaturated, that is to say with a $C_{3\text{-}10}$-cycloaliphatic residue such as cyclopentyl or with a heterocycloaliphatic residue such as morpholinyl, it being possible for the $C_{3\text{-}10}$-cycloaliphatic residue or heterocycloaliphatic residue radicals so fused to be unsubstituted or mono- or poly-substituted.

In some cases, the compounds according to the invention are defined by substituents which are or carry a $C_{3\text{-}10}$-heterocycloaliphatic residue or heterocycloaliphatic residue, in each case unsubstituted or mono- or poly-substituted, or which, together with the carbon atom(s) or heteroatom(s) joining them as ring member(s), form a ring, for example a $C_{3\text{-}10}$-cycloaliphatic residue or heterocycloaliphatic residue, in each case unsubstituted or mono- or poly-substituted. Both these $C_{3\text{-}10}$-cycloaliphatic or heterocycloaliphatic residue and the aliphatic ring systems formed can optionally be fused with aryl or heteroaryl, that is to say with an aryl such as phenyl or with a heteroaryl such as pyridyl, it being possible for the aryl or heteroaryl radicals so fused to be unsubstituted or mono- or poly-substituted.

Within the scope of the present invention, the symbol

used in formulae denotes a linking of a corresponding radical to the general structure of higher order.

The expression "salt formed with a physiologically acceptable acid" is understood within the scope of this invention as meaning salts of the active ingredient in question with inorganic or organic acids that are physiologically acceptable—in particular when used in humans and/or mammals. The hydrochloride is particularly preferred.

Physiologically acceptable salts with cations or bases are salts of the compound in question—in the form of the anion with at least one, preferably inorganic—cation that are physiologically acceptable—in particular when used in humans and/or mammals.

In one embodiment of present invention, the compound according to general formula (I), is characterized in that
$A^1$, $A^2$ and $A^3$ independently of each other represent $CR^4$, N, O, S or N($CH_3$),
$A^4$ represents $CR^4$ or N, and
n denotes 0 or 1,
with the proviso, that
at least one of $A^1$, $A^2$, $A^3$ and $A^4$ does not represent $CR^4$,
and with the proviso, that
if n denotes 0, then precisely one of $A^1$, $A^2$ and $A^3$ represents O, S or N($CH_3$), or
if n denotes 1, then $A^1$, $A^2$ and $A^3$ independently of each other represent $CR^4$ or N,
$R^1$ denotes $C_{1\text{-}10}$-aliphatic residue, unsubstituted or mono- or polysubstituted with at least one substituent selected from the group consisting of F, Cl, Br, I, $NO_2$, $NH_2$, NH($C_{1\text{-}4}$-aliphatic residue), N($C_{1\text{-}4}$-aliphatic residue)$_2$, OH, =O, O—$C_{1\text{-}4}$-aliphatic residue, $OCF_3$, SH, $SCF_3$, S—$C_{1\text{-}4}$-aliphatic residue, $CF_3$, CN, $C_{1\text{-}4}$-aliphatic residue and $C(=O)$OH,
wherein the $C_{1\text{-}4}$-aliphatic residue in each case may be unsubstituted or mono- or polysubstituted with at least one substituent selected from the group consisting of F, Cl, Br, I, OH, $OCF_3$, $CF_3$ and O—$C_{1\text{-}4}$-aliphatic residue,
or denotes $C_{3\text{-}10}$-cycloaliphatic residue or 3 to 10 membered heterocycloaliphatic residue, in each case unsubstituted or mono- or polysubstituted with at least one substituent selected from the group consisting of F, Cl, Br, I, $NO_2$, $NH_2$, NH($C_{1\text{-}4}$-aliphatic residue), N($C_{1\text{-}4}$-aliphatic residue)$_2$, OH, =O, O—$C_{1\text{-}4}$-aliphatic residue, $OCF_3$, SH, $SCF_3$, S—$C_{1\text{-}4}$-aliphatic residue, $CF_3$, CN, $C_{1\text{-}4}$-aliphatic residue, $C(=O)$—OH, $C_{3\text{-}6}$-cycloaliphatic residue and 3 to 7 membered heterocycloaliphatic residue,
wherein the $C_{1\text{-}4}$-aliphatic residue in each case may be unsubstituted or mono- or polysubstituted with at least one substituent selected from the group consisting of F, Cl, Br, I, OH, OCF$_3$, CF$_3$ and O—C$_{1-4}$-aliphatic residue, and wherein the C$_{3-8}$-cycloaliphatic residue and the 3 to 7 membered heterocycloaliphatic residue may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, and wherein the C$_{3-10}$-cycloaliphatic residue or the 3 to 10 membered heterocycloaliphatic residue may in each case optionally linked via a C$_{1-8}$-aliphatic group, which in turn may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, or denotes aryl or heteroaryl, in each case unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)OH, C(=O)CH$_3$, C(=O)C$_2$H$_5$, C(=O)OCH$_3$, C(=O)OC$_2$H$_5$, C$_{3-8}$-cycloaliphatic residue, 3 to 7 membered heterocycloaliphatic residue,

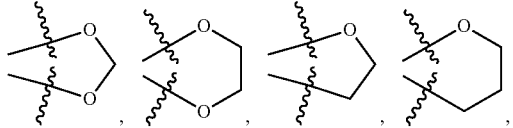

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, O—C$_{1-4}$-aliphatic residue, OCF$_3$, OCH$_2$CH$_2$OH, OCH$_2$OCH$_3$, SH, SCF$_3$, S—C$_{1-4}$-aliphatic residue, CF$_3$, CN, C$_{1-4}$-aliphatic residue, C(=O)OH, C(=O)CH$_3$, C(=O)C$_2$H$_5$, C(=O)OCH$_3$ and C(=O)OC$_2$H$_5$, and wherein the C$_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, and wherein the aryl or the heteroaryl residue may in each case be optionally linked via a C$_{1-8}$-aliphatic group, which in turn may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN and C(=O)OH, R$^2$ represents F; Cl; Br; I; CN; CF$_3$; NO$_2$; OCF$_3$; SCF$_3$; C$_{1-4}$-aliphatic residue, S—C$_{1-4}$-aliphatic residue, O—C$_{1-4}$-aliphatic residue, wherein the C$_{1-4}$-aliphatic residue may be in each case be unsubstituted or mono- or polysubstituted with at least one substituent selected from the group consisting of F, Cl, Br, I, OH, OCF$_3$, CF$_3$ and O—C$_{1-4}$-aliphatic residue, or C$_{3-8}$-cycloaliphatic residue or 3 to 7 membered heterocycloaliphatic residue, in each case unsubstituted or mono- or polysubstituted and in each case optionally linked via a C$_{1-4}$-aliphatic group, which in turn may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN and C(=O)OH, R$^3$ denotes C$_{2-10}$-aliphatic residue, unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and O—C$_{1-4}$-aliphatic residue, or denotes C$_{3-10}$-cycloaliphatic residue or 3 to 10 membered heterocycloaliphatic residue, in each case unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and O—C$_{1-4}$-aliphatic residue, and wherein the C$_{3-10}$-cycloaliphatic residue or the 3 to 10 membered heterocycloaliphatic residue may in each case optionally linked via a C$_{1-8}$-aliphatic group, which in turn may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, or denotes S—R$^5$, O—R$^6$ or N(R$^7$R$^8$), wherein R$^5$ and R$^6$ in each case represent C$_{1-10}$-aliphatic residue, unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and O—C$_{1-4}$-aliphatic residue, or in each case represent $C_{3-10}$-cycloaliphatic residue or 3 to 10 membered heterocycloaliphatic residue, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)—OH, $C_{3-8}$-cycloaliphatic residue and 3 to 7 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-8}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the $C_{3-10}$-cycloaliphatic residue or the 3 to 10 membered heterocycloaliphatic residue may in each case optionally linked via a $C_{1-8}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, on the condition that if $R^5$ or $R^6$ denote a 3 to 10 membered heterocycloaliphatic residue, the 3 to 10 membered heterocycloaliphatic residue is linked via a carbon atom, $R^7$ denotes a $C_{1-10}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)—O—$C_{1-4}$-aliphatic residue and C(=O)OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, C(=O)—O—$C_{1-4}$-aliphatic residue, $C_{3-8}$-cycloaliphatic residue and 3 to 7 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-8}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the $C_{3-10}$-cycloaliphatic residue or the 3 to 10 membered heterocycloaliphatic residue may in each case optionally linked via a $C_{1-8}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, C(=O)—O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, on the condition that if $R^7$ denotes a 3 to 10 membered heterocycloaliphatic residue, the 3 to 10 membered heterocycloaliphatic residue is linked via a carbon atom, and $R^8$ denotes $C_{1-10}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, or $R^7$ and $R^8$ form together with the nitrogen atom connecting them a 3 to 10 membered heterocycloaliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)—OH, $C_{3-8}$-cycloaliphatic residue and 3 to 7 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-8}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the 3 to 10 membered heterocycloaliphatic residue formed by $R^7$ and $R^8$ together with the nitrogen atom connecting them may optionally be condensed with aryl or heteroaryl, wherein the aryl or heteroaryl residues condensed in this way can for their part be respectively unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$ and C(=O)$OC_2H_5$, $C_{3-6}$-cycloaliphatic residue, 3 to 7 membered heterocycloaliphatic residue,

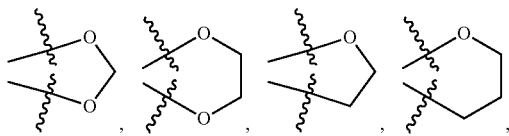

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, $OCH_2CH_2OH$, $OCH_2OCH_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$ and C(=O)$OC_2H_5$, and wherein the $C_{3-6}$ cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)—OH, and each $R^4$ independently represents H, F; Cl; Br; I; CN; $CF_3$; $CHF_2$; $CH_2F$; $OCF_3$; $OCHF_2$; $OCH_2F$; $SCF_3$; O—$C_{1-4}$-aliphatic residue, $C_{1-4}$-aliphatic residue or S(=O)$_2$—$C_{1-4}$-aliphatic residue.

Within the scope of the present invention, the central structural element of general formula (I),

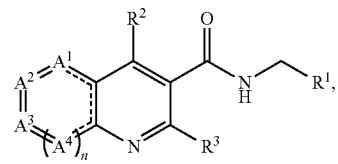

represents a bicyclic [5,6] (for n=0) or a bicyclic [6,6] (for n=1) heteroaryl residue. The heteroaryl residue is aromatic as depicted by the dashed bond presentation.

If n represents 1, then central structural element in general formula (I) represents a a bicyclic [6,6] heteroaryl residue (I-1):

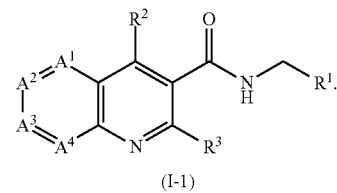

If n represents O, then the partial structure in general formula (I) represents a bicyclic [5,6] heteroaryl residue (I-2) or (I-3) or (I-4):

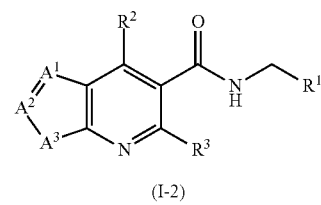

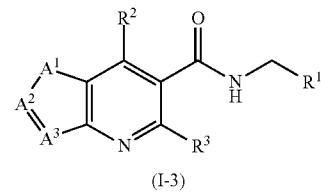

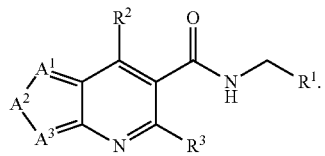

To retain aromaticity of the 5-membered heterocycle, it is understood within the scope of the invention, that, if n denotes 0 and $A^3$ represents O or S or $NR^8$, the compound according to general formula (I) is represented by formula (I-2), that, if n denotes 0 and $A^1$ represents O or S or $NR^8$, the compound according to general formula (I) is represented by formula (I-3), and that, if n denotes 0 and $A^2$ represents O or S or $NR^8$, the compound according to general formula (I) is represented by formula (I-4).

In another embodiment of the invention, the compound according to general formula (I) is characterized in that n denotes 1 and $A^1$ represents N, $A^2$ represents $CR^4$, $A^3$ represents $CR^4$ and $A^4$ represents $CR^4$ (formula (I-1a)),

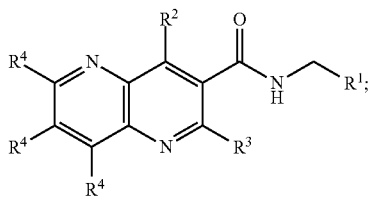

(I-1a)

or n denotes 1 and $A^1$ represents $CR^4$, $A^2$ represents N, $A^3$ represents $CR^4$ and $A^4$ represents $CR^4$ (formula (I-1b)),

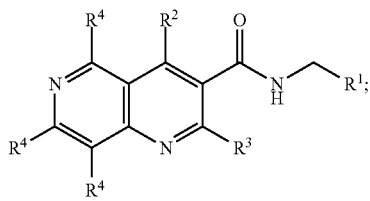

(I-1b)

or n denotes 1 and $A^1$ represents $CR^4$, $A^2$ represents $CR^4$, $A^3$ represents $CR^4$ and $A^4$ represents $CR^4$ (formula (I-1c)),

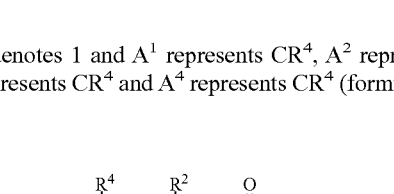

(I-1c)

or n denotes 1 and $A^1$ represents $CR^4$, $A^2$ represents $CR^4$, $A^3$ represents $CR^4$ and $A^4$ represents N (formula (I-1d)),

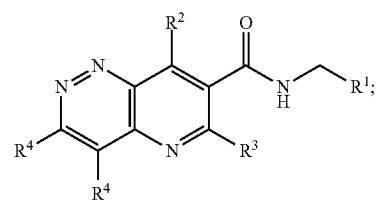

(I-1d)

or n denotes 1 and $A^1$ represents N, $A^2$ represents N, $A^3$ represents $CR^4$ and $A^3$ represents $CR^4$ (formula (I-1e)),

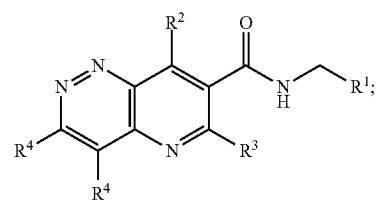

(I-1e)

or n denotes 1 and $A^1$ represents N, $A^2$ represents $CR^4$, $A^3$ represents N and $A^3$ represents $CR^4$ (formula (I-1f)),

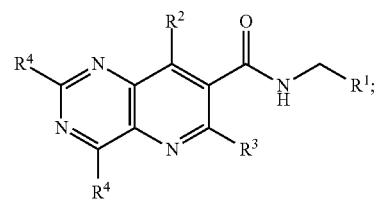

(I-1f)

or n denotes 1 and $A^1$ represents N, $A^2$ represents $CR^4$, $A^3$ represents $CR^4$ and $A^4$ represents N (formula (I-1g)),

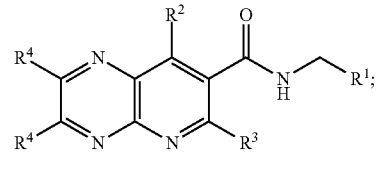

(I-1g)

or n denotes 1 and $A^1$ represents $CR^4$, $A^2$ represents N, $A^3$ represents $CR^4$ and $A^4$ represents N (formula (I-1h)),

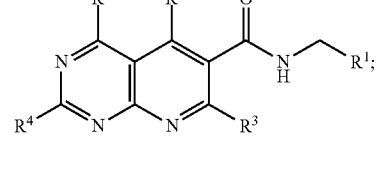

(I-1h)

or n denotes 1 and $A^1$ represents $CR^4$, $A^2$ represents N, $A^3$ represents N and $A^4$ represents $CR^4$ (formula (I-1i)), or
n denotes 1 and A¹ represents CR⁴, A² represents CR⁴, A³ represents N and A³ represents N (formula (I-1j)), (I-1j)

or
n denotes 0 and A¹ represents S, A² represents CR⁴ and A³ represents CR⁴ (formula (I-3a)), (I-3a)

or
n denotes 0 and A¹ represents S, A² represents CR⁴ and A³ represents N (formula (I-3b)), (I-3b)

or
n denotes 0 and A¹ represents O, A² represents CR⁴ and A³ represents CR⁴ (formula (I-3c)), (I-3c)

or
n denotes 0 and A¹ represents O, A² represents CR⁴ and A³ represents N (formula (I-3d)), (I-3d)

or
n denotes 0 and A¹ represents CR⁴, A² represents CR⁴ and A³ represents S (formula (I-2a)), (I-2a)

or
n denotes 0 and A¹ represents N, A² represents CR⁴ and A³ represents S (formula (I-2b)), (I-2b)

or
n denotes 0 and A¹ represents CR⁴, A² represents CR⁴ and A³ represents O (formula (I-2c)), (I-2c)

or
n denotes 0 and A¹ represents N, A² represents CR⁴ and A³ represents O (formula (I-2d)), (I-2d)

In preferred embodiment of the invention, the compound according to general formula (I) is characterized in that
n denotes 1 and A¹ represents N, A² represents CR⁴, A³ represents CR⁴ and A⁴ represents CR⁴ (I-1a);
or n denotes 1 and A¹ represents CR⁴, A² represents N, A³ represents CR⁴ and A⁴ represents CR⁴ (I-1b);

or n denotes 1 and $A^1$ represents $CR^4$, $A^2$ represents $CR^4$, $A^3$ represents N and $A^4$ represents $CR^4$ (I-1c);
or n denotes 1 and $A^1$ represents $CR^4$, $A^2$ represents $CR^4$, $A^3$ represents $CR^4$ and $A^4$ represents N (I-1d);
or n denotes 0 and $A^1$ represents $CR^4$, $A^2$ represents $CR^4$, and $A^3$ represents S (I-2a);
or n denotes 0 and $A^1$ represents S, $A^2$ represents $CR^4$ and $A^3$ represents $CR^4$ (I-3a).

In a preferred embodiment of the invention, the compound according to general formula (I) is characterized in that
$R^1$ denotes $C_{1-10}$-aliphatic residue, preferably $C_{1-8}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $S(=O)_2$—$C_{1-4}$-aliphatic residue, $CF_3$, CN, $C_{1-4}$-aliphatic residue and C(=O)—OH,
  preferably denotes $C_{1-10}$-aliphatic residue, more preferably a $C_{1-8}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)—OH,
    wherein the $C_{1-4}$-aliphatic residue in each case may be unsubstituted or mono- or polysubstituted with at least one substituent selected from the group consisting of F, Cl, Br, I, OH, $OCF_3$, $CF_3$ and unsubstituted O—$C_{1-4}$-aliphatic residue,
  or denotes $C_{3-10}$-cycloaliphatic residue or 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)—OH, $C_{3-6}$ cycloaliphatic residue, and 3 to 7 membered heterocycloaliphatic residue,
    wherein the $C_{1-4}$-aliphatic residue in each case may be unsubstituted or mono- or polysubstituted with at least one substituent selected from the group consisting of F, Cl, Br, I, OH, $OCF_3$, $CF_3$ and unsubstituted O—$C_{1-4}$-aliphatic residue, and
    wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$-aliphatic residue), an $N(C_{1-4}$-aliphatic residue)$_2$, OH, =O, an O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
    and wherein the $C_{3-10}$-cycloaliphatic residue or the 3 to 10 membered heterocycloaliphatic residue may in each case optionally linked via a $C_{1-4}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
  or denotes aryl or heteroaryl, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$, C(=O)$OC_2H_5$, $C_{3-6}$-cycloaliphatic residue, 3 to 7 membered heterocycloaliphatic residue,

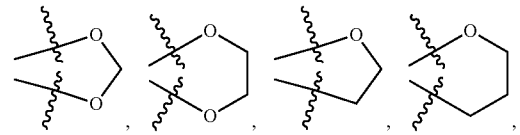

benzyl, phenyl, thienyl, pyridyl, furyl, thiazolyl and oxazolyl,
    wherein the $C_{1-4}$-aliphatic residue in each case may be unsubstituted or mono- or polysubstituted with at least one substituent selected from the group consisting of F, Cl, Br, I, OH, $OCF_3$, $CF_3$ and unsubstituted O—$C_{1-4}$-aliphatic residue, and
    wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$ aliphatic residue, $OCF_3$, $OCH_2CH_2OH$, $OCH_2OCH_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$ and C(=O)$OC_2H_5$, and
    wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
  and wherein the aryl or the heteroaryl residue may in each case be optionally linked via a $C_{1-4}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN and C(=O)OH.

In a further embodiment of the invention, the compound according to general formula (I), the residue $R^1$ represents the partial structure (T1)

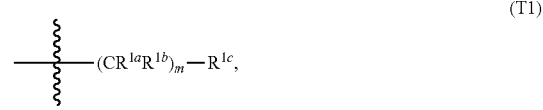

(T1)

wherein
m denotes 0, 1, 2, 3 or 4, preferably denotes 0, 1, 2 or 3, more preferably denotes 0, 1, or 2,
$R^{1a}$ and $R^{1b}$ each independently of one another represent H, F, Cl, Br, I, $NO_2$, $NH_2$, $NH(C_{1-4}$ aliphatic residue), $N(C_{1-4}$-aliphatic residue)$_2$, OH, O—$C_{1-4}$-aliphatic residue, $OCF_3$, SH, SCF$_3$, S—C$_{1-4}$ aliphatic residue, CF$_3$, CN, C$_{1-4}$-aliphatic residue or C(=O)—OH, or together denote =O preferably each independently of one another represent H, F, Cl, Br, I, NH$_2$, NH(C$_{1-4}$-aliphatic residue), N(C$_{1-4}$-aliphatic residue)$_2$, OH, O—C$_{1-4}$-aliphatic residue or C$_{1-4}$-aliphatic residue, or together denote =O, more preferably each independently of one another represent H, F, Cl, Br, I, OH, O—C$_{1-4}$-aliphatic residue or C$_{1-4}$-aliphatic residue, or together denote =O, even more preferably each independently of one another represent H, F, OH, O—C$_{1-4}$-aliphatic residue or C$_{1-4}$-aliphatic residue, or together denote =O, and R$^{1c}$ denotes C$_{1-4}$-aliphatic residue, unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, S(=O)$_2$—C$_{1-4}$-aliphatic residue, CF$_3$, CN, C$_{1-4}$-aliphatic residue and C(=O)—OH, preferably denotes C$_{1-4}$-aliphatic residue, unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, or denotes C$_{3-10}$-cycloaliphatic residue or 3 to 10 membered heterocycloaliphatic residue, in each case unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)OH, C$_{3-6}$-cycloaliphatic residue and 3 to 7 membered heterocycloaliphatic residue, preferably when m is ≠0, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and unsubstituted O—C$_{1-4}$-aliphatic residue, and wherein the C$_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)—OH, or denotes —preferably when m is 0 or 2, more preferably when m is 0— aryl or heteroaryl, in each case unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)OH, C(=O)CH$_3$, C(=O)C$_2$H$_5$, C(=O)OCH$_3$, C(=O)OC$_2$H$_5$, C$_{3-6}$-cycloaliphatic residue, 3 to 7 membered heterocycloaliphatic residue,

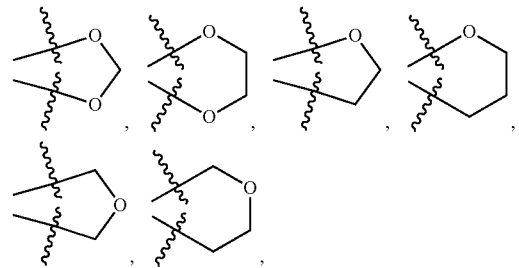

benzyl, phenyl, thienyl, pyridyl, furyl, thiazolyl and oxazolyl, preferably when m is =0, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)OH, C(=O)CH$_3$, C(=O)C$_2$H$_5$, C(=O)OCH$_3$, C(=O)OC$_2$H$_5$, and wherein the C$_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH.

Preferably,

R$^1$ represents the partial structure (T1), wherein m denotes 0, 1, or 2,

R$^{1a}$ and R$^{1b}$ each independently of one another represent H, F, Cl, Br, I, O—C$_{1-4}$-aliphatic residue or C$_{1-4}$-aliphatic residue, and R$^{1c}$ denotes C$_{1-4}$-aliphatic residue, unsubstituted or mono- or polysubstituted with at least one substituent selected from the group consisting of F, Cl, Br, I, O—C$_{1-4}$-aliphatic residue, CF$_3$ and C$_{1-4}$-aliphatic residue, wherein the C$_{1-4}$-aliphatic residue in each case may be unsubstituted or mono- or polysubstituted with at least one substituent selected from the group consisting of F, Cl, CF$_3$ and O—C$_{1-4}$-aliphatic residue, or denotes C$_{3-10}$-cycloaliphatic residue or 3 to 10 membered heterocycloaliphatic residue, in each case unsubstituted or mono- or polysubstituted with at least one substituent selected from the group consisting of F, Cl, Br, I, O—C$_{1-4}$-aliphatic residue, CF$_3$ and C$_{1-4}$-aliphatic residue, wherein the C$_{1-4}$-aliphatic residue in each case may be unsubstituted or mono- or polysubstituted with at least one substituent selected from the group consisting of F, Cl, CF$_3$ and unsubstituted O—C$_{1-4}$-aliphatic residue, or
denotes aryl or heteroaryl, in each case unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$, $C(=O)OC_2H_5$, $C_{3-6}$-cycloaliphatic residue, 3 to 7 membered heterocycloaliphatic residue, benzyl, phenyl, thienyl or pyridyl,
wherein benzyl, phenyl, thienyl and pyridyl may in each case may be unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$ and $C(=O)OC_2H_5$, and
wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, OH, =O, O—$C_{1-4}$-aliphatic residue, $OCF_3$, $CF_3$ $C_{1-4}$-aliphatic residue and $C(=O)OH$.

In a further preferred embodiment of the compound according to general formula (I), the residue
$R^1$ represents the partial structure (T1),
wherein
m is 0, 1 or 2, preferably 0 or 2, more preferably 2, and
$R^{1a}$ and $R^{1b}$ each independently of one another represent H, F, OH, O—$C_{1-4}$-aliphatic residue or $C_{1-4}$-aliphatic residue, preferably H, F, OH, $CH_3$ or $OCH_3$;
$R^{1c}$ denotes $C_{1-4}$-aliphatic residue, unsubstituted or mono- or polysubstituted with at least one substituent selected from the group consisting of F, Cl, Br, I, CN, OH, unsubstituted O—$C_{1-4}$-aliphatic residue, $CF_3$ and unsubstituted $C_{1-4}$-aliphatic residue, preferably denotes $C_{1-4}$-aliphatic residue, unsubstituted or mono- or polysubstituted with at least one substituent selected from the group consisting of F, Cl, Br, I, unsubstituted O—$C_{1-4}$-aliphatic residue, $CF_3$, and unsubstituted $C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, unsubstituted O—$C_{1-4}$-aliphatic residue, $CF_3$, and unsubstituted $C_{1-4}$-aliphatic residue,
or
wherein
m is 0 or 2, more preferably 0, and
$R^{1a}$ and $R^{1b}$ each independently of one another represent H, F, OH, O—$C_{1-4}$-aliphatic residue or $C_{1-4}$-aliphatic residue, preferably H, F, OH, $CH_3$ or $OCH_3$; and
$R^{1c}$ denotes aryl or heteroaryl, in each case unsubstituted or mono- or polysubstituted with at least one substituent selected from the group consisting of F, Cl, Br, I, OH, O—$C_{1-4}$-aliphatic residue, $OCF_3$, $OCF_2H$, $SCF_3$, $NO_2$, $N(C_{1-4}$-aliphatic residue$)_2$,

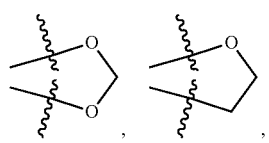 [SMILES: *OCO* ; *CCO*]

$CF_3$, CN, $C_{1-4}$-aliphatic residue, $C(=O)CH_3$, $C(=O)C_2H_5$, $C(=O)OCH_3$, $C(=O)OC_2H_5$ and phenyl, preferably denotes aryl or heteroaryl, in each case unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$, $C(=O)OC_2H_5$ and phenyl,
wherein phenyl may be unsubstituted or mono- or polysubstituted, preferably unsubstituted or mono- or disubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$ and $C(=O)OC_2H_5$, preferably with at least one substituent selected from the group consisting of F, Cl, $CH_3$, $OCH_3$, $CF_3$ and $OCF_3$.

Preferably,
$R^1$ represents the partial structure (T1),
wherein
m denotes 1 or 2,
$R^{1a}$ and $R^{1b}$ represent H,
$R^{1c}$ denotes $C_{1-4}$-aliphatic residue, unsubstituted or mono- or polysubstituted with at least one substituent selected from the group consisting of F, Cl, Br, I, O—$C_{1-4}$-aliphatic residue, $CF_3$ and $C_{1-4}$-aliphatic residue,
or
denotes $C_{3-10}$-cycloaliphatic residue or 3 to 10 membered heterocycloaliphatic residue, in each case unsubstituted or mono- or polysubstituted with at least one substituent selected from the group consisting of F, Cl, Br, I, O—$C_{1-4}$-aliphatic residue, $CF_3$ and $C_{1-4}$-aliphatic residue,
or
m denotes 0 and
$R^{1c}$ denotes aryl or heteroaryl, in each case unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$, $C(=O)OC_2H_5$, $C_{3-6}$-cycloaliphatic residue, 3 to 7 membered heterocycloaliphatic residue, benzyl, phenyl, thienyl or pyridyl,
wherein benzyl, phenyl, thienyl and pyridyl, may in each case may be unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$ and $C(=O)OC_2H_5$, and
wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, OH, =O, O—$C_{1-4}$-aliphatic residue, $OCF_3$, $CF_3$ $C_{1-4}$-aliphatic residue and $C(=O)OH$.

In another embodiment of the invention, the compound according to general formula (I) is characterized in that
$R^2$ represents H; F; Cl; Br; I; CN; $CF_3$; $NO_2$; $OCF_3$; $SCF_3$; $C_{1-4}$-aliphatic residue, S—$C_{1-4}$-aliphatic residue, O—$C_{1-4}$-aliphatic residue,
wherein the $C_{1-4}$ aliphatic residue may be in each case be unsubstituted or mono- or polysubstituted;
$C_{3-6}$-cycloaliphatic residue or 3 to 7 membered heterocycloaliphatic residue, in each case unsubstituted or mono- or polysubstituted and in each case optionally linked via a $C_{1-4}$ aliphatic group, which in turn may be unsubstituted or mono- or polysubstituted.

Preferably, $R^2$ represents H; F; Cl; Br; I; CN; $CF_3$; $NO_2$; $OCF_3$; $SCF_3$; a $C_{1-4}$-aliphatic residue, S—$C_{1-4}$-aliphatic residue, O—$C_{1-4}$-aliphatic residue,
  wherein the $C_{1-4}$-aliphatic residue in each case may be unsubstituted or mono- or polysubstituted with at least one substituent selected from the group consisting of F, Cl, Br, I, =O, OH and unsubstituted O—$C_{1-4}$-aliphatic residue,
$C_{3-6}$-cycloaliphatic residue or 3 to 7 membered heterocycloaliphatic residue, in each case unsubstituted or mono- or polysubstituted with at least one substituent selected from the group consisting of F, Cl, Br, I, =O, OH, $C_{1-4}$-aliphatic residue and O—$C_{1-4}$-aliphatic residue,
  wherein the $C_{1-4}$-aliphatic residue in each case may be unsubstituted or mono- or polysubstituted with at least one substituent selected from the group consisting of F, Cl, Br, I, =O, OH, and unsubstituted O—$C_{1-4}$-aliphatic residue,
  and wherein the $C_{3-6}$-cycloaliphatic residue or the 3 to 7 membered heterocycloaliphatic residue may in each case be optionally linked via a $C_{1-4}$-aliphatic group, which in turn may be unsubstituted or mono- or polysubstituted with at least one substituent selected from the group consisting of F, Cl, Br, I, =O, OH, unsubstituted $C_{1-4}$-aliphatic residue and unsubstituted aliphatic residue.

More preferably, $R^2$ represents H; F; Cl; Br; I; CN; $CF_3$; $NO_2$; $OCF_3$; $SCF_3$; $C_{1-4}$-aliphatic residue, a S—$C_{1-4}$-aliphatic residue, O—$C_{1-4}$-aliphatic residue,
  wherein the $C_{1-4}$-aliphatic residue in each case may be unsubstituted or mono- or polysubstituted with at least one substituent selected from the group consisting of F, Cl, Br, I, =O, OH and unsubstituted O—$C_{1-4}$-aliphatic residue,
cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, unsubstituted $C_{1-4}$-aliphatic residue and unsubstituted O—$C_{1-4}$-aliphatic residue,
and wherein cyclopropyl, cyclobutyl, cyclopentyl, cyclohexyl, pyrrolidinyl, piperazinyl, 4-methylpiperazinyl, morpholinyl or piperidinyl may in each case be optionally linked via an $C_{1-4}$-aliphatic group, which in turn may be unsubstituted or mono- or polysubstituted with at least one substituent selected from the group consisting of F, Cl, OH, unsubstituted $C_{1-4}$-aliphatic residue and unsubstituted O—$C_{1-4}$-aliphatic residue.

Even more preferably, $R^2$ represents H, F, Cl, Br, I, CN, $CF_3$, $NO_2$, $OCF_3$, $SCF_3$, $CH_3$, $CH_2CH_3$, $CH_2CH_2CH_3$, $CH(CH_3)_2$, $CH_2(CH_2)_2CH_3$, $CH_2CH(CH_3)_2$, $CH(CH_3)CH_2CH_3$, $C(CH_3)_3$, $OCH_3$, $OCH_2CH_3$, O—$(CH_2)_2$—$OCH_3$, O—$(CH_2)_2OH$; $SCH_3$, $SCH_2CH_3$, cyclopropyl, cyclobutyl, cyclopentyl, and cyclohexyl.

Still more preferably, $R^2$ is selected from the group consisting of H, F, Cl, CN, $CF_3$, $OCF_3$, $SCF_3$, $CH_3$, $CH_2CH_3$, $CH_2CH_2CH_3$, $CH(CH_3)_2$, $C(CH_3)_3$, cyclopropyl; $OCH_3$ and $OCH_2CH_3$.

In particular, $R^2$ is selected from the group consisting of H, F, Cl, $CF_3$, $CF_3$, $CH_3$, $CH_2CH_3$, $CH(CH_3)_2$, cyclopropyl and $OCH_3$.

In another embodiment of the invention, the compound according to general formula (I) is characterized in that $R^2$ represents $C_{1-4}$-aliphatic residue, preferably $CH_3$.

In another particular preferred embodiment of the invention, the compound according to general formula (I) is characterized in that $R^2$ is ≠H.

In another embodiment of the present invention, the compound according to general formula (I) is characterized in that
$R^3$ denotes $C_{2-10}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and unsubstituted O—$C_{1-4}$-aliphatic residue,
or
denotes $C_{3-6}$-cycloaliphatic residue or 3 to 7 membered heterocycloaliphatic residue, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and unsubstituted O—$C_{1-4}$-aliphatic residue, and wherein the $C_{3-6}$-cycloaliphatic residue or the 3 to 7 membered heterocycloaliphatic residue may in each case optionally linked via a $C_{1-4}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
or
denotes S—$R^5$, O—$R^6$ or $N(R^7R^8)$,
wherein
$R^5$ and $R^6$ in each case represent $C_{1-6}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and unsubstituted O—$C_{1-4}$-aliphatic residue,
or in each case represent $C_{3-6}$-cycloaliphatic residue or 3 to 7 membered heterocycloaliphatic residue, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, CF$_3$, CN, C$_{1-4}$-aliphatic residue, C(=O)OH, C$_{3-6}$-cycloaliphatic residue and 3 to 7 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and unsubstituted O—C$_{1-4}$-aliphatic residue, and wherein the C$_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, NO$_2$, NH$_2$, NH(C$_{1-4}$-aliphatic residue), an N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, and wherein the C$_{3-6}$-cycloaliphatic residue or the 3 to 7 membered heterocycloaliphatic residue may in each case optionally linked via a C$_{1-4}$-aliphatic group, which in turn may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, on the condition that if R$^5$ or R$^6$ denote a 3 to 7 membered heterocycloaliphatic residue, the 3 to 7 membered heterocycloaliphatic residue is linked via a carbon atom, R$^7$ denotes C$_{1-6}$-aliphatic residue, unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)—O—C$_{1-4}$-aliphatic residue, and C(=O)OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and unsubstituted O—C$_{1-4}$-aliphatic residue, or denotes C$_{3-6}$-cycloaliphatic residue or 3 to 7 membered heterocycloaliphatic residue, in each case unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)OH, C(=O)—O—C$_{1-4}$-aliphatic residue, C$_{3-6}$-cycloaliphatic residue, and a 3 to 7 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and unsubstituted O—C$_{1-4}$-aliphatic residue, and wherein the C$_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)—OH, and wherein the C$_{3-6}$-cycloaliphatic residue or the 3 to 7 membered heterocycloaliphatic residue may in each case optionally linked via a C$_{1-4}$-aliphatic group, which in turn may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, C(=O)—O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, on the condition that if R$^{11}$ denotes a 3 to 7 membered heterocycloaliphatic residue, the 3 to 7 membered heterocycloaliphatic residue is linked via a carbon atom, and R$^8$ denotes C$_{1-6}$-aliphatic residue, unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and unsubstituted O—C$_{1-4}$-aliphatic residue, or R$^7$ and R$^8$ form together with the nitrogen atom connecting them a 3 to 10 membered heterocycloaliphatic residue, unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)—OH, C$_{3-6}$-cycloaliphatic residue and 3 to 7 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and unsubstituted O—C$_{1-4}$-aliphatic residue, and wherein the C$_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, and wherein the 3 to 10 membered heterocycloaliphatic residue formed by R$^{11}$ and R$^{12}$ together with the nitrogen atom connecting them may optionally be condensed with aryl or heteroaryl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)—OH, C(=O)—CH$_3$, C(=O)—C$_2$H$_5$, C(=O)—OCH$_3$ and C(=O)—OC$_2$H$_5$, C$_{3-6}$-cycloaliphatic residue, 3 to 7 membered heterocycloaliphatic residue,

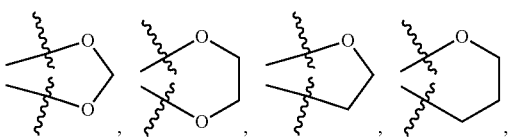

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and unsubstituted $O$—$C_{1-4}$-aliphatic residue,
and
wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, $O$—$C_{1-4}$-aliphatic residue, $OCF_3$, $OCH_2CH_2OH$, $OCH_2OCH_3$, SH, $SCF_3$, $S$—$C_{1-4}$-aliphatic residue, $CF_3$, CN, $C_{1-4}$-aliphatic residue, $C(=O)OH$, $C(=O)CH_3$, $C(=O)C_2H_5$, $C(=O)OCH_3$ and $C(=O)OC_2H_5$, and
wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, $=O$, $O$—$C_{1-4}$-aliphatic residue, $OCF_3$, SH, $SCF_3$, $S$—$C_{1-4}$-aliphatic residue, $CF_3$, CN, $C_{1-4}$-aliphatic residue and $C(=O)OH$.

Preferably,
$R^3$ denotes a $C_{2-6}$-aliphatic residue, unsubstituted or mono- or polysubstituted with at least one substituent selected from the group consisting of F, Cl, Br, I, OH, $=O$, $O$—$C_{1-4}$-aliphatic residue, $OCF_3$, SH, $SCF_3$, $S$—$C_{1-4}$-aliphatic residue, $CF_3$, CN and $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and $O$—$C_{1-4}$-aliphatic residue,
or denotes $C_{3-6}$-cycloaliphatic residue or 3 to 7 membered heterocycloaliphatic residue, in each case unsubstituted or mono- or polysubstituted with at least one substituent selected from the group consisting of F, Cl, Br, I, OH, $=O$, $O$—$C_{1-4}$ aliphatic residue, $OCF_3$, SH, $SCF_3$, $S$—$C_{1-4}$ aliphatic residue, $CF_3$, CN and $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and $O$—$C_{1-4}$-aliphatic residue,
and
and wherein the $C_{3-6}$-cycloaliphatic residue or the 3 to 7 membered heterocycloaliphatic residue may in each case optionally linked via a $C_{1-4}$-aliphatic group, which in turn may be unsubstituted or mono- or polysubstituted with at least one substituent selected from the group consisting of F, Cl, OH, $=O$, $O$—$C_{1-4}$-aliphatic residue, $OCF_3$, $SCF_3$, $CF_3$, CN, and $C_{1-4}$-aliphatic residue.

or
$R^3$ denotes $S$—$R^5$ or $O$—$R^6$,
wherein
$R^5$ and $R^6$ in each case represent $C_{1-8}$-aliphatic residue, unsubstituted or mono- or polysubstituted with at least one substituent selected from the group consisting of F, Cl, Br, I, OH, $=O$, $O$—$C_{1-4}$-aliphatic residue, $OCF_3$, SH, $SCF_3$, $S$—$C_{1-4}$-aliphatic residue, $NH(C_{1-4}$-aliphatic residue), $N(C_{1-4}$-aliphatic residue$)_2$, $CF_3$ and $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $CF_3$ and $O$—$C_{1-4}$-aliphatic residue,
or in each case denote $C_{3-6}$-cycloaliphatic residue or 3 to 7 membered heterocycloaliphatic residue, in each case unsubstituted or mono- or polysubstituted with at least one substituent selected from the group consisting of F, Cl, OH, $=O$, $O$—$C_{1-4}$-aliphatic residue, $OCF_3$, $SCF_3$, $CF_3$ and $C_{1-4}$-aliphatic residue,
wherein the $C_{1-4}$-aliphatic residue in each case may be unsubstituted or mono- or polysubstituted with at least one substituent selected from the group consisting of F, Cl, OH, $OCF_3$, $CF_3$ and $O$—$C_{1-4}$-aliphatic residue,
and wherein the $C_{3-6}$-cycloaliphatic residue or the 3 to 7 membered heterocycloaliphatic residue may in each case optionally linked via a $C_{1-4}$-aliphatic group, preferably a $C_{1-4}$-aliphatic group, which in turn may be unsubstituted or mono- or polysubstituted with at least one substituent selected from the group consisting of F, Cl, OH, $=O$, $O$—$C_{1-4}$-aliphatic residue, $OCF_3$, $CF_3$, CN, and $C_{1-4}$-aliphatic residue,
on the condition that if $R^5$ or $R^6$ denotes a 3 to 7 membered heterocycloaliphatic residue, the 3 to 7 membered heterocycloaliphatic residue is linked via a carbon atom,
or
$R^3$ denotes $N(R^7R^8)$,
wherein
$R^7$ denotes $C_{1-6}$-aliphatic residue, unsubstituted or mono- or polysubstituted with at least one substituent selected from the group consisting of F, Cl, Br, I, OH, $=O$, $O$—$C_{1-4}$-aliphatic residue, $OCF_3$, $SCF_3$, $CF_3$ and $C_{1-4}$-aliphatic residue,
wherein the $C_{1-4}$-aliphatic residue in each case may be unsubstituted or mono- or polysubstituted with at least one substituent selected from the group consisting of F, Cl, OH, $CF_3$ and $O$—$C_{1-4}$-aliphatic residue,
or denotes a $C_{3-6}$-cycloaliphatic residue or a 3 to 7 membered heterocycloaliphatic residue, in each case unsubstituted or mono- or polysubstituted with at least one substituent selected from the group consisting of F, Cl, OH, $=O$, $O$—$C_{1-4}$-aliphatic residue, $OCF_3$, $SCF_3$, $CF_3$, and $C_{1-4}$-aliphatic residue,
wherein the $C_{1-4}$-aliphatic residue in each case may be unsubstituted or mono- or polysubstituted with at least one substituent selected from the group consisting of F, Cl, OH, $OCF_3$, $CF_3$ and unsubstituted $O$—$C_{1-4}$-aliphatic residue, and
wherein the $C_{3-6}$-cycloaliphatic residue or the 3 to 7 membered heterocycloaliphatic residue may in each case be linked, preferably is linked, via a $C_{1-4}$-aliphatic group, which in turn may be unsubstituted or mono- or polysubstituted with at least one substituent selected from the group consisting of F, Cl, OH, =O, O—C$_{1-4}$-aliphatic residue, OCF$_3$, SCF$_3$, CF$_3$, CN and C$_{1-4}$-aliphatic residue,
on the condition that if R$^7$ denotes a 3 to 7 membered heterocycloaliphatic residue, the 3 to 7 membered heterocycloaliphatic residue is linked via a carbon atom,
and wherein
R$^8$ denotes C$_{1-6}$-aliphatic residue, unsubstituted or mono- or polysubstituted with at least one substituent selected from the group consisting of F, Cl, OH, =O, O—C$_{1-4}$-aliphatic residue, OCF$_3$, SCF$_3$, CF$_3$, CN and C$_{1-4}$-aliphatic residue,
 wherein the C$_{1-4}$-aliphatic residue in each case may be unsubstituted or mono- or polysubstituted with at least one substituent selected from the group consisting of F, Cl, OH, CF$_3$ and O—C$_{1-4}$-aliphatic residue,
or
R$^7$ and R$^8$ form together with the nitrogen atom connecting them a 3 to 10 membered heterocycloaliphatic residue, preferably a 3 to 7 membered heterocycloaliphatic residue, more preferably selected from the group consisting of morpholinyl, piperidinyl, pyrrolidinyl, azetidinyl and piperazinyl, in each case unsubstituted or mono- or polysubstituted with at least one substituent selected from the group consisting of F, Cl, OH, =O, O—C$_{1-4}$-aliphatic residue, OCF$_3$, SCF$_3$, CF$_3$, CN, and C$_{1-4}$-aliphatic residue,
 wherein the C$_{1-4}$-aliphatic residue in each case may be unsubstituted or mono- or polysubstituted with at least one substituent selected from the group consisting of F, Cl, Br, I, OH, CF$_3$ and unsubstituted O—C$_{1-4}$-aliphatic residue,
and wherein the 3 to 10 membered heterocycloaliphatic residue formed by R$^7$ and R$^8$ together with the nitrogen atom connecting them may optionally be condensed with aryl or heteroaryl, preferably with phenyl or pyridyl,
wherein the aryl or heteroaryl residues condensed in this way can for their part be respectively unsubstituted or mono- or polysubstituted with at least one substituent selected from the group consisting of F, Cl, OH, O—C$_{1-4}$-aliphatic residue, OCF$_3$, SCF$_3$, CF$_3$, CN, C$_{1-4}$-aliphatic residue, C(=O)OH, C$_{3-6}$ cycloaliphatic residue, 3 to 7 membered heterocycloaliphatic residue,

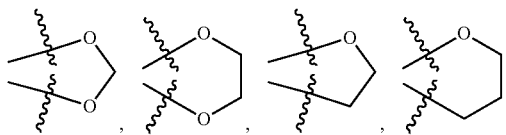

benzyl, phenyl, thienyl, and pyridyl,
wherein the C$_{1-4}$-aliphatic residue in each case may be unsubstituted or mono- or polysubstituted with at least one substituent selected from the group consisting of F, Cl, OH, OCF$_3$, CF$_3$ and O—C$_{1-4}$-aliphatic residue, and
wherein benzyl, phenyl, thienyl, and pyridyl, may in each case may be unsubstituted or mono- or polysubstituted with at least one substituent selected from the group consisting of F, Cl, OH, O—C$_{1-4}$-aliphatic residue, OCF$_3$, OCH$_2$CH$_2$OH, OCH$_2$OCH$_3$, SCF$_3$, CF$_3$, CN, C$_{1-4}$-aliphatic residue, and C(=O)OH, and
wherein the C$_{3-6}$-cycloaliphatic residue and the 3 to 7 membered heterocycloaliphatic residue may in each case may be unsubstituted or mono- or polysubstituted with at least one substituent selected from the group consisting of F, Cl, OH, =O, O—C$_{1-4}$-aliphatic residue, OCF$_3$, CF$_3$, CN, C$_{1-4}$-aliphatic residue and C(=O)OH.
More preferably,
R$^3$ denotes C$_{2-6}$-aliphatic residue, unsubstituted or mono- or polysubstituted with at least one substituent selected from the group consisting of F, Cl, OH, =O, O—C$_{1-4}$-aliphatic residue, OCF$_3$, CF$_3$ and C$_{1-4}$-aliphatic residue
 wherein the C$_{1-4}$-aliphatic residue in each case is unsubstituted,
or denotes C$_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—C$_{1-4}$ aliphatic residue, OCF$_3$, CF$_3$ and C$_{1-4}$-aliphatic residue,
 wherein the C$_{1-4}$-aliphatic residue in each case may be unsubstituted or mono- or polysubstituted with OH or unsubstituted O—C$_{1-4}$-aliphatic residue.
and wherein the C$_{3-6}$-cycloaliphatic residue or the 3 to 7 membered heterocycloaliphatic residue may in each case optionally linked via a unsubstituted C$_{1-4}$-aliphatic group,
or
R$^3$ denotes S—R$^5$ or O—R$^6$,
wherein
R$^5$ and R$^6$ in each case denote C$_{1-6}$-aliphatic residue,
 unsubstituted or mono- or polysubstituted with at least one substituent selected from the group consisting of F, Cl, OH, =O, O—C$_{1-4}$-aliphatic residue, OCF$_3$, CF$_3$ and C$_{1-4}$-aliphatic residue,
  wherein the C$_{1-4}$-aliphatic residue in each case may be unsubstituted or mono- or polysubstituted with at least one substituent selected from the group consisting of F, Cl, OH, CF$_3$ and unsubstituted O—C$_{1-4}$-aliphatic residue,
 or in each case denote C$_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—C$_{1-4}$ aliphatic residue, OCF$_3$, CF$_3$, and C$_{1-4}$-aliphatic residue,
  wherein the C$_{1-4}$-aliphatic residue in each case may be unsubstituted or mono- or polysubstituted with at least one substituent selected from the group consisting of F, Cl, OH, OCF$_3$, CF$_3$ and unsubstituted O—C$_{1-4}$-aliphatic residue, and
 wherein the C$_{3-10}$-cycloaliphatic residue or the 3 to 10 membered heterocycloaliphatic residue in each case may be linked, preferably is linked, via an unsubstituted C$_{1-4}$-aliphatic group, on the condition that if R$^5$ or R$^6$ denotes a 3 to 7 membered heterocycloaliphatic residue, the 3 to 7 membered heterocycloaliphatic residue is linked via a carbon atom,
or
R$^3$ denotes N(R$^7$R$^8$),
wherein
R$^7$ denotes C$_{1-6}$-aliphatic residue,
 unsubstituted or mono- or polysubstituted with at least one substituent selected from the group consisting of F, Cl, OH, =O, O—C$_{1-4}$-aliphatic residue, OCF$_3$, CF$_3$, and C$_{1-4}$-aliphatic residue
 wherein the C$_{1-4}$-aliphatic residue in each case may be unsubstituted or mono- or polysubstituted with at least one substituent selected from the group consisting of F, Cl, OH, CF$_3$ and unsubstituted O—C$_{1-4}$-aliphatic residue, or
- $R^7$ denotes $C_{3-7}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$ aliphatic residue, OCF$_3$, CF$_3$, and a $C_{1-4}$-aliphatic residue,
  - wherein the $C_{1-4}$-aliphatic residue in each case may be unsubstituted or mono- or polysubstituted with at least one substituent selected from the group consisting of F, Cl, OH, OCF$_3$, CF$_3$ and unsubstituted O—$C_{1-4}$-aliphatic residue, and
  - wherein the $C_{3-10}$-cycloaliphatic residue or the 3 to 10 membered heterocycloaliphatic residue may be linked via an unsubstituted $C_{1-4}$-aliphatic group,
  - on the condition that if $R^5$ denotes a 3 to 7 membered heterocycloaliphatic residue, the 3 to 7 membered heterocycloaliphatic residue is linked via a carbon atom, and
- $R^8$ denotes unsubstituted $C_{1-4}$-aliphatic residue,
  - preferably selected from the group consisting of methyl, ethyl, n-propyl, 2-propyl, n-butyl, isobutyl, sec.-butyl and tert.-butyl, more preferably selected from the group consisting of methyl and ethyl or
- $R^7$ and $R^8$ form together with the nitrogen atom connecting them a 3 to 7 membered heterocycloaliphatic residue, preferably selected from the group consisting of morpholinyl, piperidinyl, pyrrolidinyl, and azetidinyl, unsubstituted or mono- or polysubstituted with at least one substituent selected from the group consisting of F, Cl, OH, =O, O—$C_{1-4}$-aliphatic residue, OCF$_3$, CF$_3$, CN, and $C_{1-4}$-aliphatic residue,
  - wherein the $C_{1-4}$-aliphatic residue in each case may be unsubstituted or mono- or polysubstituted with at least one substituent selected from the group consisting of F, Cl, OH, CF$_3$ and unsubstituted O—$C_{1-4}$-aliphatic residue,
  - and wherein the 3 to 7 membered heterocycloaliphatic residue formed by $R^7$ and $R^8$ together with the nitrogen atom connecting them may optionally be fused with phenyl or pyridyl, wherein the phenyl or pyridyl residues fused in this way can for their part be respectively unsubstituted or mono- or polysubstituted with at least one substituent selected from the group consisting of F, Cl, OH, O—$C_{1-4}$-aliphatic residue, OCF$_3$, CF$_3$, CN, $C_{1-4}$-aliphatic residue, benzyl, phenyl, and pyridyl,
    - wherein the $C_{1-4}$-aliphatic residue in each case may be unsubstituted or mono- or polysubstituted with at least one substituent selected from the group consisting of F, Cl, OH, and unsubstituted O—$C_{1-4}$-aliphatic residue, and
    - wherein benzyl, phenyl, and pyridyl, may in each case may be unsubstituted or mono- or polysubstituted with at least one substituent selected from the group consisting of F, Cl, OCH$_3$, OCF$_3$, CF$_3$, and $C_{1-4}$-aliphatic residue.

Even more preferably,
$R^3$ denotes $C_{2-6}$-aliphatic residue, unsubstituted or mono- or polysubstituted with at least one substituent selected from the group consisting of F, Cl, OH, =O, O—$C_{1-4}$-aliphatic residue, OCF$_3$, SCF$_3$, CF$_3$ and $C_{1-4}$-aliphatic residue,
or
denotes $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, OCF$_3$, SCF$_3$, CF$_3$ and $C_{1-4}$-aliphatic residue,
  - wherein the $C_{1-4}$-aliphatic residue in each case may be unsubstituted or mono- or polysubstituted with OH or O—$C_{1-4}$-aliphatic residue,
  - and wherein the $C_{3-6}$-cycloaliphatic residue or the 3 to 7 membered heterocycloaliphatic residue may in each case optionally be linked via a $C_{1-4}$-aliphatic group,
or
$R^3$ denotes S—$R^5$ or O—$R^6$,
  wherein
  $R^5$ and $R^6$ in each case denote $C_{1-6}$-aliphatic residue, unsubstituted or mono- or polysubstituted with at least one substituent selected from the group consisting of F, Cl, OH, =O, O—$C_{1-4}$-aliphatic residue, OCF$_3$, SCF$_3$, CF$_3$ and $C_{1-4}$-aliphatic residue,
    - wherein the $C_{1-4}$-aliphatic residue in each case may be unsubstituted or mono- or polysubstituted with at least one substituent selected from the group consisting of F, Cl, OH, CF$_3$ and O—$C_{1-4}$-aliphatic residue,
  or
  in each case denote $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, OCF$_3$, SCF$_3$, CF$_3$ and $C_{1-4}$-aliphatic residue,
    - wherein the $C_{1-4}$-aliphatic residue in each case may be unsubstituted or mono- or polysubstituted with at least one substituent selected from the group consisting of F, Cl, OH, OCF$_3$, CF$_3$ and O—$C_{1-4}$-aliphatic residue,
    - and wherein the $C_{3-6}$-cycloaliphatic residue or the 3 to 7 membered heterocycloaliphatic residue in each case may be linked via an unsubstituted $C_{1-4}$-aliphatic group,
  on the condition that if $R^5$ or $R^6$ denotes 3 to 7 membered heterocycloaliphatic residue, the 3 to 7 membered heterocycloaliphatic residue is linked via a carbon atom,
or
$R^3$ denotes N($R^7R^8$),
  wherein
  $R^7$ denotes $C_{1-6}$-aliphatic residue, unsubstituted or mono- or polysubstituted with at least one substituent selected from the group consisting of F, Cl, OH, =O, O—$C_{1-4}$-aliphatic residue, OCF$_3$, SCF$_3$, CF$_3$ and $C_{1-4}$-aliphatic residue,
    - wherein the $C_{1-4}$-aliphatic residue in each case may be unsubstituted or mono- or polysubstituted with at least one substituent selected from the group consisting of F, Cl, OH, CF$_3$ and O—$C_{1-4}$-aliphatic residue,
  or
  denotes $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, OCF$_3$, SCF$_3$, CF$_3$ and $C_{1-4}$-aliphatic residue,
    - wherein the $C_{1-4}$-aliphatic residue in each case may be unsubstituted or mono- or polysubstituted with at least one substituent selected from the group consisting of F, Cl, OH, OCF$_3$, CF$_3$ and O—$C_{1-4}$-aliphatic residue, and wherein the $C_{3-6}$-cycloaliphatic residue or the 3 to 7 membered heterocycloaliphatic residue is in each case linked via a unsubstituted $C_{1-4}$-aliphatic group,
on the condition that if $R^7$ denotes 3 to 7 membered heterocycloaliphatic residue, the 3 to 7 membered heterocycloaliphatic residue is linked via a carbon atom,
and
$R^8$ in each case denotes unsubstituted $C_{1-4}$-aliphatic residue,
or
$R^7$ and $R^8$ form together with the nitrogen atom connecting them a 3 to 7 membered heterocycloaliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$, CN and $C_{1-4}$-aliphatic residue,
wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue,
and wherein the 3 to 7 membered heterocycloaliphatic residue formed by $R^7$ and $R^8$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, OH, O—$C_{1-4}$-aliphatic residue, $OCF_3$, $SCF_3$, $CF_3$, CN, $C_{1-4}$-aliphatic residue, C(=O)OH, benzyl, phenyl, and pyridyl,
wherein the $C_{1-4}$-aliphatic residue in each case may be unsubstituted or mono- or polysubstituted with at least one substituent selected from the group consisting of F, Cl, OH and O—$C_{1-4}$-aliphatic residue, and
wherein benzyl, phenyl, and pyridyl, may in each case may be unsubstituted or mono- or polysubstituted with at least one substituent selected from the group consisting of F, Cl, $OCH_3$, $OCF_3$, $OCH_2CH_2OH$, $OCH_2CH_2OCH_3$, $SCF_3$, $CF_3$ and $C_{1-4}$-aliphatic residue.

More preferably,
$R^3$ denotes $CH_2CH_3$, $CH_2CH_2CH_3$, $CH(CH_3)_2$, $CH_2(CH_2)_2CH_3$, $CH_2CH(CH_3)_2$, $CH(CH_3)CH_2CH_3$, $C(CH_3)_3$, $CH_2(CH_2)_3CH_3$, $CH_2CH_2CH(CH_3)_2$, $CH_2C(CH_3)_3$, $CH_2(CH_2)_4CH_3$, $CH=CH_2$ or $CH_2CH=CH_2$,
in each case unsubstituted or mono- or polysubstituted with at least one substituent selected from the group consisting of F, Cl, OH, O—$C_{1-4}$-aliphatic residue, $CF_3$ and $C_{1-4}$-aliphatic residue, preferably in each case unsubstituted or mono- or polysubstituted with at least one substituent selected from the group consisting of F, Cl, and an O—$C_{1-4}$-aliphatic residue, preferably $OCH_3$, more preferably in each case unsubstituted,
wherein the $C_{1-4}$-aliphatic residue in each case is unsubstituted,
or denotes cyclopropyl, cyclobutyl, cyclopentyl and cyclohexyl, oxetanyl, piperidinyl, tetrahydrofuranyl, or tetrahydropyranyl,
preferably denotes cyclopropyl or tetrahydropyranyl,
more preferably cyclopropyl,
in each case unsubstituted or mono- or polysubstituted with at least one substituent selected from the group consisting of F, Cl, OH, O—$C_{1-4}$-aliphatic residue, $CF_3$ and $C_{1-4}$-aliphatic residue,
preferably in each case unsubstituted or mono- or polysubstituted with at least one substituent selected from the group consisting of F, Cl and O—$C_{1-4}$-aliphatic residue, preferably $OCH_3$, more preferably in each case unsubstituted,
wherein the $C_{1-4}$-aliphatic residue in each case is unsubstituted,
and wherein cyclopropyl, cyclobutyl, cyclopentyl and cyclohexyl, oxetanyl, piperidinyl, tetrahydrofuranyl, and tetrahydropyranyl may in each case be optionally bridged via an unsubstituted $C_{1-4}$-aliphatic group, preferably via an unsubstituted $C_{1-2}$-aliphatic group,
or
$R^3$ denotes S—$R^5$ or O—$R^6$,
wherein
$R^5$ and $R^6$ in each case denote $CH_3$, $CH_2CH_3$, $CH_2CH_2CH_3$, $CH(CH_3)_2$, $CH_2(CH_2)_2CH_3$, $CH_2CH(CH_3)_2$, $CH(CH_3)CH_2CH_3$, $C(CH_3)_3$, $CH_2(CH_2)_3CH_3$, $CH_2CH_2CH(CH_3)_2$, $CH_2C(CH_3)_3$, $CH_2(CH_2)_4CH_3$, $CH=CH_2$ or $CH_2CH=CH_2$ in each case unsubstituted or mono- or polysubstituted with at least one substituent selected from the group consisting of F, Cl, OH, and O—$C_{1-4}$-aliphatic residue,
wherein the $C_{1-4}$-aliphatic residue in each case is unsubstituted,
or in each case denote cyclopropyl, cyclobutyl, cyclopentyl cyclohexyl, oxetanyl, piperidinyl, tetrahydrofuranyl, or tetrahydropyranyl, preferably cyclopropyl or oxetanyl, in each case unsubstituted or mono- or polysubstituted with at least one substituent selected from the group consisting of F, Cl, OH, O—$C_{1-4}$-aliphatic residue, $CF_3$ and $C_{1-4}$-aliphatic residue,
preferably in each case unsubstituted or mono- or polysubstituted with at least one substituent selected from the group consisting of F, Cl and O—$C_{1-4}$-aliphatic residue, more preferably in each case unsubstituted,
wherein the $C_{1-4}$-aliphatic residue in each case is unsubstituted,
and wherein cyclopropyl, cyclobutyl, cyclopentyl and cyclohexyl, oxetanyl, piperidinyl, tetrahydrofuranyl, and tetrahydropyranyl may in each case be optionally linked via an unsubstituted $C_{1-4}$-aliphatic group,
on the condition that if $R^5$ or $R^6$ denotes piperidinyl, oxetanyl, tetrahydrofuranyl, or tetrahydropyranyl, each of these residues is linked via a carbon atom,
or
$R^3$ denotes $N(R^7R^8)$,
wherein
$R^7$ denotes $C_{1-6}$-aliphatic residue,
unsubstituted or mono- or polysubstituted with at least one substituent selected from the group consisting of F, Cl, =O, OH and $OCH_3$,
preferably unsubstituted or mono- or polysubstituted with at least one substituent selected from the group consisting of F, Cl and $OCH_3$,
more preferably unsubstituted or mono- or polysubstituted with at least one substituent selected from the group consisting of F and $OCH_3$,
preferably denotes unsubstituted $C_{1-6}$-aliphatic residue,
more preferably selected from the group consisting of $CH_3$, $CH_2CH_3$, $CH_2CH_2CH_3$, $CH(CH_3)_2$, $CH_2(CH_2)_2CH_3$, $CH_2CH(CH_3)_2$, $CH(CH_3)CH_2CH_3$, $C(CH_3)_3$, $CH_2(CH_2)_3CH_3$, $CH_2CH_2CH(CH_3)_2$, $CH_2C(CH_3)_3$ and $CH_2(CH_2)_4CH_3$, and $R^8$ denotes $CH_3$, $CH_2CH_3$, $CH_2CH_2CH_3$, $CH(CH_3)_2$, $CH_2(CH_2)_2CH_3$, $CH_2CH(CH_3)_2$, $CH(CH_3)CH_2CH_3$ or $C(CH_3)_3$, more preferably $CH_3$ or $CH_2CH_3$ or $R^7$ and $R^8$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, OH, O—$C_{1-4}$-aliphatic residue and $C_{1-4}$-aliphatic residue, more preferably unsubstituted or mono- or polysubstituted with at least one substituent selected from the group consisting of F, Cl and O—$C_{1-4}$-aliphatic residue, preferably form together with the nitrogen atom connecting them a morpholinyl, piperidinyl, pyrrolidinyl, or azetidinyl, in each case unsubstituted.

In a particular preferred embodiment of the present invention, the compound according to general formula (I) is characterized in that $R^3$ is selected from the group consisting of $C_2H_5$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2$-cyclopropyl, $OCH_3$, $OC_2H_5$, $OCH_2CH_2CH_3$, $OCH(CH_3)_2$, O-cyclopropyl, $SCH_3$, $SC_2H_5$, $SCH_2CH_2CH_3$, $SCH(CH_3)_2$, S-cyclopropyl, cyclopropyl, cyclobutyl, cyclopentyl, cyclohexyl, $N(CH_3)_2$, $N(CH_3)C_2H_5$, $N(CH_3)CH_2CH_2CH_3$, $N(CH_3)CH(CH_3)_2$, $N(CH_3)$-cyclopropyl, $N(C_2H_5)_2$, $N(C_2H_5)CH_2CH_2CH_3$, $N(C_2H_5)CH(CH_3)_2$, $N(C_2H_5)$-cyclopropyl, N-aziridinyl, N-azetidinyl, N-pyrrolidinyl, N-piperidinyl or N-morpholinyl, in each case unsubstituted or mono- or polysubstituted with F, OH and/or $OCH_3$.

In another embodiment of the invention, the compound according to general formula (I) is characterized in that each $R^4$ independently represents H, F, Cl, Br, I, CN, $CF_3$, $CHF_2$, $CH_2F$, $OCF_3$, $OCHF_2$, $OCH_2F$, $SCF_3$, aliphatic residue, $C_{1-4}$-aliphatic residue or $S(=O)_2$—$C_{1-4}$-aliphatic residue.

Preferably, each $R^4$ independently represents H, F, Cl, Br, CN, $CF_3$, $OCF_3$, $CH_3$, $OCH_3$ or $S(=O)_2CH_3$.

More preferably, each $R^4$ independently represents H or $CF_3$.

In one preferred embodiment of the invention, each $R^4$ represents H.

In another preferred embodiment of the invention, at least one $R^4$ does not represent H.

In another preferred embodiment of the invention, at least one $R^4$ represents $CF_3$.

In particularly preferred embodiment of the invention, the compound according to general formula (I) is characterized in that $A^1$, $A^2$ and $A^3$ independently of each other represent $CR^4$, N, O, S or $N(CH_3)$, $A^4$ represents $CR^4$ or N, and n denotes 0 or 1, with the proviso, that at least one of $A^1$, $A^2$, $A^3$ and $A^4$ does not represent $CR^4$, and with the proviso, that if n denotes 0, then precisely one of $A^1$, $A^2$ and $A^3$ represents O, S or $N(CH_3)$, or if n denotes 1, then $A^1$, $A^2$ and $A^3$ independently of each other represent $CR^4$ or N, $R^1$ represents the partial structure (T1),

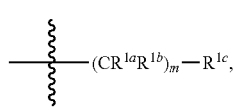

(T1)

wherein m denotes 0, 1, or 2, $R^{1a}$ and $R^{1b}$ each independently of one another represent H, F, Cl, O—$C_{1-4}$-aliphatic residue or $C_{1-4}$-aliphatic residue, $R^{1c}$ denotes $C_{1-4}$-aliphatic residue, unsubstituted or mono- or polysubstituted with at least one substituent selected from the group consisting of F, Cl, O—$C_{1-4}$ aliphatic residue, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and O—$C_{1-4}$-aliphatic residue, or denotes $C_{3-10}$-cycloaliphatic residue or 3 to 10 membered heterocycloaliphatic residue, in each case unsubstituted or mono- or polysubstituted with at least one substituent selected from the group consisting of F, $C_{1-10}$—$C_{1-4}$-aliphatic residue, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and O—$C_{1-4}$-aliphatic residue, or denotes aryl or heteroaryl, in each case unsubstituted or mono- or polysubstituted with at least one substituent selected from the group consisting of F, Cl, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$, $C(=O)OC_2H_5$, $C_{3-6}$-cycloaliphatic residue, 3 to 7 membered heterocycloaliphatic residue, benzyl, phenyl, thienyl or pyridyl, wherein benzyl, phenyl, thienyl and pyridyl, may in each case may be unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$ and $C(=O)OC_2H_5$, and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, OH, =O, O—$C_{1-4}$-aliphatic residue, $OCF_3$, $CF_3$ $C_{1-4}$-aliphatic residue and $C(=O)OH$, $R^2$ represents F; Cl; Br; I; CN; $CF_3$; $NO_2$; $OCF_3$; $SCF_3$; $C_{1-4}$-aliphatic residue, S—$C_{1-4}$-aliphatic residue or O—$C_{1-4}$-aliphatic residue, wherein the $C_{1-4}$-aliphatic residue in each case may be unsubstituted or mono- or polysubstituted with at least one substituent selected from the group consisting of F, Cl, =O, OH and O—$C_{1-4}$-aliphatic residue, $R^3$ denotes $C_{2-6}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, or
  denotes $C_{3-10}$-cycloaliphatic residue or 3 to 10 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue,
    wherein the $C_{1-4}$-aliphatic residue in each case may be unsubstituted or mono- or polysubstituted with OH or O—$C_{1-4}$-aliphatic residue, and
    wherein the $C_{3-10}$-cycloaliphatic residue or the 3 to 10 membered heterocycloaliphatic residue may in each case optionally linked via a $C_{1-4}$-aliphatic group,
or
$R^3$ denotes S—$R^5$ or O—$R^6$,
  wherein
    $R^5$ and $R^6$ in each case denote $C_{1-8}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue,
      wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue,
    or
    in each case denote $C_{3-8}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue,
      wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue, and
      wherein the $C_{3-8}$-cycloaliphatic residue or the 3 to 7 membered heterocycloaliphatic residue in each case may be linked via an unsubstituted $C_{1-4}$-aliphatic group,
    on the condition that if $R^5$ or $R^6$ denotes 3 to 7 membered heterocycloaliphatic residue, the 3 to 7 membered heterocycloaliphatic residue is linked via a carbon atom,
or
$R^3$ denotes $N(R^7R^8)$,
  wherein
    $R^7$ denotes $C_{1-8}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue
      wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue,
    or
    denotes $C_{3-8}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, C(=O)—O—$C_{1-4}$-aliphatic residue, $CF_3$ and $C_{1-4}$-aliphatic residue,
      wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue, and
      wherein the $C_{3-6}$-cycloaliphatic residue or the 3 to 7 membered heterocycloaliphatic residue is in each case linked via an unsubstituted $C_{1-4}$-aliphatic group,
    on the condition that if $R^7$ denotes 3 to 7 membered heterocycloaliphatic residue, the 3 to 7 membered heterocycloaliphatic residue is linked via a carbon atom,
  and
  $R^8$ denotes unsubstituted $C_{1-4}$-aliphatic residue,
or
$R^7$ and $R^8$ form together with the nitrogen atom connecting them a 3 to 7 membered heterocycloaliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$, CN and $C_{1-4}$-aliphatic residue,
  wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue, and
  wherein the 3 to 7 membered heterocycloaliphatic residue formed by $R^7$ and $R^8$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, OH, O—$C_{1-4}$-aliphatic residue, $OCF_3$, $SCF_3$, $CF_3$, CN, $C_{1-4}$-aliphatic residue, C(=O)OH, benzyl, phenyl, and pyridyl,
    wherein the $C_{1-4}$-aliphatic residue in each case may be unsubstituted or mono- or polysubstituted with at least one substituent selected from the group consisting of F, Cl, OH, and O—$C_{1-4}$-aliphatic residue, and wherein benzyl, phenyl, and pyridyl, may in each case may be unsubstituted or mono- or polysubstituted with at least one substituent selected from the group consisting of F, Cl, $OCH_3$, $OCF_3$, $OCH_2CH_2OH$, O $CH_2CH_2OCH_3$, SH, $SCF_3$, $CF_3$ and $C_{1-4}$-aliphatic residue,
and
each $R^4$ independently represents H, F, Cl, Br, CN, $CF_3$, $OCF_3$, $CH_3$, $OCH_3$ or $S(=O)_2CH_3$.

In more particularly preferred embodiment of the invention, the compound according to general formula (I) is characterized in that
$A^1$, $A^2$ and $A^3$ independently of each other represent $CR^4$, N, O, S or $N(CH_3)$,
$A^4$ represents $CR^4$ or N, and
n denotes 0 or 1,
with the proviso, that
at least one of $A^1$, $A^2$, $A^3$ and $A^4$ does not represent $CR^4$,
and with the proviso, that
if n denotes 0, then precisely one of $A^1$, $A^2$ and $A^3$ represents O, S or $N(CH_3)$, or
if n denotes 1, then $A^1$, $A^2$ and $A^3$ independently of each other represent $CR^4$ or N, $R^1$ represents the partial structure (T1),

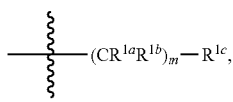

(T1)

wherein
m denotes 0,
$R^{1c}$ denotes aryl or heteroaryl, in each case unsubstituted or mono- or polysubstituted with at least one substituent selected from the group consisting of F, Cl, OH, O—$C_{1-4}$-aliphatic residue, $OCF_3$, $CF_3$, CN, $C_{1-4}$-aliphatic residue, C(=O)$CH_3$, C(=O)$C_2H_5$, C(=O)$OCH_3$, C(=O)$OC_2H_5$, $C_{3-6}$-cycloaliphatic residue, 3 to 7 membered heterocycloaliphatic residue, benzyl, phenyl, thienyl or pyridyl,
wherein benzyl, phenyl, thienyl and pyridyl, may in each case may be unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, C(=O)$CH_3$, C(=O)$C_2H_5$, C(=O)$OCH_3$ and C(=O)$OC_2H_5$, and
wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, OH, =O, O—$C_{1-4}$-aliphatic residue, $OCF_3$, $CF_3$ $C_{1-4}$-aliphatic residue and C(=O)OH,
$R^2$ represents F, Cl, CN, $CF_3$, $OCF_3$, $CH_3$, or $OCH_3$,
$R^3$ denotes S—$R^5$ or O—$R^6$,
wherein
$R^5$ and $R^6$ in each case denote $C_{1-8}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue,
wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue,
and
each $R^4$ independently represents H, F, $C_1$ or $CF_3$.

Especially particularly preferred are compounds according to general formula (I) selected from the group comprising:
1 2-Ethylsulfanyl-N-[(3-fluorophenyl)-methyl]-4-methyl-[1,5]naphthyridine-3-carboxylic acid amide;
2 2-Ethylsulfanyl-N-[(4-fluorophenyl)-methyl]-4-methyl-[1,5]naphthyridine-3-carboxylic acid amide;
3 2-Ethylsulfanyl-N-[(3-fluorophenyl)-methyl]-4-methyl-[1,6]naphthyridine-3-carboxylic acid amide;
4 2-Ethylsulfanyl-N-[(4-fluorophenyl)-methyl]-4-methyl-[1,6]naphthyridine-3-carboxylic acid amide;
5 2-Ethylsulfanyl-N-[(3-fluorophenyl)-methyl]-4-methyl-[1,7]naphthyridine-3-carboxylic acid amide;
6 2-Ethylsulfanyl-N-[(4-fluorophenyl)-methyl]-4-methyl-[1,7]naphthyridine-3-carboxylic acid amide;
7 2-Ethylsulfanyl-N-[(3-fluorophenyl)-methyl]-4-methyl-[1,8]naphthyridine-3-carboxylic acid amide;
8 2-Ethylsulfanyl-N-[(4-fluorophenyl)-methyl]-4-methyl-[1,8]naphthyridine-3-carboxylic acid amide;
9 2-Ethylsulfanyl-N-[(3-fluorophenyl)-methyl]-4-methyl-7-(trifluoromethyl)-[1,8]naphthyridine-3-carboxylic acid amide;
10 2-Ethylsulfanyl-N-[(4-fluorophenyl)-methyl]-4-methyl-7-(trifluoromethyl)-[1,8]naphthyridine-3-carboxylic acid amide;
11 2-Ethylsulfanyl-N-[(3-fluorophenyl)-methyl]-4-methyl-7-(trifluoromethyl)-[1,6]naphthyridine-3-carboxylic acid amide;
12 2-Ethylsulfanyl-N-[(4-fluorophenyl)-methyl]-4-methyl-7-(trifluoromethyl)-[1,6]naphthyridine-3-carboxylic acid amide;
13 2-Ethylsulfanyl-N-[(3-fluorophenyl)-methyl]-4-methyl-7-(trifluoromethyl)-[1,5]naphthyridine-3-carboxylic acid amide;
14 2-Ethylsulfanyl-N-[(4-fluorophenyl)-methyl]-4-methyl-7-(trifluoromethyl)-[1,5]naphthyridine-3-carboxylic acid amide;
15 5-Ethylsulfanyl-N-[(3-fluorophenyl)-methyl]-7-methyl-thieno[3,2-b]pyridine-6-carboxylic acid amide;
16 6-Ethylsulfanyl-N-[(3-fluorophenyl)-methyl]-4-methyl-thieno[2,3-b]pyridine-5-carboxylic acid amide;
17 5-Ethoxy-N-[(3-fluorophenyl)-methyl]-7-methyl-2-(trifluoromethyl)-thieno[3,2-b]pyridine-6-carboxylic acid amide;
18 6-Ethoxy-N-[(3-fluorophenyl)-methyl]-4-methyl-2-(trifluoromethyl)-thieno[2,3-b]pyridine-5-carboxylic acid amide;
in the form of a free compound, a solvate and/or a physiologically acceptable salt, respectively as racemate, as individual enantiomers, as individual diastereomers, as mixtures of the enantiomers in any mixing ratio or as mixtures of the diastereomers in any mixing ratio.

The compounds of the general formula (I) and corresponding stereoisomers and also the respective corresponding salts and solvates are toxicologically safe and are therefore suitable as pharmaceutical active ingredients in pharmaceutical compositions.

In another aspect, the present invention therefore further relates to a pharmaceutical composition containing at least one compound according to general formula (I), in each case if appropriate in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a physiologically acceptable salt, or respectively in the form of a corresponding solvate, and also if appropriate one or more pharmaceutically acceptable auxiliaries.

These pharmaceutical compositions according to the invention are suitable in particular for the modulation of KCNQ2/3 $K^+$ channels, preferably for KCNQ2/3 $K^+$ channel inhibition and/or KCNQ2/3 $K^+$ channel stimulation, i.e. they exert an agonistic or antagonistic effect.

Likewise, the pharmaceutical compositions according to the invention are preferably suitable for the prophylaxis and/or treatment of disorders and/or diseases which are mediated, at least in part, by KCNQ2/3 $K^+$ channels. The pharmaceutical composition according to the invention is suitable for administration to adults and children, including toddlers and babies.

The pharmaceutical composition according to the invention may be prepared as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of general formula (I), if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally may contain further physiologically acceptable pharmaceutical auxiliaries which, for example, can be selected from the group consisting of excipients, fillers, solvents, diluents, surface-active substances, dyes, preservatives, blasting agents, slip additives, lubricants, aromas and binders.

The selection of the physiologically acceptable auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository, in a dissolved form or in a plaster, and further agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention can be prepared with the aid of conventional means, devices, methods and process known in the art, such as are described for example in "Remington's Pharmaceutical Sciences", A. R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula (I) may vary and is for example dependent on the patient's weight or age and also on the type of application, the indication and the severity of the disorder. Conventionally, 0.001 to 100 mg/kg, preferably 0.05 to 75 mg/kg, particularly preferably 0.05 to 50 mg of at least one compound according to the invention are applied per kg of the patient's body weight.

The pharmaceutical composition according to the invention is preferably suitable for the prophylaxis and/or treatment of disorders and/or diseases which are mediated, at least in part, by KCNQ2/3 $K^+$ channels. The pharmaceutical composition according to the invention is more preferably suitable for the treatment and/or prophylaxis of one or more diseases and/or disorders selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

The pharmaceutical composition according to the invention is suitable particularly preferably for the treatment of pain, more particularly preferably of acute pain, chronic pain, neuropathic pain, visceral pain, inflammatory pain and muscular pain, and most particularly for the treatment of neuropathic pain.

The pharmaceutical composition according to the invention is also preferably suitable for the treatment and/or prophylaxis of epilepsy.

In a further aspect of the present invention, the invention therefore relates to at least one compound according to general formula (I) and also if appropriate of one or more pharmaceutically acceptable auxiliaries for the prophylaxis and/or treatment of disorders and/or diseases which are mediated, at least in part, by KCNQ2/3 $K^+$ channels.

Preference is given to at least one compound according to general formula (I) and optionally one or more pharmaceutically acceptable auxiliaries for the prophylaxis and/or treatment of disorders and/or diseases selected from the group consisting of pain, especially pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for the prophylaxis and/or treatment of epilepsy.

In another aspect of the invention, the present invention further relates to at least one compound according to general formula (I) and also if appropriate of one or more pharmaceutically acceptable auxiliaries for use in the preparation of a medicament for prophylaxis and/or treatment of disorders and/or diseases which are mediated, at least in part, by KCNQ2/3 $K^+$ channels.

Preference is given to at least one compound according to general formula (I) and optionally one or more pharmaceutically acceptable auxiliaries for use in the preparation of a medicament for the prophylaxis and/or treatment of disorders and/or diseases selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for use in the preparation of a medicament for the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for use in the preparation of a medicament for the prophylaxis and/or treatment of epilepsy.

Another aspect of the present invention is a method of treatment and/or prophylaxis of disorders and/or diseases, which are mediated, at least in part, by KCNQ2/3 K$^+$ channels, in a mammal, preferably of disorders and/or diseases selected from the group consisting of pain, preferably pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias, which comprises administering an effective amount of at least one compound of general formula (I) to the mammal.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74 79 (1941)) or by the formalin test (e.g. according to D. Dubuisson et al., Pain 1977, 4, 161-174). The effectiveness against epilepsy can be demonstrated, for example, in the DBA/2 mouse model (De Sarro et al., Naunyn-Schmiedeberg's Arch. Pharmacol. 2001, 363, 330-336).

The compounds according to the invention preferably have a $EC_{50}$ value of not more than 10000 nM or not more than 8000 nM, more preferably not more than 7000 nM or not more than 6000 nM, yet more preferably not more than 5000 nM or not more than 3000 nM, even more preferably not more than 2000 nM or not more than 1000 nM, yet even more preferably not more than 800 nM or not more than 700 nM, still more preferably not more than 600 nM or not more than 500 nM, yet still more preferably not more than 400 nM or not more than 300 nM, most preferably not more than 200 nM or not more than 150 nM and especially not more than 120 nM or not more than 100 nM. Methods for determining the $EC_{50}$ value are known to the person skilled in the art. The $EC_{50}$ value is preferably determined by fluorimetry, particularly preferably as described below under "pharmacological experiments".

The invention further provides processes for the preparation of the substituted compounds according to the invention.

The chemicals and reaction components used in the reactions and schemes described below are available commercially or in each case can be prepared by conventional methods known to the person skilled in the art.

The reactions described can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps described below, as well as the respective purification and/or isolation of intermediate or end products, can be carried out partly or completely under an inert gas atmosphere, preferably under a nitrogen atmosphere.

If the compounds according to general formula (I) are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulphonic acid, to be separated from one another.

The various, and in particular the preferred, embodiments of the first aspect of the present invention apply in analogous manner—mutatis mutandis—to the other aspects of the present invention.

The compounds according to invention may be prepared as shown in reaction schemes below:

General reaction scheme I (synthesis of precursors SNS-003):

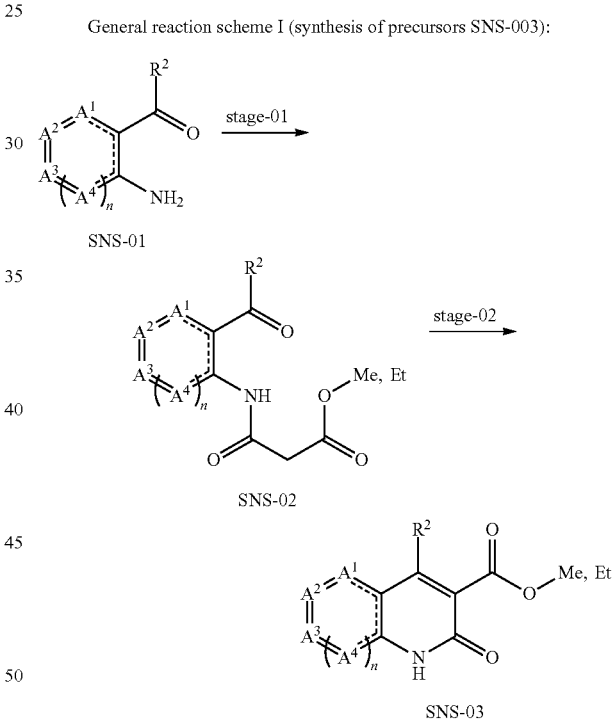

A plurality of syntheses of and synthesis paths to compounds of the general formula SNS-001 with numerous residues $R^2$ and with a very broad substitution pattern for residues $R^4$ in case of $A^1$, $A^2$, $A^3$ or $A^4$ represent $CR^4$ are known in the current specialist literature. Previously unknown intermediates of the general formula SNS-001 with similar substitution patterns for residues $R^2$ and $R^4$ as outlined below and whose syntheses are not described in greater detail, can be produced by the person skilled in the art according to these known methods or by combination of the known methods.

In stage-01 amino-ketones of the general formula SNS-01 can be transformed into amides of the general formula SNS-02, for example, with acid chlorides of the general formula Cl(C=O)—CH$_2$—(C=O)—O(Me/Et), according to methods known to the person skilled in the art, for example, by addition of a base, for example NEt₃.

In stage-02 amido-ketones of the general formula SNS-02 can be cyclized to quinolones of the general formula SNS-03, according to methods known to the person skilled in the art, for example, by addition of a base, for example, NaH or NaOEt in an appropriate solvents, for example, EtOH.

In stage-06 2-chloro-quinolines of the general formula SNS-07 can be transformed into 2-mercapto-quinolines of the general formula SNS-06, for example, with compounds of the general formula M-S—R⁵, where M denotes a hydrogen atom or a metal, for example, sodium or potassium, according to methods known to the person skilled in the art, for example, by addition of a base, for example, K₂CO₃ or NEt₃.

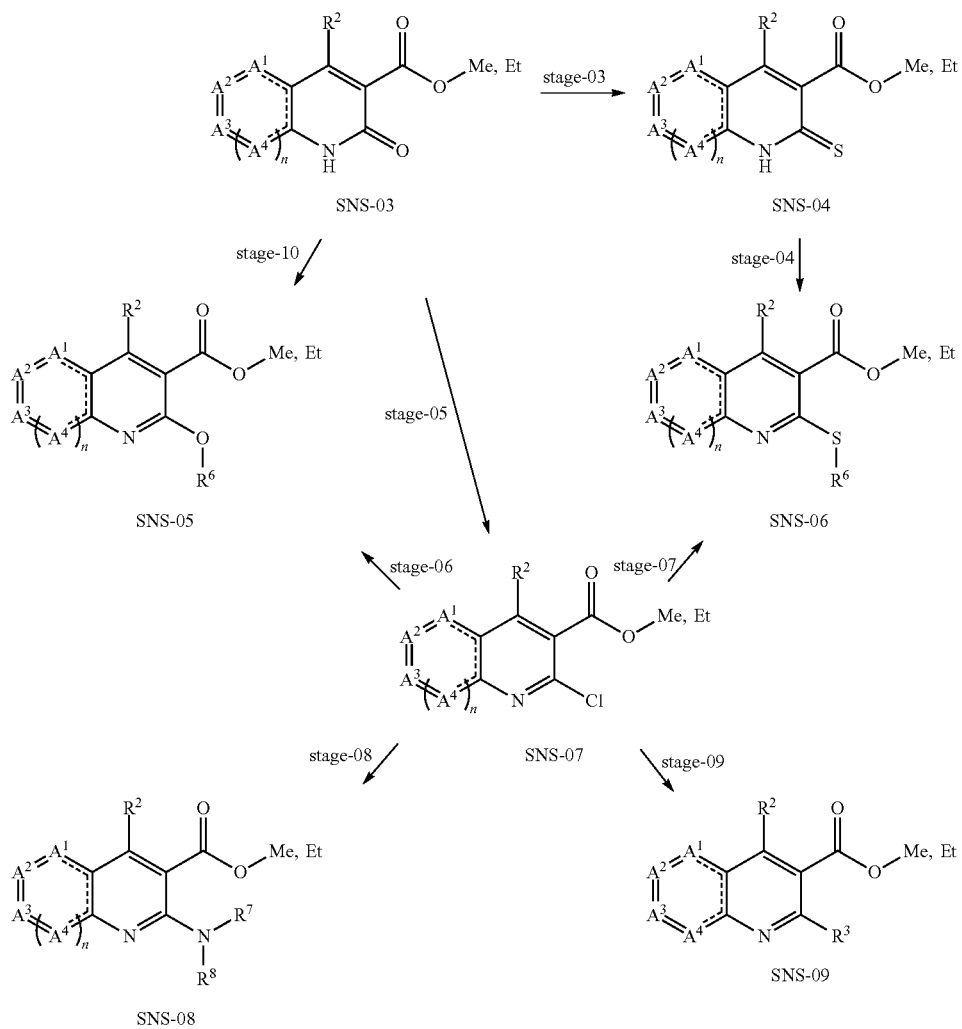

General reaction scheme II

In stage-03 quinolones of the general formula SNS-03 can be transformed into quinolinethiones of the general formula SNS-04, according to methods known to the person skilled in the art, for example, by use of Lawesson's reagent.

In stage-04 quinolinethiones of the general formula SNS-04 can be transformed into 2-mercapto-quinolines of the general formula SNS-06, with compounds of the general formula X—R⁵, where X denotes a leaving group, for example Methylsulfonyl or a halide, for example, chlorine, according to methods known to the person skilled in the art, for example, by addition of a base, for example, K₂CO₃ or NEt₃.

In stage-05 quinolones of the general formula SNS-03 can be transformed into 2-chloro-quinolines of the general formula SNS-07, according to methods known to the person skilled in the art, for example, by use of POCl₃ reagent.

In stage-07 2-chloro-quinolines of the general formula SNS-07 can be transformed into 2-alkyoxy-quinolines of the general formula SNS-05, for example, with compounds of the general formula M-O—R⁵, where M denotes a hydrogen atom or a metal, for example, sodium or potassium, according to methods known to the person skilled in the art, for example, by addition of a base, for example, NaH or NaOH.

In stage-08 2-chloro-quinolines of the general formula SNS-07 can be transformed into 2-amino-quinolines of the general formula SNS-05, for with amines of the general formula HNR⁷R⁸ according to methods known to the person skilled in the art, for example, by adding a base, for example NEt₃.

In stage-09 2-chloro-quinolines of the general formulae SNS-07 be transformed into 2-alykl-quinolines of the general formula SNS-09, where R³ is attached via a carbon atom, with compounds of the general formula X—R³, where or X denotes a residue to form an organometal reagent, for example MgBr, MgCl or Bu₃Sn according to methods known to the person skilled in the art, optionally in the presence of a suitable base, for example NEt₃, DIPEA, K₂CO₃, Cs₂CO₃, NaOtBu or KOtBu, optionally by addition of a suitable coupling reagent, for example Pd(PPh₃)₄, Ni(dppp)Cl₂ or Fe(acac)₃.

In stage-10 quinolinones of the general formula SNS-04 can be transformed into 2-alkoxy-quinolines of the general formula SNS-06, with compounds of the general formula X—R⁶, where X denotes a leaving group, for example Methylsulfonyl or a halide, for example, chlorine, according to methods known to the person skilled in the art, for example, by addition of a base, for example, Ag₂CO₃, K₂CO₃ or NEt₃.

FURTHER ABBREVIATIONS brine saturated aqueous sodium chloride solution
CC column chromatography on silica gel
DCM dichloromethane
DMF N,N-dimethylformamide
EtOAc ethyl acetate
h hour(s)
HATU O-(7-aza-benzotriazol-1-yl)-N,N,N',N'-tetramethyluroniumhexafluorophosphate
m/z mass-to-charge ratio
LR Lawesson's reagent (2,4-bis(4-methoxyphenyl)-1,3,2,4-dithiadiphosphetane-2,4-dithione)
min minutes
MS mass spectrometry General reaction scheme III (synthesis of examples of the general formula I):

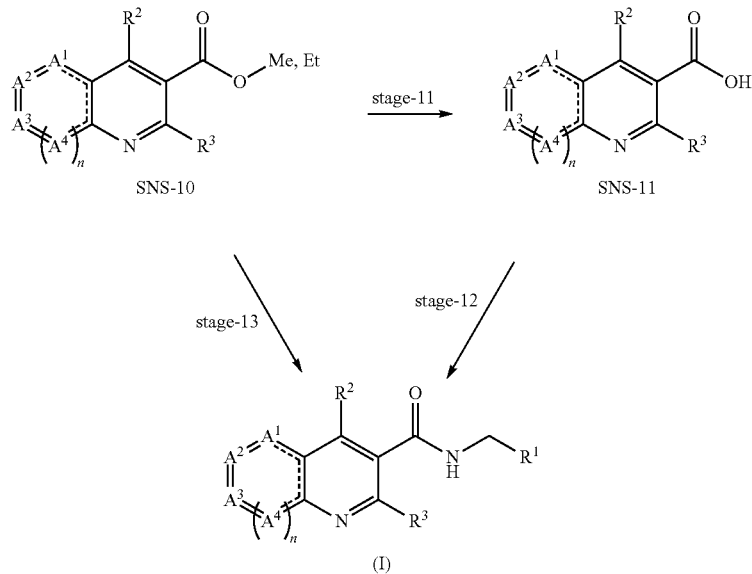

In stage-11 methyl or ethyl ester of the general formula SNS-10 can be transformed into the corresponding acid of the general formula SNS-11, according to methods known to the person skilled in the art, for example, by use of a base, for example, LiOH.

In stage-12 acids of the general formulae SNS-11 can be transformed into amides of the general formula I, with amines of the general formula R¹—CH₂—NH₂ according to methods known to the person skilled in the art, for example, by using a suitable coupling reagent, for example, HATU.

In stage-13 methyl or ethyl ester of the general formula SNS-10 can be transformed into amides of the general formula (I), with amines of the general formula R¹—CH₂—NH₂ according to methods known to the person skilled in the art, for example, by using a suitable coupling reagent, for example, trimethyl-alumina.

EXAMPLES

The indication "equivalents" ("eq.") means molar equivalents, "RT" means room temperature (23±7° C.), "M" are indications of concentration in mol/l, "aq." means aqueous, "sat." means saturated, "sol." means solution, "conc." means concentrated.

TEA triethylamine
RM reaction mixture
v/v volume to volume
w/w weight in weight

The yields of the compounds prepared were not optimised. All temperatures are uncorrected. All starting materials which are not explicitly described were either commercially available (the details of suppliers such as for example Acros, Avocado, Aldrich, Bachem, Fluke, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The mixing ratios of solvents or eluents for chromatography are specified in v/v.

All the intermediate products and exemplary compounds were analytically characterised by means of ¹H-NMR spectroscopy. In addition, mass spectrometry tests (MS, m/z for Synthesis of Exemplary Compounds Synthesis of Example 1

2-Ethylsulfanyl-N-[(3-fluorophenyl)-methyl]-4-methyl-7-(trifluoromethyl)-[1,5]naphthyridine-3-carboxylic acid amide

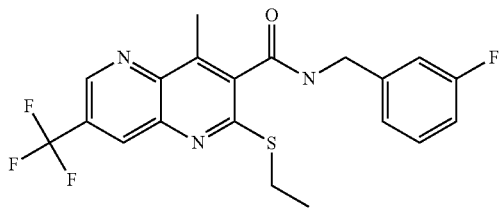 [SMILES: CCSc1nc2cc(C(F)(F)F)cnc2c(C)c1C(=O)NCc1cccc(F)c1]

a) Synthesis of ethyl 3-(2-acetyl-5-(trifluoromethyl)pyridin-3-ylamino)-3-oxopropanoate To a solution of 1-(3-amino-5-(trifluoromethyl)pyridin-2-yl)ethanone (0.87 g, 4.26 mmol, 1 eq.) in DCM (20 ml) were added TEA (0.65 ml, 4.69 mmol, 1.1 eq.) and ethyl 3-chloro-3-oxopropanoate (0.71 ml, 5.54 mmol, 1.3 eq.) at 0° C. The reaction mixture was stirred at RT for 3 h. Then the mixture was diluted with water (50 ml) and extracted with DCM (3×80 ml). The combined organic layers were washed with water (80 ml), dried over anhydrous $Na_2SO_4$ and concentrated in vacuo to provide ethyl 3-(2-acetyl-5-(trifluoromethyl)pyridin-3-ylamino)-3-oxopropanoate (1.35 g, 4.24 mmol, 99%) which was used in subsequent reactions without further purification.

b) Synthesis of ethyl 2-hydroxy-4-methyl-7-(trifluoromethyl)-1,5-naphthyridine-3-carboxylate To a cooled (ice water batch) suspension of ethyl 3-(2-acetyl-5-(trifluoromethyl)pyridin-3-ylamino)-3-oxopropanoate (1.35 g, 4.24 mmol, 1 eq.) in ethanol (15 ml) was added NaH (60% w/w suspension in oil, 0.19 g, 4.66 mmol, 1.1 eq.) portion wise. The reaction mixture was stirred at RT for 1 h. Then the reaction was quenched with water (20 ml) and ethanol was distilled off. The residue was acidified with 5M aq. HCl (pH~4) and was extracted with EtOAc (3×100 ml). The combined organic layers were washed with brine (100 ml), dried over anhydrous $Na_2SO_4$ and evaporated to provide the crude product, which was triturated with DCM (2×30 ml) to yield ethyl 2-hydroxy-4-methyl-7-(trifluoromethyl)-1,5-naphthyridine-3-carboxylate (1.05 g, 3.50 mmol, 82%).

c) Synthesis of ethyl 2-chloro-4-methyl-7-(trifluoromethyl)-1,5-naphthyridine-3-carboxylate To ethyl 2-hydroxy-4-methyl-7-(trifluoromethyl)-1,5-naphthyridine-3-carboxylate (1.05 g, 3.50 mmol, 1 eq.) was added $POCl_3$ (11 ml) at RT and the reaction mixture was heated to reflux at 110° C. for 3 h. Afterwards excess $POCl_3$ was distilled off and the residue was diluted with EtOAc (50 ml). The mixture was washed with a sat. solution of $NaHCO_3$ (50 ml), water (50 ml), brine (50 ml), dried over anhydrous $Na_2SO_4$ and evaporated to provide ethyl 2-chloro-4-methyl-7-(trifluoromethyl)-1,5-naphthyridine-3-carboxylate (0.98 g, 3.08 mmol, 88%), which was used in subsequent reactions without further purification.

d) Synthesis of ethyl 2-(ethylthio)-4-methyl-7-(trifluoromethyl)-1,5-naphthyridine-3-carboxylate To a solution of ethyl 2-chloro-4-methyl-7-(trifluoromethyl)-1,5-naphthyridine-3-carboxylate (0.97 g, 3.05 mmol, 1 eq.) in DMF (10 ml) were added $K_2CO_3$ (1.26 g, 9.15 mmol, 3 eq.) and ethanethiol (0.66 ml, 9.15 mmol, 3 eq.) at RT. The mixture was stirred at 60° C. for 16 h. Afterwards the mixture was diluted with water (80 ml) and was extracted with EtOAc (3×80 ml). The combined organic layers were washed with water (100 ml), brine (100 ml), dried over anhydrous $Na_2SO_4$ and evaporated to provide the crude product, which is purified by CC (EtOAc/hexane 1:9) to yield ethyl 2-(ethylthio)-4-methyl-7-(trifluoromethyl)-1,5-naphthyridine-3-carboxylate (0.75 g, 2.18 mmol, 71%).

e) Synthesis of 2-Ethylsulfanyl-N-[(3-fluorophenyl)-methyl]-4-methyl-7-(trifluoromethyl)-[1,5]naphthyridine-3-carboxylic acid amide To a solution of ethyl 2-(ethylthio)-4-methyl-7-(trifluoromethyl)-1,5-naphthyridine-3-carboxylate (0.20 g, 0.58 mmol, 1 eq.) in toluene (6 ml) were added $Me_3Al$ (2M solution in toluene, 1.16 ml, 2.32 mmol, 4 eq.) and (3-fluorophenyl)methanamine (0.27 ml, 2.32 mmol, 4 eq.) at RT. The reaction mixture was stirred at 110° C. for 16 h. Afterwards the mixture was diluted with water (50 ml) and was extracted with EtOAc (3×40 ml). The combined organic layers were washed with a 0.5 M aq. HCl (60 ml), brine (60 ml), dried over anhydrous $Na_2SO_4$ and evaporated to provide the crude product, which was purified by CC (EtOAc/hexane 1:4) to yield 2-Ethylsulfanyl-N-[(3-fluorophenyl)-methyl]-4-methyl-7-(trifluoromethyl)-[1,5]naphthyridine-3-carboxylic acid amide (example 1) (0.14 g, 0.33 mmol, 57%). MS m/z $[M+H]^+$ 424.1.

Synthesis of Example 2

2-Ethylsulfanyl-N-[(3-fluorophenyl)-methyl]-4-methyl-[1,7]naphthyridine-3-carboxylic acid amide

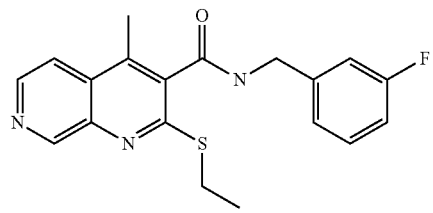 [SMILES: CCSc1nc2cnccc2c(C)c1C(=O)NCc1cccc(F)c1]

a) Synthesis of 2-(ethylthio)-4-methyl-1,7-naphthyridine-3-carboxylic acid

To a solution of ethyl 2-(ethylthio)-4-methyl-1,7-naphthyridine-3-carboxylate [synthesized according to the methods described for example 1, sections a-d] (2.30 g, 8.33 mmol, 1 eq) in a mixture of THF (30 ml) and methanol (15 ml) was added a solution of $LiOH\cdot H_2O$ (3.50 g, 83.33 mmol, 10 eq) in water (7.5 ml) at RT. The resulting mixture was stirred at 75°

C. for 5 h. Afterwards the solvents were evaporated and the residue was washed with EtOAc (80 ml). The aq. layer was acidified with a 4M aq. HCl (50 ml) and extracted with EtOAc (3×100 ml). The combined organic layers were washed with water (100 ml), brine (100 ml), dried over anhydrous Na$_2$SO$_4$ and evaporated to provide 2-(ethylthio)-4-methyl-1,7-naphthyridine-3-carboxylic acid (0.85 g, 3.43 mmol, 41%) which was used in subsequent reactions without further purification.

b) Synthesis of 2-Ethylsulfanyl-N-[(3-fluorophenyl)-methyl]-4-methyl-[1,7]naphthyridine-3-carboxylic acid amide To a solution of 2-(ethylthio)-4-methyl-1,7-naphthyridine-3-carboxylic acid (0.25 g, 1.01 mmol, 1 eq) in dry THF (12 ml) were added HATU (0.42 g, 1.11 mmol, 1.1 eq) and TEA (0.4 ml, 3.03 mmol, 3 eq) at RT and the reaction mixture was stirred at RT for 15 min. 3-fluorophenyl)methanamine (0.16 g, 1.26 mmol, 1.25 eq) was added to the mixture at RT and the reaction mixture was stirred at RT for 1 h. Afterwards the excess solvent was distilled off and the residue was diluted with a sat. aq. solution of NH$_4$Cl (50 ml). The aq. part was extracted with EtOAc (3×80 ml). The combined organic layers were washed with a sat. aq. solution of NaHCO$_3$ (50 ml), water (50 ml), dried over anhydrous Na$_2$SO$_4$ and evaporated to provide the crude product, which was purified by CC (acetone/hexane 2:9) to yield 2-Ethylsulfanyl-N-[(3-fluorophenyl)-methyl]-4-methyl-[1,7]naphthyridine-3-carboxylic acid amide (example 2) (0.18 g, 0.51 mmol, 50%). MS m/z [M+H]$^+$ 356.1.

Synthesis of Example 3

2-Ethylsulfanyl-N-[(4-fluorophenyl)-methyl]-4-methyl-[1,6]naphthyridine-3-carboxylic acid amide

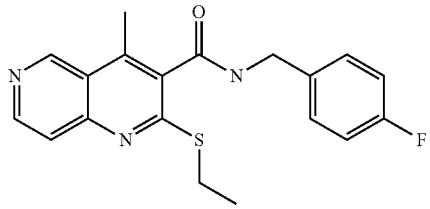 [SMILES: CCSc1nc2ccncc2c(C)c1C(=O)NCc1ccc(F)cc1]

a) Synthesis of ethyl 2-mercapto-4-methyl-1,6-naphthyridine-3-carboxylate

To a solution of ethyl 2-hydroxy-4-methyl-1,6-naphthyridine-3-carboxylate [synthesized according to the methods described for example 1, sections a and b] (0.35 g, 1.51 mmol, 1 eq.) in a mixture of pyridine/toluene (1:9 v/v, 15 ml) was added LR (2.44 g, 6.03 mmol, 4 eq.) at RT and the reaction mixture was heated to reflux at 110° C. for 22 h. Afterwards the mixture was cooled to RT and was quenched with a sat. aq. solution of NaHCO$_3$ (5 ml). The aq. part was extracted with EtOAc (3×30 ml). The combined organic layers were washed with water (30 ml), brine (30 ml), dried over anhydrous Na$_2$SO$_4$ and evaporated to provide the crude product which is purified by CC (methanol/DCM 1:99) to yield ethyl 2-mercapto-4-methyl-1,6-naphthyridine-3-carboxylate (0.22 g, 0.89 mmol, 59%).

b) Synthesis of ethyl 2-(ethylthio)-4-methyl-1,6-naphthyridine-3-carboxylate

To a solution of ethyl 2-mercapto-4-methyl-1,6-naphthyridine-3-carboxylate (0.22 g, 0.89 mmol, 1 eq.) in dry DMF (5 ml) was added K$_2$CO$_3$ (0.37 g, 2.66 mmol, 3 eq.) at 0° C. followed by the addition of ethyl iodide (0.41 g, 2.66 mmol, 3 eq.). The reaction mixture was stirred at RT for 1 h. Afterwards the mixture was poured into ice water (10 ml) and extracted with EtOAc (3×20 ml). The combined organic layers were washed with water (20 ml), brine (20 ml), dried over anhydrous Na$_2$SO$_4$ to provide the crude product, which was purified by CC (EtOAc/hexane 2:3) to yield ethyl 2-(ethylthio)-4-methyl-1,6-naphthyridine-3-carboxylate (0.18 g, 0.65 mmol, 73%).

c) Synthesis of 2-Ethylsulfanyl-N-[(4-fluorophenyl)-methyl]-4-methyl-[1,6]naphthyridine-3-carboxylic acid amide 2-Ethylsulfanyl-N-[(4-fluorophenyl)-methyl]-4-methyl-[1,6]naphthyridine-3-carboxylic acid amide (example 3) (0.18 g, 0.51 mmol, 50%) was synthesized from Ethyl 2-(ethylthio)-4-methyl-1,6-naphthyridine-3-carboxylate (0.20 g, 0.72 mmol, 1 eq.) according to the method described for example 1, section e. MS m/z [M+H]$^+$ 356.1.

Synthesis of Example 4

6-Ethylsulfanyl-N-[(3-fluorophenyl)-methyl]-4-methyl-thieno[2,3-b]pyridine-5-carboxylic acid amide

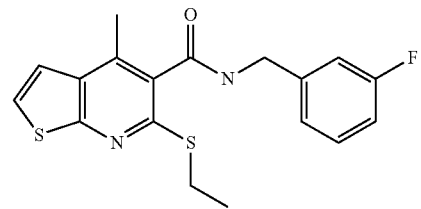 [SMILES: CCSc1nc2sccc2c(C)c1C(=O)NCc1cccc(F)c1]

a) Synthesis of ethyl 4-methyl-6-(trifluoromethylsulfonyloxy)thieno[2,3-b]pyridine-5-carboxylate To a solution of ethyl 6-hydroxy-4-methylthieno[2,3-b]pyridine-5-carboxylate [synthesized according to the methods described for example 1, sections a and b] (1.00 g, 4.21 mmol, 1 eq.) in DCM (35 ml) were added TEA (1.16 ml, 8.43 mmol, 2 eq.) and triflic anhydride (1.16 ml, 8.43 mmol, 2 eq.) at 0° C. The RM was stirred at RT for 2 h. Afterwards the mixture was diluted with DCM (100 ml) and the organic layer was washed with a sat. aq. NaHCO$_3$ solution (50 ml), water (50 ml) and brine (50 ml). The organic layer was dried over Na$_2$SO$_4$ and evaporated under reduced pressure. The crude ethyl 4-methyl-6-(trifluoro-methyl-sulfonyloxy)thieno[2,3-b]pyridine-5-carboxylate (1.55 g, 4.21 mmol, 99%) was used in subsequent reactions without further purification.

b) Synthesis of ethyl 6-(ethylthio)-4-methylthieno[2,3-b]pyridine-5-carboxylate

To a solution of ethyl 4-methyl-6-(trifluoro-methyl-sulfonyloxy)thieno[2,3-b]pyridine-5-carboxylate (1.84 g, 4.9 mmol, 1 eq.) in DMF (30 ml) were added K$_2$CO$_3$ (2.70 g, 19.6 mmol, 4 eq.) and ethanethiol (3.73 ml, 49.8 mmol, 10 eq.) at RT. The reaction mixture was stirred at 80° C. for 2 h. Afterwards the mixture was diluted with water (50 ml) and was extracted with EtOAc (2×50 ml). The combined organic layers were washed with water (50 ml), brine (50 ml), dried over $Na_2SO_4$ and evaporated. The crude product was purified by CC (EtOAc/hexane 1:49) to yield ethyl 6-(ethylthio)-4-methylthieno[2,3-b]pyridine-5-carboxylate (0.26 g, 0.92 mmol, 19%).

c) Synthesis of 6-Ethylsulfanyl-N-[(3-fluorophenyl)-methyl]-4-methyl-thieno[2,3-b]pyridine-5-carboxylic acid amide 6-Ethylsulfanyl-N-[(3-fluorophenyl)-methyl]-4-methyl-thieno[2,3-b]pyridine-5-carboxylic acid amide (example 4) (0.23 g, 0.64 mmol, 63%) was synthesized from ethyl 6-(ethylthio)-4-methylthieno[2,3-b]pyridine-5-carboxylate (0.29 g, 1.01 mmol, 1 eq.) according to the method described for example 1, section e. MS m/z [M+H]$^+$ 361.1.

Synthesis of Example 5

5-Ethoxy-N-[(3-fluorophenyl)-methyl]-7-methyl-2-(trifluoromethyl)-thieno[3,2-b]pyridine-6-carboxylic acid amide

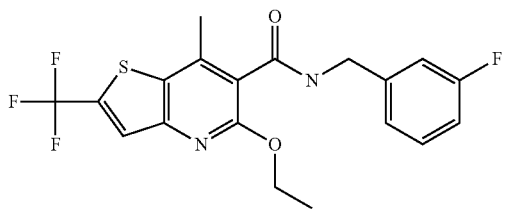 [SMILES: CCOc1nc2cc(C(F)(F)F)sc2c(C)c1C(=O)NCc1cccc(F)c1]

a) Synthesis of ethyl 5-ethoxy-7-methyl-2-(trifluoromethyl)thieno[3,2-b]pyridine-6-carboxylate To a suspension N-(3-fluorobenzyl)-5-hydroxy-7-methyl-2-(trifluoromethyl)thieno[3,2-b]pyridine-6-carboxamide (0.40 g, 1.31 mmol, 1 eq.) [synthesized according to the methods described for example 1, sections a and b] in a mixture DCM (10 ml) and DMF (0.5 ml) was added $Ag_2CO_3$ (0.90 g, 3.28 mmol, 2.5 eq.) at RT followed by the addition of ethyl iodide (0.54 ml, 6.55 mmol, 5 eq.). The resulting mixture was stirred at RT for 20 h. Afterwards the reaction mass was filtered through celite. The filtrate was extracted with DCM and the DCM layer was concentrated in vacuo to provide the crude product, which was purified by CC (EtOAc/hexane 1:17) to yield ethyl 5-ethoxy-7-methyl-2-(trifluoromethyl)thieno[3,2-b]pyridine-6-carboxylate (0.37 g, 1.11 mmol, 84%).

b) Synthesis of 5-Ethoxy-N-[(3-fluorophenyl)-methyl]-7-methyl-2-(trifluoromethyl)-thieno[3,2-b]pyridine-6-carboxylic acid amide 5-Ethoxy-N-[(3-fluorophenyl)-methyl]-7-methyl-2-(trifluoromethyl)-thieno[3,2-b]pyridine-6-carboxylic acid amide (example 5) (0.20 g, 0.48 mmol, 44%) was synthesized from ethyl 5-ethoxy-7-methyl-2-(trifluoromethyl)thieno[3,2-b]pyridine-6-carboxylate (0.37 g, 1.11 mmol, 1 eq.) according to the method described for example 1, section e. MS m/z [M+H]$^+$ 413.1.

Synthesis of Further Exemplary Compounds

The synthesis of further examples was carried out according to the methods already described. Table 1 shows which compound was produced according to which method. It is evident to the person skilled in the art which educts and reagents were used in each case.

TABLE 1

| Example | Chemical Name | Preparation in analogy to example | MS m/z [M + H]$^+$ | Yield [g] | Yield [%] (final step) |
|---|---|---|---|---|---|
| 6 | 2-Ethylsulfanyl-N-[(3-fluorophenyl)-methyl]-4-methyl-7-(trifluoromethyl)-[1,8]naphthyridine-3-carboxylic acid amide | 1 | 424.1 | 0.06 | 48 |
| 7 | 2-Ethylsulfanyl-N-[(4-fluorophenyl)-methyl]-4-methyl-7-(trifluoromethyl)-[1,8]naphthyridine-3-carboxylic acid amide | 1 | 424.1 | 0.10 | 81 |
| 8 | 2-Ethylsulfanyl-N-[(3-fluorophenyl)-methyl]-4-methyl-[1,5]naphthyridine-3-carboxylic acid amide | 1 | 356.1 | 0.09 | 69 |
| 9 | 2-Ethylsulfanyl-N-[(4-fluorophenyl)-methyl]-4-methyl-[1,5]naphthyridine-3-carboxylic acid amide | 1 | 356.1 | 0.15 | 46 |
| 10 | 2-Ethylsulfanyl-N-[(4-fluorophenyl)-methyl]-4-methyl-7-(trifluoromethyl)-[1,5]naphthyridine-3-carboxylic acid amide | 1 | 424.1 | 0.18 | 48 |
| 11 | 2-Ethylsulfanyl-N-[(3-fluorophenyl)-methyl]-4-methyl-7-(trifluoromethyl)-[1,6]naphthyridine-3-carboxylic acid amide | 1 | 424.1 | 0.22 | 81 |
| 12 | 2-Ethylsulfanyl-N-[(4-fluorophenyl)-methyl]-4-methyl-7-(trifluoromethyl)-[1,6]naphthyridine-3-carboxylic acid amide | 1 | 424.1 | 0.30 | 91 |
| 13 | 2-Ethylsulfanyl-N-[(3-fluorophenyl)-methyl]-4-methyl-[1,6]naphthyridine-3-carboxylic acid amide | 1 | 356.1 | 0.11 | 66 |
| 14 | 5-Ethylsulfanyl-N-[(3-fluorophenyl)-methyl]-7-methyl-thieno[3,2-b]pyridine-6-carboxylic acid amide | 1 | 361.1 | 0.09 | 62 |

TABLE 1-continued

| Example | Chemical Name | Preparation in analogy to example | MS m/z [M + H]$^+$ | Yield [g] | Yield [%] (final step) |
|---|---|---|---|---|---|
| 15 | 2-Ethylsulfanyl-N-[(4-fluorophenyl)-methyl]-4-methyl-[1,7]naphthyridine-3-carboxylic acid amide | 2 | 356.1 | 0.11 | 42 |
| 16 | 2-Ethylsulfanyl-N-[(4-fluorophenyl)-methyl]-4-methyl-[1,8]naphthyridine-3-carboxylic acid amide | 2 | 356.1 | 0.11 | 26 |
| 17 | 2-Ethylsulfanyl-N-[(3-fluorophenyl)-methyl]-4-methyl-[1,8]naphthyridine-3-carboxylic acid amide | 2 | 356.1 | 0.11 | 26 |
| 18 | 6-Ethoxy-N-[(3-fluorophenyl)-methyl]-4-methyl-2-(trifluoromethyl)-thieno[2,3-b]pyridine-5-carboxylic acid amide | 5 | 413.1 | 0.05 | 46 |

Pharmacological Experiments

Method I. Fluorescence Assay Using a Voltage Sensitive Dye

Human CHO—K1 cells expressing KCNQ2/3 channels are cultivated adherently at 37° C., 5% $CO_2$ and 95% humidity in cell culture bottles (e.g. 80 cm$^2$ TC flasks, Nunc) with DMEM-high glucose (Sigma Aldrich, D7777) including 10% FCS (PAN Biotech, e.g. 3302-P270521) or alternatively MEM Alpha Medium (lx, liquid, Invitrogen, #22571), 10% fetal calf serum (FCS) (Invitrogen, #10270-106, heat-inactivated) and the necessary selection antibiotics.

Before being sown out for the measurements, the cells are washed with a 1×DPBS buffer without $Ca^{2+}/Mg^{2+}$ (e.g. Invitrogen, #14190-094) and detached from the bottom of the culture vessel by means of Accutase (PAA Laboratories, #L11-007) (incubation with Accutase for 15 min at 37° C.). The cell count then present is determined using a CASY™ cell counter (TCC model, Scharfe System) in order subsequently to apply, depending on the density optimization for the individual cell line, 20,000-30,000 cells/well/100 µl of the described nutrient medium to 96-well measuring plates of the Corning™ CellBIND™ type (Flat Clear Bottom Black Polystyrene Microplates, #3340). Incubation is then carried out for one hour at room temperature, without gassing or adjusting the humidity, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, MDS Analytical Technologies™) is prepared by dissolving the contents of a vessel Membrane Potential Assay Kit Red Component A in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed with 200 µl of ES buffer, then covered with a layer of 100 µl of the dye solution prepared above and incubated for 45 min at room temperature with the exclusion of light.

The fluorescence measurements are carried out with a BMG Labtech FLUOstar™, BMG Labtech NOVOstar™ or BMG Labtech POLARstar™ instrument (525 nm excitation, 560 nm emission, Bottom Read mode). After incubation of the dye, 50 µl of the test substances in the desired concentrations, or 50 µl of ES buffer for control purposes, are introduced into separate cavities of the measuring plate and incubated for 30 min at room temperature while being shielded from light. The fluorescence intensity of the dye is then measured for 5 min and the fluorescence value $F_1$ of each well is thus determined at a given, constant time. 15 µl of a 100 mM KCl solution (final concentration 92 mM) are then added to each well. The change in fluorescence is subsequently measured until all the relevant measured values have been obtained (mainly 5-30 min). At a given time after KCl application, a fluorescence value $F_2$ is determined, in this case at the time of the fluorescence peak.

For calculation, the fluorescence intensity $F_2$ is corrected for the fluorescence intensity $F_1$, and the activity ($\Delta F/F$) of the target compound on the potassium channel is determined as follows:

$$\left(\frac{F_2 - F_1}{F_1}\right) \times 100 = \frac{\Delta F}{F}(\%)$$

In order to determine whether a substance has agonistic activity, $$\frac{\Delta F}{F}$$

can be related to $$\left(\frac{\Delta F}{F}\right)_K$$

of control wells.

$$\left(\frac{\Delta F}{F}\right)_K$$

is determined by adding to the well only the buffer solution instead of the test substance, determining the value $F_{1K}$ of the fluorescence intensity, adding the potassium ions as described above, and measuring a value $F_{2K}$ of the fluorescence intensity. $F_{2K}$ and $F_{1K}$ are then calculated as follows:

$$\left(\frac{F_{2K} - F_{1K}}{F_{1K}}\right) \times 100 = \left(\frac{\Delta F}{F}\right)_K (\%)$$

A substance has an agonistic activity on the potassium channel if $$\frac{\Delta F}{F}$$

is greater than $$\left(\frac{\Delta F}{F}\right)_K : \frac{\Delta F}{F} > \left(\frac{\Delta F}{F}\right)_K$$

Independently of the comparison of $$\frac{\Delta F}{F} \text{ with } \left(\frac{\Delta F}{F}\right)_K$$

it is possible to conclude that a target compound has agonistic activity if $$\frac{\Delta F}{F}$$

increases dose dependently.

Calculations of $EC_{50}$ and $IC_{50}$ values are carried out with the aid of 'Prism v4.0' software (GraphPad Software™)

Method II. Low-Intensity Tail Flick Test (Rat)

In the low-intensity tail flick test, the determination of the antinociceptive effect of the compounds according to the invention towards an acute noxious thermal stimulus is carried out by measuring the withdrawal reflex of the rat tail (tail flick) in response to a radiant heat beam (analgesia meter; model 2011 of the company Rhema Labortechnik, Hofheim, Germany) according to the method described by D'Amour and Smith (J. Pharm. Exp. Ther. 72, 74 79 (1941). To this end, the rats were placed in a plexiglas restrainer, and a low-intensity radiant heat beam (48° C.) was focused onto the dorsal surface of the tail root. The stimulus intensity was adjusted to result in a mean pre-drug control withdrawal latency of about 7 s, thus also allowing a supraspinal modulation of the spinally mediated acute nociceptive reflex. A cutoff time of 30 s was applied to avoid tissue damage. Male Sprague-Dawley rats (Janvier, Le Genest St. Isle, Frankreich) with weights of 200-250 g were used. 10 rats were used per group. Before administration of a compound according to the invention, the animals were pre-tested twice in the course of five minutes and the mean of these measurements was calculated as the pre-test mean. The antinociceptive effect was determined at 20, 40 and 60 min after peroral compound administration. The antinociceptive effect was calculated based on the increase in the tail withdrawal latency according to the following formula and is expressed as percentage of the maximum possible effect (MPE [%]):

$$MPE = [(T_1 - T_0)/(T_2 - T_0)] * 100$$

In this, $T_0$ is the control latency time before and $T_1$ the latency time after administration of the compound, $T_2$ is the cutoff time and MPE is the maximum possible effect. Employing variant analysis (repeated measures ANOVA) allowed testing of statistically significant differences between the compounds according to the invention and the vehicle group. The significance level was set to $p \leq 0.05$.

Pharmacological Data

The pharmacological effects of the compounds according to the invention were determined as described hereinbefore (pharmacological experiments, methods I and II respectively).

The corresponding pharmacological data are summarized in Table 2.

TABLE 2

| Example | Fluorimetry % efficacy (retigabine = 100%) | Fluorimetry $EC_{50}$ [nM] | Low intensity tail flick, rat, peroral, $ED_{50}$ or MPE (dose) [mg/kg] |
|---|---|---|---|
| 1 | 156 | 84 | |
| 2 | 62 | 2193 | |
| 3 | 34 | | |
| 4 | 31 | | |
| 5 | 121 | 51 | |
| 6 | 152 | 683 | |
| 7 | 132 | 412 | 16 (10) |
| 8 | 9 | | |
| 9 | 6 | | |
| 10 | 148 | 101 | |
| 11 | 101 | 201 | |
| 12 | 97 | 301 | |
| 13 | 32 | | |
| 14 | −39 | 650 | |
| 15 | 34 | | |
| 16 | 10 | | |
| 17 | 10 | | |
| 18 | 112 | 63 | |

The invention claimed is:

1. A compound of general formula (I)

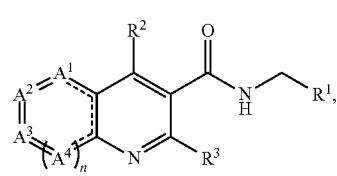

(I)

wherein
$A^1$, $A^2$ and $A^3$ independently of each other represent $CR^4$, N, O, S or $N(CH_3)$,
$A^4$ represents $CR^4$ or N, and
n denotes 0 or 1,
with the proviso, that
at least one of $A^1$, $A^2$, $A^3$ and $A^4$ does not represent $CR^4$, and with the proviso, that
if n denotes 0, then precisely one of $A^1$, $A^2$ and $A^3$ represents O, S or $N(CH_3)$, or
if n denotes 1, then $A^1$, $A^2$ and $A^3$ independently of each other represent $CR^4$ or N,
$R^1$ represents $C_{1-10}$-aliphatic residue, unsubstituted or mono- or polysubstituted; $C_{3-10}$-cycloaliphatic residue or 3 to 10 membered heterocycloaliphatic residue, in each case unsubstituted or mono- or polysubstituted and in each case optionally linked via a $C_{1-8}$-aliphatic group, which in turn may be unsubstituted or mono- or polysubstituted; aryl or heteroaryl, in each case unsubstituted or mono- or polysubstituted and in each case optionally linked via a $C_{1-8}$-aliphatic group, which in turn may be unsubstituted or mono- or polysubstituted;
$R^2$ represents F; Cl; Br; I; CN; $CF_3$; C(=O)H; $NO_2$; $OCF_3$; $SCF_3$; $C_{1-4}$-aliphatic residue, C(=O)—$C_{1-4}$-aliphatic residue, C(=O)—O—$C_{1-4}$-aliphatic residue, C(=O)—NH—$C_{1-4}$-aliphatic residue, C(=O)—N($C_{1-4}$-aliphatic residue)$_2$, O—$C_{1-4}$-aliphatic residue, O—C(=O)—$C_{1-4}$-aliphatic residue, S—$C_{1-4}$-aliphatic residue, S(=O)$_2$—$C_{1-4}$-aliphatic residue, S(=O)$_2$—O—$C_{1-4}$-aliphatic residue, wherein the $C_{1-4}$-aliphatic residue may be in each case be unsubstituted or mono- or polysubstituted;

$C_{3-6}$-cycloaliphatic residue or 3 to 7 membered heterocycloaliphatic residue, in each case unsubstituted or mono- or polysubstituted and in each case optionally linked via a $C_{1-4}$-aliphatic group, which in turn may be unsubstituted or mono- or polysubstituted;

$R^3$ represents $C_{2-10}$-aliphatic residue, unsubstituted or mono- or polysubstituted; $C_{3-10}$-cycloaliphatic residue or 3 to 10 membered heterocycloaliphatic residue, in each case unsubstituted or mono- or polysubstituted and in each case optionally linked via a $C_{1-8}$-aliphatic group, which in turn may be unsubstituted or mono- or polysubstituted, or denotes S—$R^5$, O—$R^6$ or N($R^7 R^8$), wherein $R^5$ and $R^6$ in each case represent $C_{1-10}$-aliphatic residue, unsubstituted or mono- or polysubstituted; $C_{3-10}$-cycloaliphatic residue or 3 to 10 membered heterocycloaliphatic residue, in each case unsubstituted or mono- or polysubstituted and in each case optionally linked via a $C_{1-8}$-aliphatic group, which in turn may be unsubstituted or mono- or polysubstituted;

with the proviso, that if $R^5$ or $R^6$ denote a 3 to 10 membered heterocycloaliphatic residue, than the 3 to 10 membered heterocycloaliphatic residue is linked via a carbon atom, $R^7$ represents $C_{1-10}$-aliphatic residue, unsubstituted or mono- or polysubstituted; $C_{3-10}$-cycloaliphatic residue or 3 to 10 membered heterocycloaliphatic residue, in each case unsubstituted or mono- or polysubstituted and in each case optionally linked via a $C_{1-8}$-aliphatic group, which in turn may be unsubstituted or mono- or polysubstituted;

with the proviso that if $R^7$ denotes 3 to 10 membered heterocycloaliphatic residue, the 3 to 10 membered heterocycloaliphatic residue is linked via a carbon atom; and $R^8$ denotes $C_{1-10}$-aliphatic residue, unsubstituted or mono- or polysubstituted;

or $R^7$ and $R^8$ form together with the nitrogen atom connecting them a 3 to 10 membered heterocycloaliphatic residue, unsubstituted or mono- or polysubstituted;

and each $R^4$ independently represents H, F; Cl; Br; I; CN; CF$_3$; CHF$_2$; CH$_2$F; OCF$_3$; OCHF$_2$; OCH$_2$F; SCF$_3$; O—$C_{1-4}$-aliphatic residue, $C_{1-4}$-aliphatic residue or S(=O)$_2$—$C_{1-4}$-aliphatic residue;

in which an "aliphatic group" and "aliphatic residue" may in each case be branched or unbranched, saturated or unsaturated, in which a "cycloaliphatic residue" and a "heterocycloaliphatic residue" may in each case be saturated or unsaturated, in which "mono- or polysubstituted" with respect to an "aliphatic group", an "aliphatic residue", a "cycloaliphatic residue" and a "heterocycloaliphatic residue" relates, with respect to the corresponding residues or groups, to the substitution of one or more hydrogen atoms each independently of one another by at least one substituent selected from the group consisting of F, Cl, Br, I, NO$_2$, NH$_2$, NH($C_{1-4}$-aliphatic residue), N($C_{1-4}$-aliphatic residue)$_2$, NH—C(=O)—$C_{1-4}$ aliphatic residue, N($C_{1-4}$ aliphatic residue)-C(=O)—$C_{1-4}$ aliphatic residue, NH—S(=O)$_2$—$C_{1-4}$ aliphatic residue, N($C_{1-4}$ aliphatic residue)-S(=O)$_2$—$C_{1-4}$ aliphatic residue, =O, OH, OCF$_3$, O—$C_{1-4}$-aliphatic residue, O—C(=O)—$C_{1-4}$-aliphatic residue, SH, SCF$_3$, S—$C_{1-4}$-aliphatic residue, S(=O)$_2$OH, S(=O)$_2$—$C_{1-4}$-aliphatic residue, S(=O)$_2$—O—$C_{1-4}$-aliphatic residue, S(=O)$_2$—NH($C_{1-4}$-aliphatic residue), S(=O)$_2$—N($C_{1-4}$-aliphatic residue)$_2$, CN, CF$_3$, CHO, COON, $C_{1-4}$-aliphatic residue, C(=O)—$C_{1-4}$-aliphatic residue, C(=O)—O—$C_{1-4}$-aliphatic residue, $C_{3-6}$-cycloaliphatic residue, 3 to 7 membered heterocycloaliphatic residue, C(=O)NH$_2$, a C(=O)—NH($C_{1-4}$-aliphatic residue) and C(=O)—N($C_{1-4}$-aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO$_2$, NH$_2$,

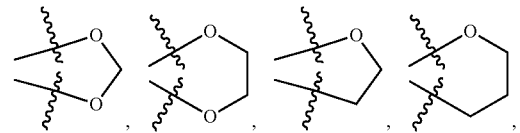

NH($C_{1-4}$-aliphatic residue), N($C_{1-4}$-aliphatic residue)$_2$, NH—C(=O)—$C_{1-4}$-aliphatic residue, N($C_{1-4}$ aliphatic residue)-C(=O)—$C_{1-4}$ aliphatic residue, NH—S(=O)$_2$—$C_{1-4}$ aliphatic residue, N($C_{1-4}$ aliphatic residue)-S(=O)$_2$—$C_{1-4}$ aliphatic residue, OH, OCF$_3$, O—$C_{1-4}$-aliphatic residue, O—C(=O)—$C_{1-4}$-aliphatic residue, SH, SCF$_3$, S—$C_{1-4}$-aliphatic residue, S(=O)$_2$OH, S(=O)$_2$—$C_{1-4}$-aliphatic residue, S(=O)$_2$—O—$C_{1-4}$-aliphatic residue, S(=O)$_2$—NH($C_{1-4}$-aliphatic residue), S(=O)$_2$—N($C_{1-4}$-aliphatic residue)$_2$, CN, CF$_3$, C(=O)H, C(=O)OH, $C_{1-4}$-aliphatic residue, C(=O)—$C_{1-4}$-aliphatic residue, C(=O)—O—$C_{1-4}$-aliphatic residue, $C_{3-6}$-cycloaliphatic residue, 3 to 7 membered heterocycloaliphatic residue, benzyl, aryl, heteroaryl, C(=O)NH$_2$, C(=O)—NH($C_{1-4}$-aliphatic residue) and C(=O)—N($C_{1-4}$-aliphatic residue)$_2$;

in the form of an individual single stereoisomer or a mixture of the stereoisomers in any mixing ratio, and/or in the form of a free compound, a solvate and and/or a physiologically acceptable salt.

2. The compound according to claim 1, wherein $A^1$, $A^2$ and $A^3$ independently of each other represent CR$^4$, N, O, S or N(CH$_3$), $A^4$ represents CR$^4$ or N, and n denotes 0 or 1, with the proviso, that at least one of $A^1$, $A^2$, $A^3$ and $A^4$ does not represent CR$^4$, and with the proviso, that if n denotes 0, then precisely one of $A^1$, $A^2$ and $A^3$ represents O, S or N(CH$_3$), or if n denotes 1, then $A^1$, $A^2$ and $A^3$ independently of each other represent CR$^4$ or N, $R^1$ denotes $C_{1-10}$-aliphatic residue, unsubstituted or mono- or polysubstituted with at least one substituent selected from the group consisting of F, Cl, Br, I, NO$_2$, NH$_2$, NH($C_{1-4}$-aliphatic residue), N($C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue,
or denotes $C_{3-10}$-cycloaliphatic residue or 3 to 10 membered heterocycloaliphatic residue, in each case unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)—OH, $C_{3-6}$-cycloaliphatic residue and 3 to 7 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and
wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
and wherein the $C_{3-10}$-cycloaliphatic residue or the 3 to 10 membered heterocycloaliphatic residue may in each case optionally linked via a $C_{1-8}$-aliphatic group, which in turn may be unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
or denotes aryl or heteroaryl, in each case unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$, C(=O)$OC_2H_5$, $C_{3-6}$-cycloaliphatic residue, 3 to 7 membered heterocycloaliphatic residue,

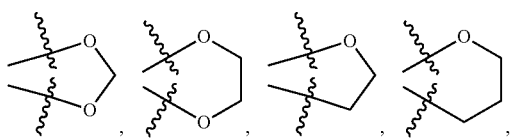

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, O—$C_{1-4}$-aliphatic residue, $OCF_3$, $OCH_2CH_2OH$, $OCH_2OCH_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$ and C(=O)$OC_2H_5$, and
wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
and wherein the aryl or the heteroaryl residue may in each case be optionally linked via a $C_{1-8}$-aliphatic group, which in turn may be unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, =O, O—$C_{1-4}$-aliphatic residue, $OCF_3$, $SCF_3$, S—$C_{1-4}$-aliphatic residue, $CF_3$, CN and C(=O)OH,
$R^2$ represents F; Cl; Br; I; CN; $CF_3$; $NO_2$; $OCF_3$; $SCF_3$; $O_{1-4}$-aliphatic residue, S—$C_{1-4}$-aliphatic residue, O—$C_{1-4}$-aliphatic residue, wherein the $C_{1-4}$-aliphatic residue may be in each case be unsubstituted or mono- or polysubstituted with at least one substituent selected from the group consisting of F, Cl, Br, I, OH, $OCF_3$, $CF_3$ and O—$C_{1-4}$-aliphatic residue,
or
$C_{3-6}$-cycloaliphatic residue or 3 to 7 membered heterocycloaliphatic residue, in each case unsubstituted or mono- or polysubstituted and in each case optionally linked via a $C_{1-4}$-aliphatic group, which in turn may be unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN and C(=O)OH,
$R^3$ denotes $C_{2-10}$-aliphatic residue, unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, or
denotes $C_{3-10}$-cycloaliphatic residue or 3 to 10 membered heterocycloaliphatic residue, in each case unsubstituted or mono- or polysubstituted with at least one substituent selected from the group consisting of F, Cl, Br, I, $NO_2$, $NH_2$, NH($C_{1-4}$-aliphatic residue), N($C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-10}$-cycloaliphatic residue or the 3 to 10 membered heterocycloaliphatic residue may in each case optionally linked via a $C_{1-8}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, or denotes S—$R^5$, O—$R^6$ or $N(R^7R^8)$, wherein $R^5$ and $R^6$ in each case represent $C_{1-10}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, or in each case represent $C_{3-10}$-cycloaliphatic residue or 3 to 10 membered heterocycloaliphatic residue, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)—OH, $C_{3-6}$-cycloaliphatic residue and 3 to 7 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the $C_{3-10}$-cycloaliphatic residue or the 3 to 10 membered heterocycloaliphatic residue may in each case optionally linked via a $C_{1-8}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, on the condition that if $R^5$ or $R^6$ denote a 3 to 10 membered heterocycloaliphatic residue, the 3 to 10 membered heterocycloaliphatic residue is linked via a carbon atom, $R^7$ denotes a $C_{1-10}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)—O—$C_{1-4}$-aliphatic residue and C(=O)OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, C(=O)—O—$C_{1-4}$-aliphatic residue, $C_{3-6}$-cycloaliphatic residue and 3 to 7 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the $C_{3-10}$-cycloaliphatic residue or the 3 to 10 membered heterocycloaliphatic residue may in each case optionally linked via a $C_{1-8}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, C(=O)—O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, on the condition that if $R^7$ denotes a 3 to 10 membered heterocycloaliphatic residue, the 3 to 10 membered heterocycloaliphatic residue is linked via a carbon atom, and $R^8$ denotes $C_{1-10}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, or $R^7$ and $R^8$ form together with the nitrogen atom connecting them a 3 to 10 membered heterocycloaliphatic residue, unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)—OH, C$_{3-6}$-cycloaliphatic residue and 3 to 7 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and O—C$_{1-4}$-aliphatic residue, and wherein the C$_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)OH, and wherein the 3 to 10 membered heterocycloaliphatic residue formed by R$^7$ and R$^8$ together with the nitrogen atom connecting them may optionally be condensed with aryl or heteroaryl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, O—C$_{1-4}$-aliphatic residue, OCF$_3$, SH, SCF$_3$, S—C$_{1-4}$-aliphatic residue, CF$_3$, CN, C$_{1-4}$-aliphatic residue, C(=O)OH, C(=O)CH$_3$, C(=O)C$_2$H$_5$, C(=O)OCH$_3$ and C(=O)OC$_2$H$_5$, C$_{3-6}$-cycloaliphatic residue, 3 to 7 membered heterocycloaliphatic residue,

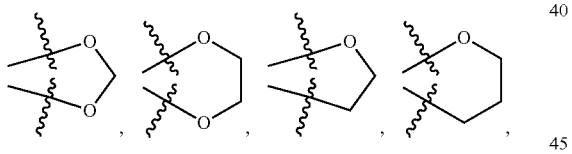

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, O—C$_{1-4}$-aliphatic residue, OCF$_3$, OCH$_2$CH$_2$OH, OCH$_2$OCH$_3$, SH, SCF$_3$, S—C$_{1-4}$-aliphatic residue, CF$_3$, CN, C$_{1-4}$-aliphatic residue, C(=O)OH, C(=O)CH$_3$, C(=O)C$_2$H$_5$, C(=O)OCH$_3$ and C(=O)OC$_2$H$_5$, and wherein the C$_{3-6}$ cycloaliphatic residue and the 3 to 7 membered heterocycloaliphatic residue may in each case may be unsubstituted or mono- or polysubstituted with at least one substituent selected from the group consisting of F, Cl, Br, I, NO$_2$, NH$_2$, NH(C$_{1-4}$-aliphatic residue), N(C$_{1-4}$-aliphatic residue)$_2$, OH, =O, O—C$_{1-4}$-aliphatic residue, OCF$_3$, SH, SCF$_3$, S—C$_{1-4}$-aliphatic residue, CF$_3$, CN, C$_{1-4}$-aliphatic residue and C(=O)—OH, and each R$^4$ independently represents H, F, Cl, Br, I, CN, CF$_3$, CHF$_2$, CH$_2$F, OCF$_3$, OCHF$_2$, OCH$_2$F, SCF$_3$, O—C$_{1-4}$-aliphatic residue, C$_{1-4}$-aliphatic residue or S(=O)$_2$—C$_{1-4}$-aliphatic residue.

3. The compound according to claim 1, wherein
n denotes 1 and A$^1$ represents N, A$^2$ represents CR$^4$, A$^3$ represents CR$^4$ and A$^4$ represents CR$^4$;
or n denotes 1 and A$^1$ represents CR$^4$, A$^2$ represents N, A$^3$ represents CR$^4$ and A$^4$ represents CR$^4$;
or n denotes 1 and A$^1$ represents CR$^4$, A$^2$ represents CR$^4$, A$^3$ represents N and A$^4$ represents CR$^4$;
or n denotes 1 and A$^1$ represents CR$^4$, A$^2$ represents CR$^4$, A$^3$ represents CR$^4$ and A$^4$ represents N;
or n denotes 1 and A$^1$ represents N, A$^2$ represents N, A$^3$ represents CR$^4$ and A$^4$ represents CR$^4$;
or n denotes 1 and A$^1$ represents N, A$^2$ represents CR$^4$, A$^3$ represents N and A$^4$ represents CR$^4$;
or n denotes 1 and A$^1$ represents N, A$^2$ represents CR$^4$, A$^3$ represents CR$^4$ and A$^4$ represents N;
or n denotes 1 and A$^1$ represents CR$^4$, A$^2$ represents N, A$^3$ represents N and A$^4$ represents CR$^4$;
or n denotes 1 and A$^1$ represents CR$^4$, A$^2$ represents N, A$^3$ represents CR$^4$ and A$^4$ represents N;
or n denotes 1 and A$^1$ represents CR$^4$, A$^2$ represents CR$^4$, A$^3$ represents N and A$^4$ represents N;
or n denotes 0 and A$^1$ represents CR$^4$, A$^2$ represents CR$^4$, and A$^3$ represents S;
or n denotes 0 and A$^1$ represents N, A$^2$ represents CR$^4$, and A$^3$ represents S;
or n denotes 0 and A$^1$ represents S, A$^2$ represents CR$^4$ and A$^3$ represents CR$^4$;
or n denotes 0 and A$^1$ represents S, A$^2$ represents CR$^4$ and A$^3$ represents N.

4. The compound according to claim 1, wherein
R$^2$ represents F; Cl; Br; I; CN; CF$_3$; NO$_2$; OCF$_3$; SCF$_3$; C$_{1-4}$-aliphatic residue, S—C$_{1-4}$-aliphatic residue or O—C$_{1-4}$-aliphatic residue,
wherein the C$_{1-4}$-aliphatic residue in each case may be unsubstituted or mono- or polysubstituted with at least one substituent selected from the group consisting of F, Cl, Br, I, =O, OH and O—C$_{1-4}$-aliphatic residue.

5. The compound according to claim 1, wherein
R$^2$ represents C$_{1-4}$-aliphatic residue.

6. The compound according to claim 1, wherein
each R$^4$ independently represents H; F; Cl; Br; CN; CF$_3$; OCF$_3$; CH$_3$, OCH$_3$ or S(=O)$_2$CH$_3$.

7. The compound according to claim 1, wherein
R$^1$ represents the partial structure (T1),

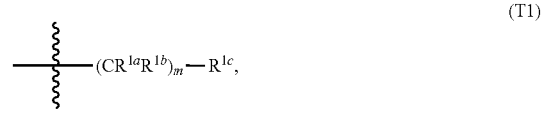

wherein m denotes 0, 1, or 2, $R^{1a}$ and $R^{1b}$ each independently of one another represent H, F, Cl, Br, I, O—$C_{1-4}$-aliphatic residue or $C_{1-4}$-aliphatic residue, $R^{1c}$ denotes $C_{1-4}$-aliphatic residue, unsubstituted or mono- or polysubstituted with at least one substituent selected from the group consisting of F, Cl, Br, I, O—$C_{1-4}$-aliphatic residue, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and O—$C_{1-4}$-aliphatic residue, or denotes $C_{3-10}$-cycloaliphatic residue or 3 to 10 membered heterocycloaliphatic residue, in each case unsubstituted or mono- or polysubstituted with at least one substituent selected from the group consisting of F, Cl, Br, I, O—$C_{1-4}$-aliphatic residue, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and O—$C_{1-4}$-aliphatic residue, or denotes aryl or heteroaryl, in each case unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$, $C(=O)OC_2H_5$, $C_{3-6}$-cycloaliphatic residue, 3 to 7 membered heterocycloaliphatic residue, benzyl, phenyl, thienyl or pyridyl, wherein benzyl, phenyl, thienyl and pyridyl, may in each case may be unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$ and $C(=O)OC_2H_5$, and wherein the $C_{3-6}$ cycloaliphatic residue and the 3 to 7 membered heterocycloaliphatic residue may in each case may be unsubstituted or mono- or polysubstituted with at least one substituent selected from the group consisting of F, Cl, Br, I, OH, =O, O—$C_{1-4}$-aliphatic residue, $OCF_3$, $CF_3$ $C_{1-4}$-aliphatic residue and $C(=O)OH$.

8. The compound according to claim 7, wherein m denotes 1 or 2, $R^{1a}$ and $R^{1b}$ represent H, $R^{1c}$ denotes $C_{1-4}$-aliphatic residue, unsubstituted or mono- or polysubstituted with at least one substituent selected from the group consisting of F, Cl, Br, I, O—$C_{1-4}$-aliphatic residue, $CF_3$ and $C_{1-4}$-aliphatic residue, or denotes $C_{3-10}$-cycloaliphatic residue or 3 to 10 membered heterocycloaliphatic residue, in each case unsubstituted or mono- or polysubstituted with at least one substituent selected from the group consisting of F, Cl, Br, I, O—$C_{1-4}$-aliphatic residue, $CF_3$ and $C_{1-4}$-aliphatic residue, or m denotes 0 and $R^{1c}$ denotes aryl or heteroaryl, in each case unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$, $C(=O)OC_2H_5$, $C_{3-6}$-cycloaliphatic residue, 3 to 7 membered heterocycloaliphatic residue, benzyl, phenyl, thienyl or pyridyl, wherein benzyl, phenyl, thienyl and pyridyl, may in each case may be unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, $C(=O)CH_3$, $C(=O)C_2H_5$, $C(=O)OCH_3$ and $C(=O)OC_2H_5$, and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, OH, =O, O—$C_{1-4}$ aliphatic residue, $OCF_3$, $CF_3$, $C_{1-4}$-aliphatic residue and $C(=O)OH$.

9. The compound according to claim 1, wherein $R^3$ denotes a $C_{2-6}$-aliphatic residue, unsubstituted or mono- or polysubstituted with at least one substituent selected from the group consisting of F, Cl, Br, I, OH, =O, O—$C_{1-4}$-aliphatic residue, $OCF_3$, SH, $SCF_3$, S—$C_{1-4}$-aliphatic residue, $CF_3$, CN and $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and O—$C_{1-4}$-aliphatic residue, or denotes $C_{3-6}$-cycloaliphatic residue or 3 to 7 membered heterocycloaliphatic residue, in each case unsubstituted or mono- or polysubstituted with at least one substituent selected from the group consisting of F, Cl, Br, I, OH, =O, O—$C_{1-4}$-aliphatic residue, $OCF_3$, $SCF_3$, (=O)—O—$C_{1-4}$-aliphatic residue, S—$C_{1-4}$-aliphatic residue, $CF_3$, CN and $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-7}$-cycloaliphatic residue or the 3 to 7 membered heterocycloaliphatic residue may in each case optionally linked via a $C_{1-4}$-aliphatic group, which in turn may be unsubstituted or mono- or polysubstituted with at least one substituent selected from the group consisting of F, Cl, OH, =O, O—$C_{1-4}$-aliphatic residue, $OCF_3$, $SCF_3$, $CF_3$, CN and $C_{1-4}$-aliphatic residue, or $R^3$ denotes S—$R^5$ or O—$R^6$, wherein $R^5$ and $R^6$ in each case denote $C_{1-8}$-aliphatic residue, unsubstituted or mono- or polysubstituted with at least one substituent selected from the group consisting of F, Cl, Br, I, OH, =O, O—$C_{1-4}$-aliphatic residue, $OCF_3$, SH, $SCF_3$, S—$C_{1-4}$-aliphatic residue, NH($C_{1-4}$-aliphatic residue), N($C_{1-4}$-aliphatic residue)$_2$, $CF_3$ and $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and O—$C_{1-4}$-aliphatic residue, or in each case denote $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue, and wherein the $C_{3-6}$-cycloaliphatic residue or the 3 to 7 membered heterocycloaliphatic residue may be linked via a $C_{1-4}$-aliphatic group, which in turn may be unsubstituted or mono- or polysubstituted with at least one substituent selected from the group consisting of F, Cl, OH, =O, O—$C_{1-4}$-aliphatic residue, $OCF_3$, $CF_3$, CN and $C_{1-4}$-aliphatic residue, on the condition that if $R^5$ or $R^6$ denotes 3 to 7 membered heterocycloaliphatic residue, the 3 to 7 membered heterocycloaliphatic residue is linked via a carbon atom, or $R^3$ denotes $N(R^7R^8)$, wherein $R^7$ denotes $C_{1-6}$-aliphatic residue, unsubstituted or mono- or polysubstituted with at least one substituent selected from the group consisting of F, Cl, Br, I, OH, =O, O—$C_{1-4}$-aliphatic residue, $OCF_3$, $SCF_3$, $CF_3$ and $C_{1-4}$-aliphatic residue wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue, or denotes $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue, and wherein the $C_{3-6}$-cycloaliphatic residue or the 3 to 7 membered heterocycloaliphatic residue may in each case be linked, via a $C_{1-4}$-aliphatic group, which in turn may be unsubstituted or mono- or polysubstituted with at least one substituent selected from the group consisting of F, Cl, OH, =O, O—$C_{1-4}$-aliphatic residue, $OCF_3$, $SCF_3$, $CF_3$, CN and $C_{1-4}$-aliphatic residue, on the condition that if $R^7$ denotes 3 to 7 membered heterocycloaliphatic residue, the 3 to 7 membered heterocycloaliphatic residue is linked via a carbon atom, and $R^8$ denotes $C_{1-6}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$, CN and $C_{1-4}$-aliphatic residue, wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue, or $R^7$ and $R^8$ form together with the nitrogen atom connecting them a 3 to 10 membered heterocycloaliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$, CN and $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and O—$C_{1-4}$-aliphatic residue, and wherein the 3 to 10 membered heterocycloaliphatic residue formed by $R^7$ and $R^8$ together with the nitrogen atom connecting them may optionally be condensed with aryl or heteroaryl, wherein the aryl or heteroaryl residues condensed in this way can for their part be respectively unsubstituted or mono- or polysubstituted with at least one substituent selected from the group consisting of F, Cl, OH, O—$C_{1-4}$-aliphatic residue, $OCF_3$, $SCF_3$, $CF_3$, CN, $C_{1-4}$-aliphatic residue, C(=O)OH, $C_{3-6}$ cycloaliphatic residue, 3 to 7 membered heterocycloaliphatic residue,

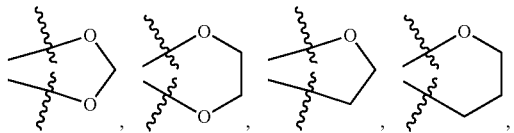

benzyl, phenyl, thienyl, and pyridyl, wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue, and wherein benzyl, phenyl, thienyl, and pyridyl, may in each case may be unsubstituted or mono- or polysubstituted with at least one substituent selected from the group consisting of F, Cl, OH, O—$C_{1-4}$-aliphatic residue, $OCF_3$, $OCH_2CH_2OH$, $OCH_2OCH_3$, $SCF_3$, $CF_3$, CN, $C_{1-4}$-aliphatic residue and C(=O)OH, and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, OH, =O, O—$C_{1-4}$-aliphatic residue, $OCF_3$, $CF_3$, CN, $C_{1-4}$-aliphatic residue and C(=O)OH.

10. The compound according to claim 1, wherein $R^3$ denotes $C_{2-6}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, or denotes $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with OH or O—$C_{1-4}$-aliphatic residue, and wherein the $C_{3-6}$-cycloaliphatic residue or the 3 to 7 membered heterocycloaliphatic residue may in each case optionally linked via a $C_{1-4}$-aliphatic group, or $R^3$ denotes S—$R^5$ or O-$R^6$, wherein $R^5$ and $R^6$ in each case denote $C_{1-6}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue, or in each case denote $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue, and wherein the $C_{3-6}$-cycloaliphatic residue or the 3 to 7 membered heterocycloaliphatic residue in each case may be linked via an unsubstituted $C_{1-4}$-aliphatic group, on the condition that if $R^5$ or $R^6$ denotes 3 to 7 membered heterocycloaliphatic residue, the 3 to 7 membered heterocycloaliphatic residue is linked via a carbon atom, or $R^3$ denotes N($R^7R^8$), wherein $R^7$ denotes $C_{1-6}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue, or denotes $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue, and wherein the $C_{3-6}$-cycloaliphatic residue or the 3 to 7 membered heterocycloaliphatic residue is in each case linked via a unsubstituted $C_{1-4}$-aliphatic group, on the condition that if $R^7$ denotes 3 to 7 membered heterocycloaliphatic residue, the 3 to 7 membered heterocycloaliphatic residue is linked via a carbon atom, and $R^8$ denotes unsubstituted $C_{1-4}$-aliphatic residue, or $R^7$ and $R^8$ form together with the nitrogen atom connecting them a 3 to 7 membered heterocycloaliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$, CN and $C_{1-4}$-aliphatic residue, wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue, and wherein the 3 to 7 membered heterocycloaliphatic residue formed by $R^7$ and $R^8$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, OH, O—$C_{1-4}$-aliphatic residue, $OCF_3$, $SCF_3$, $CF_3$, CN, $C_{1-4}$-aliphatic residue, C(=O)OH, benzyl, phenyl, and pyridyl, wherein the $C_{1-4}$-aliphatic residue in each case may be unsubstituted or mono- or polysubstituted with at least one substituent selected from the group consisting of F, Cl, OH and O—$C_{1-4}$-aliphatic residue, and wherein benzyl, phenyl, and pyridyl, may in each case may be unsubstituted or mono- or polysubstituted with at least one substituent selected from the group consisting of F, Cl, $OCH_3$, $OCF_3$, $OCH_2CH_2OH$, $OCH_2CH_2OCH_3$, $SCF_3$, $CF_3$ and $C_{1-4}$-aliphatic residue.

11. The compound according to claim 1, wherein $A^1$, $A^2$ and $A^3$ independently of each other represent $CR^4$, N, O, S or N($CH_3$), $A^4$ represents $CR^4$ or N, and n denotes 0 or 1, with the proviso, that at least one of $A^1$, $A^2$, $A^3$ and $A^4$ does not represent $CR^4$, and with the proviso, that if n denotes 0, then precisely one of $A^1$, $A^2$ and $A^3$ represents O, S or N($CH_3$), or if n denotes 1, then $A^1$, $A^2$ and $A^3$ independently of each other represent $CR^4$ or N, $R^1$ represents the partial structure (T1),

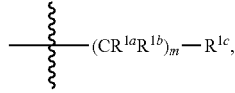

(T1)

wherein m denotes 0, 1, or 2, $R^{1a}$ and $R^{1b}$ each independently of one another represent H, F, Cl, O—$C_{1-4}$-aliphatic residue or $C_{1-4}$-aliphatic residue, $R^{1c}$ denotes $C_{1-4}$-aliphatic residue, unsubstituted or mono- or polysubstituted with at least one substituent selected from the group consisting of F, Cl, O—$C_{1-4}$-aliphatic residue, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and O—$C_{1-4}$-aliphatic residue, or denotes $C_{3-10}$-cycloaliphatic residue or 3 to 10 membered heterocycloaliphatic residue, in each case unsubstituted or mono- or polysubstituted with at least one substituent selected from the group consisting of F, Cl, O—$C_{1-4}$-aliphatic residue, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and O—$C_{1-4}$-aliphatic residue, or denotes aryl or heteroaryl, in each case unsubstituted or mono- or polysubstituted with at least one substituent selected from the group consisting of F, Cl, OH, O—$C_{1-4}$-aliphatic residue, $OCF_3$, $CF_3$, CN, $C_{1-4}$-aliphatic residue, C(=O)$CH_3$, C(=O)$C_2H_5$, C(=O)$OCH_3$, C(=O)$OC_2H_5$, $C_{3-6}$-cycloaliphatic residue, 3 to 7 membered heterocycloaliphatic residue, benzyl, phenyl, thienyl or pyridyl, wherein benzyl, phenyl, thienyl and pyridyl, may in each case may be unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, C(=O)$CH_3$, C(=O)$C_2H_5$, C(=O)$OCH_3$ and C(=O)$OC_2H_5$, and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, OH, =O, O—$C_{1-4}$-aliphatic residue, $OCF_3$, $CF_3$ $C_{1-4}$-aliphatic residue and C(=O)OH;

$R^2$ represents F; Cl; Br; I; CN; $CF_3$; $NO_2$; $OCF_3$; $SCF_3$; $C_{1-4}$-aliphatic residue, S—$C_{1-4}$-aliphatic residue or O—$C_{1-4}$-aliphatic residue, wherein the $C_{1-4}$-aliphatic residue in each case may be unsubstituted or mono- or polysubstituted with at least one substituent selected from the group consisting of F, Cl, =O, OH and O—$C_{1-4}$-aliphatic residue, $R^3$ denotes $C_{2-6}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, or denotes $C_{3-10}$-cycloaliphatic residue or 3 to 10 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with OH or O—$C_{1-4}$-aliphatic residue, and wherein the $C_{3-10}$-cycloaliphatic residue or the 3 to 10 membered heterocycloaliphatic residue may in each case optionally linked via a $C_{1-4}$-aliphatic group, or $R^3$ denotes S—$R^5$ or O—$R^6$, wherein $R^5$ and $R^6$ in each case denote $C_{1-8}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue, or in each case denote $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue, and wherein the $C_{3-6}$-cycloaliphatic residue or the 3 to 7 membered heterocycloaliphatic residue in each case may be linked via an unsubstituted $C_{1-4}$-aliphatic group, on the condition that if $R^5$ or $R^6$ denotes 3 to 7 membered heterocycloaliphatic residue, the 3 to 7 membered heterocycloaliphatic residue is linked via a carbon atom, or $R^3$ denotes N($R^7R^8$), wherein $R^7$ denotes $C_{1-8}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue, or denotes $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, C(=O)—O—$C_{1-4}$-aliphatic residue, $CF_3$ and $C_{1-4}$-aliphatic residue, wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue, and wherein the $C_{3-6}$-cycloaliphatic residue or the 3 to 7 membered heterocycloaliphatic residue is in each case linked via an unsubstituted $C_{1-4}$-aliphatic group, on the condition that if R⁷ denotes 3 to 7 membered heterocycloaliphatic residue, the 3 to 7 membered heterocycloaliphatic residue is linked via a carbon atom, and R⁸ denotes unsubstituted $C_{1-4}$-aliphatic residue, or R⁷ and R⁸ form together with the nitrogen atom connecting them a 3 to 7 membered heterocycloaliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$, CN and $C_{1-4}$-aliphatic residue, wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue, and wherein the 3 to 7 membered heterocycloaliphatic residue formed by R⁷ and R⁸ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, OH, O—$C_{1-4}$-aliphatic residue, $OCF_3$, $SCF_3$, $CF_3$, CN, $C_{1-4}$-aliphatic residue, C(=O)OH, benzyl, phenyl, and pyridyl, wherein the $C_{1-4}$-aliphatic residue in each case may be unsubstituted or mono- or polysubstituted with at least one substituent selected from the group consisting of F, Cl, OH, and O—$C_{1-4}$-aliphatic residue, and wherein benzyl, phenyl, and pyridyl, may in each case may be unsubstituted or mono- or polysubstituted with at least one substituent selected from the group consisting of F, Cl, $OCH_3$, $OCF_3$, $OCH_2CH_2OH$, O $CH_2CH_2OCH_3$, SH, $SCF_3$, $CF_3$ and $C_{1-4}$-aliphatic residue, and each R⁴ independently represents H, F, Cl, Br, CN, $CF_3$, $OCF_3$, $CH_3$, $OCH_3$ or S(=O)$_2CH_3$.

12. A compound selected from the group consisting of:
1 2-Ethylsulfanyl-N-[(3-fluorophenyl)-methyl]-4-methyl-[1,5]naphthyridine-3-carboxylic acid amide;
2 2-Ethylsulfanyl-N-[(4-fluorophenyl)-methyl]-4-methyl-[1,5]naphthyridine-3-carboxylic acid amide;
3 2-Ethylsulfanyl-N-[(3-fluorophenyl)-methyl]-4-methyl-[1,6]naphthyridine-3-carboxylic acid amide;
4 2-Ethylsulfanyl-N-[(4-fluorophenyl)-methyl]-4-methyl-[1,6]naphthyridine-3-carboxylic acid amide;
5 2-Ethylsulfanyl-N-[(3-fluorophenyl)-methyl]-4-methyl-[1,7]naphthyridine-3-carboxylic acid amide;
6 2-Ethylsulfanyl-N-[(4-fluorophenyl)-methyl]-4-methyl-[1,7]naphthyridine-3-carboxylic acid amide;
7 2-Ethylsulfanyl-N-[(3-fluorophenyl)-methyl]-4-methyl-[1,8]naphthyridine-3-carboxylic acid amide;
8 2-Ethylsulfanyl-N-[(4-fluorophenyl)-methyl]-4-methyl-[1,8]naphthyridine-3-carboxylic acid amide;
9 2-Ethylsulfanyl-N-[(3-fluorophenyl)-methyl]-4-methyl-7-(trifluoromethyl)-[1,8]naphthyridine-3-carboxylic acid amide;
10 2-Ethylsulfanyl-N-[(4-fluorophenyl)-methyl]-4-methyl-7-(trifluoromethyl)-[1,8]naphthyridine-3-carboxylic acid amide;
11 2-Ethylsulfanyl-N-[(3-fluorophenyl)-methyl]-4-methyl-7-(trifluoromethyl)-[1,6]naphthyridine-3-carboxylic acid amide;
12 2-Ethylsulfanyl-N-[(4-fluorophenyl)-methyl]-4-methyl-7-(trifluoromethyl)-[1,6]naphthyridine-3-carboxylic acid amide;
13 2-Ethylsulfanyl-N-[(3-fluorophenyl)-methyl]-4-methyl-7-(trifluoromethyl)-[1,5]naphthyridine-3-carboxylic acid amide;
14 2-Ethylsulfanyl-N-[(4-fluorophenyl)-methyl]-4-methyl-7-(trifluoromethyl)-[1,5]naphthyridine-3-carboxylic acid amide;
15 5-Ethylsulfanyl-N-[(3-fluorophenyl)-methyl]-7-methyl-thieno[3,2-b]pyridine-6-carboxylic acid amide;
16 6-Ethylsulfanyl-N-[(3-fluorophenyl)-methyl]-4-methyl-thieno[2,3-b]pyridine-5-carboxylic acid amide;
17 5-Ethoxy-N-[(3-fluorophenyl)-methyl]-7-methyl-2-(trifluoromethyl)-thieno[3,2-b]pyridine-6-carboxylic acid amide; and
18 6-Ethoxy-N-[(3-fluorophenyl)-methyl]-4-methyl-2-(trifluoromethyl)-thieno[2,3-b]pyridine-5-carboxylic acid amide;

in the form of a free compound, a solvate and and/or a physiologically acceptable salt.

13. A pharmaceutical composition comprising at least one compound according to claim 1 in the form of an individual single stereoisomer or a mixture of the stereoisomers in any mixing ratio, and/or in the form of a solvate and and/or a salt of physiologically acceptable acid or base, and optionally at least one pharmaceutically acceptable auxiliary and/or optionally at least one further active ingredient.

14. A compound of general formula (I):

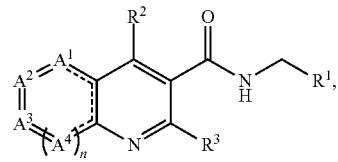

wherein

A¹, A² and A³ independently of each other represent $CR^4$, N, O, S or $N(CH_3)$, A⁴ represents $CR^4$ or N, and n denotes 0 or 1, with the proviso, that at least one of A¹, A², A³ and A⁴ does not represent $CR^4$, and with the proviso, that if n denotes 0, then precisely one of A¹, A² and A³ represents O, S or $N(CH_3)$, or if n denotes 1, then A¹, A² and A³ independently of each other represent $CR^4$ or N, R¹ represents $C_{1-10}$-aliphatic residue, unsubstituted or mono- or polysubstituted; $C_{3-10}$-cycloaliphatic residue or 3 to 10 membered heterocycloaliphatic residue, in each case unsubstituted or mono- or polysubstituted and in each case optionally linked via a $C_{1-8}$-aliphatic group, which in turn may be unsubstituted or mono- or polysubstituted; aryl or heteroaryl, in each case unsubstituted or mono- or polysubstituted and in each case optionally linked via a $C_{1-8}$-aliphatic group, which in turn may be unsubstituted or mono- or polysubstituted;

R² represents F; Cl; Br; I; CN; $CF_3$; C(=O)H; $NO_2$; $OCF_3$; $SCF_3$; $C_{1-4}$-aliphatic residue, C(=O)—$C_{1-4}$-aliphatic residue, C(=O)—O—C$_{1-4}$-aliphatic residue, C(=O)—NH—C$_{1-4}$-aliphatic residue, C(=O)—N(C$_{1-4}$-aliphatic residue)$_2$, O—C$_{1-4}$-aliphatic residue, O—C(=O)—C$_{1-4}$-aliphatic residue, S—C$_{1-4}$-aliphatic residue, S(=O)$_2$—C$_{1-4}$-aliphatic residue, S(=O)$_2$—O—C$_{1-4}$-aliphatic residue, wherein the C$_{1-4}$-aliphatic residue may be in each case be unsubstituted or mono- or polysubstituted;

C$_{3-6}$-cycloaliphatic residue or 3 to 7 membered heterocycloaliphatic residue, in each case unsubstituted or mono- or polysubstituted and in each case optionally linked via a C$_{1-4}$-aliphatic group, which in turn may be unsubstituted or mono- or polysubstituted; and R$^3$ represents C$_{2-10}$-aliphatic residue, mono- or polysubstituted; C$_{3-10}$-cycloaliphatic residue or 3 to 10 membered heterocycloaliphatic residue, in each case unsubstituted or mono- or polysubstituted and in each case optionally linked via a C$_{1-8}$-aliphatic group, which in turn may be unsubstituted or mono- or polysubstituted, or denotes S—R$^5$, O—R$^6$ or N(R$^7$R$^8$), wherein R$^5$ and R$^6$ in each case represent C$_{1-10}$-aliphatic residue, unsubstituted or mono- or polysubstituted; C$_{3-10}$-cycloaliphatic residue or 3 to 10 membered heterocycloaliphatic residue, in each case unsubstituted or mono- or polysubstituted and in each case optionally linked via a C$_{1-8}$-aliphatic group, which in turn may be unsubstituted or mono- or polysubstituted;

with the proviso, that if R$^5$ or R$^6$ denote a 3 to 10 membered heterocycloaliphatic residue, than the 3 to 10 membered heterocycloaliphatic residue is linked via a carbon atom, R$^7$ represents C$_{1-10}$-aliphatic residue, unsubstituted or mono- or polysubstituted; C$_{3-10}$-cycloaliphatic residue or 3 to 10 membered heterocycloaliphatic residue, in each case unsubstituted or mono- or polysubstituted and in each case optionally linked via a C$_{1-8}$-aliphatic group, which in turn may be unsubstituted or mono- or polysubstituted;

with the proviso that if R$^7$ denotes 3 to 10 membered heterocycloaliphatic residue, the 3 to 10 membered heterocycloaliphatic residue is linked via a carbon atom; and R$^8$ denotes C$_{1-10}$-aliphatic residue, unsubstituted or mono- or polysubstituted;

or

R$^7$ and R$^8$ form together with the nitrogen atom connecting them a 3 to 10 membered heterocycloaliphatic residue, unsubstituted or mono- or polysubstituted;

and each R$^4$ independently represents H, F; Cl; Br; I; CN; CF$_3$; CHF$_2$; CH$_2$F; OCF$_3$; OCHF$_2$; OCH$_2$F; SCF$_3$; O—C$_{1-4}$-aliphatic residue, C$_{1-4}$-aliphatic residue or S(=O)$_2$—C$_{1-4}$-aliphatic residue;

in which an "aliphatic group" and "aliphatic residue" may in each case be branched or unbranched, saturated or unsaturated, in which a "cycloaliphatic residue" and a "heterocycloaliphatic residue" may in each case be saturated or unsaturated, in which "mono- or polysubstituted" with respect to an "aliphatic group", an "aliphatic residue", a "cycloaliphatic residue" and a "heterocycloaliphatic residue" relates, with respect to the corresponding residues or groups, to the substitution of one or more hydrogen atoms each independently of one another by at least one substituent selected from the group consisting of F, Cl, Br, I, NO$_2$, NH$_2$, NH(C$_{1-4}$-aliphatic residue), N(C$_{1-4}$-aliphatic residue)$_2$, NH—C(=O)—C$_{1-4}$ aliphatic residue, N(C$_{1-4}$ aliphatic residue)-C(=O)—C$_{1-4}$ aliphatic residue, NH—S(=O)$_2$—C$_{1-4}$ aliphatic residue, N(C$_{1-4}$ aliphatic residue)-S(=O)$_2$—C$_{1-4}$ aliphatic residue, =O, OH, OCF$_3$, O—C$_{1-4}$-aliphatic residue, O—C(=O)—C$_{1-4}$-aliphatic residue, SH, SCF$_3$, S—C$_{1-4}$-aliphatic residue, S(=O)$_2$OH, S(=O)$_2$—C$_{1-4}$-aliphatic residue, S(=O)$_2$—O—C$_{1-4}$-aliphatic residue, S(=O)$_2$—NH(C$_{1-4}$-aliphatic residue), S(=O)$_2$—N(C$_{1-4}$-aliphatic residue)$_2$, CN, CF$_3$, CHO, COON, C$_{1-4}$-aliphatic residue, C(=O)—C$_{1-4}$-aliphatic residue, C(=O)—O—C$_{1-4}$-aliphatic residue, C$_{3-6}$-cycloaliphatic residue, 3 to 7 membered heterocycloaliphatic residue, C(=O)NH$_2$, a C(=O)—NH(C$_{1-4}$-aliphatic residue) and C(=O)—N(C$_{1-4}$-aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO$_2$, NH$_2$,

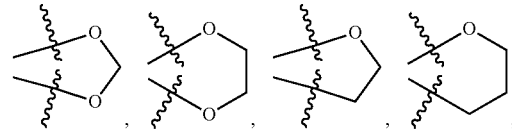

NH(C$_{1-4}$-aliphatic residue), N(C$_{1-4}$-aliphatic residue)$_2$, NH—C(=O)—C$_{1-4}$-aliphatic residue, N(C$_{1-4}$ aliphatic residue)-C(=O)—C$_{1-4}$ aliphatic residue, NH—S(=O)$_2$—C$_{1-4}$ aliphatic residue, N(C$_{1-4}$ aliphatic residue)-S(=O)$_2$—C$_{1-4}$ aliphatic residue, OH, OCF$_3$, O—C$_{1-4}$-aliphatic residue, O—C(=O)—C$_{1-4}$-aliphatic residue, SH, SCF$_3$, S—C$_{1-4}$-aliphatic residue, S(=O)$_2$OH, S(=O)$_2$—C$_{1-4}$-aliphatic residue, S(=O)$_2$—O—C$_{1-4}$-aliphatic residue, S(=O)$_2$—NH(C$_{1-4}$-aliphatic residue), S(=O)$_2$—N(C$_{1-4}$-aliphatic residue)$_2$, CN, CF$_3$, C(=O)H, C(=O)OH, C$_{1-4}$-aliphatic residue, C(=O)—C$_{1-4}$-aliphatic residue, C(=O)—O—C$_{1-4}$-aliphatic residue, C$_{3-6}$-cycloaliphatic residue, 3 to 7 membered heterocycloaliphatic residue, benzyl, aryl, heteroaryl, C(=O)NH$_2$, C(=O)—NH(C$_{1-4}$-aliphatic residue) and C(=O)—N(C$_{1-4}$-aliphatic residue)$_2$;

in the form of an individual single stereoisomer or a mixture of the stereoisomers in any mixing ratio, and/or in the form of a free compound, a solvate and and/or a physiologically acceptable salt.

15. The compound according to claim 1, wherein:

A$^1$, A$^2$ and A$^3$ independently of each other represent CR$^4$, N, O, S or N(CH$_3$);

A$^4$ represents CR$^4$ or N; and n denotes 0 or 1;

with the proviso, that at least one of A$^1$, A$^2$, A$^3$ and A$^4$ does not represent CR$^4$;

and with the proviso, that if n denotes 0, then precisely one of A$^1$, A$^2$ and A$^3$ represents O, S or N(CH$_3$); or if n denotes 1, then A$^1$, A$^2$ and A$^3$ independently of each other represent CR$^4$ or N;

R$^1$ denotes aryl or heteroaryl, in each case unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, C(=O)$CH_3$, C(=O)$C_2H_5$, C(=O)$OCH_3$, C(=O)$OC_2H_5$, $C_{3-6}$-cycloaliphatic residue, 3 to 7 membered heterocycloaliphatic residue, benzyl, phenyl, thienyl or pyridyl;

wherein benzyl, phenyl, thienyl and pyridyl, may in each case may be unsubstituted or mono- or polysubstituted with at least one substituent selected from the group consisting of F, Cl, Br, I, OH, O—$C_{1-4}$-aliphatic residue, $OCF_3$, $CF_3$, CN, $C_{1-4}$-aliphatic residue, C(=O)$CH_3$, C(=O)$C_2H_5$, C(=O)$OCH_3$ and C(=O)$OC_2H_5$;

and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, OH, =O, O—$C_{1-4}$aliphatic residue, $OCF_3$, $CF_3$, $C_{1-4}$-aliphatic residue and C(=O)OH;

$R^2$ represents F; Cl; Br; I; CN; $CF_3$; $NO_2$; $OCF_3$; $SCF_3$; $C_{1-4}$-aliphatic residue, S—$C_{1-4}$-aliphatic residue or O—$C_{1-4}$-aliphatic residue;

wherein the $C_{1-4}$-aliphatic residue in each case may be unsubstituted or mono- or polysubstituted with at least one substituent selected from the group consisting of F, Cl, Br, I, =O, OH and O—$C_{1-4}$-aliphatic residue;

$R^3$ denotes S—$R^5$ or O—$R^6$, wherein $R^5$ and $R^6$ in each case denote $C_{1-6}$-aliphatic residue, unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue;

wherein the $C_{1-4}$-aliphatic residue in each case may be unsubstituted or mono- or polysubstituted with at least one substituent selected from the group consisting of F, Cl, OH, $CF_3$ and O—$C_{1-4}$-aliphatic residue;

or in each case denote $C_{3-6}$-cycloaliphatic residue or 3 to 7 membered heterocycloaliphatic residue, in each case unsubstituted or mono- or polysubstituted with at least one substituent selected from the group consisting of F, Cl, OH, =O, O—$C_{1-4}$-aliphatic residue, $OCF_3$, $SCF_3$, $CF_3$ and $C_{1-4}$-aliphatic residue;

wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue;

and wherein the $C_{3-6}$-cycloaliphatic residue or the 3 to 7 membered heterocycloaliphatic residue in each case may be linked via an unsubstituted $C_{1-4}$-aliphatic group;

on the condition that if $R^5$ or $R^6$ denotes 3 to 7 membered heterocycloaliphatic residue, the 3 to 7 membered heterocycloaliphatic residue is linked via a carbon atom; and each $R^4$ independently represents H; F; Cl; Br; CN; $CF_3$; $OCF_3$; $CH_3$, $OCH_3$ or S(=O)$_2CH_3$.

16. A pharmaceutical composition comprising at least one compound according to claim 12
in the form of an individual single stereoisomer or a mixture of the stereoisomers in any mixing ratio, and/or in the form of a solvate and and/or a salt of physiologically acceptable acid or base, and optionally at least one pharmaceutically acceptable auxiliary and/or optionally at least one further active ingredient.

17. A pharmaceutical composition comprising at least one compound according to claim 14
in the form of an individual single stereoisomer or a mixture of the stereoisomers in any mixing ratio, and/or in the form of a solvate and and/or a salt of physiologically acceptable acid or base, and optionally at least one pharmaceutically acceptable auxiliary and/or optionally at least one further active ingredient.

18. A method for treatment of a disorder and/or disease selected from the group consisting of pain, acute pain, chronic pain, neuropathic pain, muscular pain, visceral pain and inflammatory pain, said method comprising administering to a patient in need of such treatment an effective amount therefor of a compound according to claim 1.

19. A method for treatment of a disorder and/or disease selected from the group consisting of pain, acute pain, chronic pain, neuropathic pain, muscular pain, visceral pain and inflammatory pain, said method comprising administering to a patient in need of such treatment an effective amount therefor of a compound according to claim 12.

20. A method for treatment of a disorder and/or disease selected from the group consisting of pain, acute pain, chronic pain, neuropathic pain, muscular pain, visceral pain and inflammatory pain, said method comprising administering to a patient in need of such treatment an effective amount therefor of a compound according to claim 14.

* * * * *